(12) United States Patent
Wolf et al.

(10) Patent No.: US 9,486,278 B2
(45) Date of Patent: **\*Nov. 8, 2016**

(54) METHODS AND DEVICES TO TREAT NASAL AIRWAYS

(71) Applicant: AERIN MEDICAL INC., Sunnyvale, CA (US)

(72) Inventors: Scott J. Wolf, Menlo Park, CA (US); Andrew Frazier, Sunnyvale, CA (US)

(73) Assignee: AERIN MEDICAL INC., Sunnyvale, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/540,050

(22) Filed: Nov. 13, 2014

(65) Prior Publication Data

US 2015/0073395 A1    Mar. 12, 2015

Related U.S. Application Data

(63) Continuation of application No. 13/495,844, filed on Jun. 13, 2012, now Pat. No. 8,936,594.

(60) Provisional application No. 61/603,864, filed on Feb. 27, 2012, provisional application No. 61/496,930, filed on Jun. 14, 2011.

(51) Int. Cl.
*A61B 18/18*     (2006.01)
*A61B 18/14*     (2006.01)
(Continued)

(52) U.S. Cl.
CPC ............ *A61B 18/1485* (2013.01); *A61B 5/01* (2013.01); *A61B 18/1442* (2013.01);
(Continued)

(58) Field of Classification Search
CPC ............... A61B 17/320068; A61B 18/1442; A61B 18/1485; A61B 18/16; A61B 18/1815; A61B 18/20; A61B 2018/00005; A61B 2018/00023; A61B 2018/00327; A61B 2018/00577; A61B 2018/00702; A61B 2018/00821; A61B 2018/00922; A61B 2018/143; A61B 2018/00583; A61B 2018/00595; A61B 2018/1807; A61B 2018/1861; A61B 5/01; A61F 5/08
See application file for complete search history.

(56) References Cited

U.S. PATENT DOCUMENTS

| 4,887,605 A | 12/1989 | Angelsen et al. |
| 5,348,008 A | 9/1994 | Bornn et al. |

(Continued)

FOREIGN PATENT DOCUMENTS

| CN | 101325919 A | 12/2008 |
| WO | 2007/037895 | 4/2007 |

(Continued)

OTHER PUBLICATIONS

International Search Report, Issued by the International Searching Authority for corresponding PCT Application No. PCT/US2014/054726, (Dec. 23, 2014) pp. 1-2.

(Continued)

*Primary Examiner* — Goerge Manuel
(74) *Attorney, Agent, or Firm* — Dorsey & Whitney LLP; Scott M. Smith

(57) ABSTRACT

Methods and devices for treating nasal airways are provided. Such devices and methods may improve airflow through an internal and/or external nasal valve, and comprise the use of mechanical re-shaping, energy application and other treatments to modify the shape, structure, and/or air flow characteristics of an internal nasal valve, an external nasal valve or other nasal airways.

24 Claims, 43 Drawing Sheets

(51) Int. Cl.
   *A61B 18/20* (2006.01)
   *A61F 5/08* (2006.01)
   *A61B 5/01* (2006.01)
   *A61B 18/16* (2006.01)
   *A61B 18/00* (2006.01)
   *A61B 17/32* (2006.01)

(52) U.S. Cl.
   CPC .......... *A61B 18/1815* (2013.01); *A61B 18/20* (2013.01); *A61F 5/08* (2013.01); *A61B 17/320068* (2013.01); *A61B 18/16* (2013.01); *A61B 2018/00005* (2013.01); *A61B 2018/00023* (2013.01); *A61B 2018/00327* (2013.01); *A61B 2018/00577* (2013.01); *A61B 2018/00702* (2013.01); *A61B 2018/00821* (2013.01); *A61B 2018/00922* (2013.01); *A61B 2018/143* (2013.01); *A61B 2018/1807* (2013.01); *A61B 2018/1861* (2013.01)

(56) References Cited

U.S. PATENT DOCUMENTS

| | | | |
|---|---|---|---|
| 5,533,499 | A | 7/1996 | Johnson |
| 5,624,439 | A | 4/1997 | Edwards et al. |
| 5,674,191 | A | 10/1997 | Edwards et al. |
| 5,707,349 | A | 1/1998 | Edwards |
| 5,718,702 | A | 2/1998 | Edwards |
| 5,728,094 | A | 3/1998 | Edwards |
| 5,730,719 | A | 3/1998 | Edwards |
| 5,738,114 | A | 4/1998 | Edwards |
| 5,743,870 | A | 4/1998 | Edwards |
| 5,743,904 | A | 4/1998 | Edwards |
| 5,746,224 | A | 5/1998 | Edwards |
| 5,800,429 | A | 9/1998 | Edwards |
| 5,807,306 | A | 9/1998 | Shapland et al. |
| 5,816,095 | A | 10/1998 | Nordell et al. |
| 5,817,049 | A | 10/1998 | Edwards |
| 5,820,580 | A | 10/1998 | Edwards et al. |
| 5,823,197 | A | 10/1998 | Edwards |
| 5,827,277 | A | 10/1998 | Edwards |
| 5,843,021 | A | 12/1998 | Edwards et al. |
| 5,843,077 | A | 12/1998 | Edwards |
| 5,846,235 | A | 12/1998 | Pasricha et al. |
| 5,879,349 | A | 3/1999 | Edwards |
| 6,045,549 | A | 4/2000 | Smethers et al. |
| 6,096,033 | A | 8/2000 | Tu et al. |
| 6,102,907 | A | 8/2000 | Smethers et al. |
| 6,109,268 | A | 8/2000 | Thapliyal et al. |
| 6,126,657 | A | 10/2000 | Edwards et al. |
| 6,131,579 | A | 10/2000 | Thorson et al. |
| 6,139,546 | A | 10/2000 | Koenig et al. |
| 6,152,143 | A | 11/2000 | Edwards |
| 6,165,173 | A | 12/2000 | Kamdar et al. |
| 6,179,803 | B1 | 1/2001 | Edwards et al. |
| 6,210,355 | B1 | 4/2001 | Edwards et al. |
| 6,228,079 | B1 | 5/2001 | Koenig |
| 6,231,569 | B1 | 5/2001 | Bek et al. |
| 6,293,941 | B1 | 9/2001 | Strul |
| 6,309,386 | B1 | 10/2001 | Bek |
| 6,371,926 | B1 | 4/2002 | Thorson et al. |
| 6,383,181 | B1 | 5/2002 | Johnston et al. |
| 6,391,028 | B1 | 5/2002 | Fanton et al. |
| 6,416,491 | B1 | 7/2002 | Edwards et al. |
| 6,425,151 | B2 | 7/2002 | Barnett |
| 6,431,174 | B1 | 8/2002 | Knudson et al. |
| 6,451,013 | B1 | 9/2002 | Bays et al. |
| 6,551,310 | B1 | 4/2003 | Ganz et al. |
| 6,562,036 | B1 | 5/2003 | Ellman et al. |
| 6,575,969 | B1 | 6/2003 | Rittman, III et al. |
| 6,589,235 | B2 | 7/2003 | Wong et al. |
| 6,659,106 | B1 | 12/2003 | Hovda et al. |
| 6,911,027 | B1 | 6/2005 | Edwards et al. |
| 6,978,781 | B1 | 12/2005 | Jordan |
| 7,055,523 | B1 | 6/2006 | Brown |
| 7,114,495 | B2 | 10/2006 | Lockwood |
| 7,322,993 | B2 | 1/2008 | Metzger et al. |
| 7,416,550 | B2 | 8/2008 | Protsenko et al. |
| 7,442,191 | B2 | 10/2008 | Hovda et al. |
| 7,780,730 | B2 | 8/2010 | Saidi |
| 7,824,394 | B2 | 11/2010 | Manstein |
| 7,850,683 | B2 | 12/2010 | Elkins et al. |
| 8,137,345 | B2 | 3/2012 | McNall et al. |
| 8,317,781 | B2 | 11/2012 | Owens et al. |
| 8,936,594 | B2 | 1/2015 | Wolf et al. |
| 8,986,301 | B2 | 3/2015 | Wolf et al. |
| 9,072,597 | B2 | 7/2015 | Wolf et al. |
| 9,179,964 | B2 | 11/2015 | Wolf et al. |
| 9,179,967 | B2 | 11/2015 | Wolf |
| 9,237,924 | B2 | 1/2016 | Wolf et al. |
| 2002/0016588 | A1 | 2/2002 | Wong et al. |
| 2002/0128641 | A1 | 9/2002 | Underwood et al. |
| 2003/0144659 | A1 | 7/2003 | Edwards |
| 2003/0208194 | A1 | 11/2003 | Hovda et al. |
| 2003/0225403 | A1 | 12/2003 | Woloszko et al. |
| 2005/0119643 | A1 | 6/2005 | Sobol et al. |
| 2005/0222565 | A1 | 10/2005 | Manstein |
| 2006/0235377 | A1 | 10/2006 | Earley |
| 2006/0253117 | A1 | 11/2006 | Hovda et al. |
| 2006/0276817 | A1 | 12/2006 | Vassallo et al. |
| 2007/0066944 | A1 | 3/2007 | Nyte |
| 2007/0219600 | A1 | 9/2007 | Gertner et al. |
| 2008/0027480 | A1 | 1/2008 | Van Der Burg et al. |
| 2008/0082090 | A1 | 4/2008 | Manstein |
| 2009/0018485 | A1 | 1/2009 | Krespi et al. |
| 2009/0143821 | A1 | 6/2009 | Stupak |
| 2009/0292358 | A1 | 11/2009 | Saidi |
| 2010/0144996 | A1 | 6/2010 | Kennedy et al. |
| 2010/0152730 | A1 | 6/2010 | Makower |
| 2011/0009737 | A1 | 1/2011 | Manstein |
| 2011/0282268 | A1 | 11/2011 | Baker |
| 2012/0039954 | A1 | 2/2012 | Cupit et al. |
| 2012/0078377 | A1 | 3/2012 | Gonzales |
| 2012/0316557 | A1 | 12/2012 | Sartor et al. |
| 2012/0323227 | A1 | 12/2012 | Wolf et al. |
| 2012/0323232 | A1 | 12/2012 | Wolf et al. |
| 2013/0218158 | A1 | 8/2013 | Danek et al. |
| 2014/0088463 | A1 | 3/2014 | Wolf et al. |
| 2014/0114233 | A1 | 4/2014 | Deem et al. |
| 2015/0202003 | A1 | 7/2015 | Wolf et al. |

FOREIGN PATENT DOCUMENTS

| | | |
|---|---|---|
| WO | 2007/134005 | 11/2007 |
| WO | 2015-047863 | 4/2015 |
| WO | 2015-048806 | 4/2015 |

OTHER PUBLICATIONS

Written Opinion of the International Searching Authority, Issued by the International Searching Authority for corresponding PCT Application No. PCT/US2014/054726, (Dec. 23, 2014) pp. 1-3.

International Search Report, Issued by the International Searching Authority for corresponding PCT Patent Application No. PCT/US15/023742, (Jun. 29, 2015) pp. 1-2.

Written Opinion, Issued by the International Searching Authority for corresponding PCT Patent Application No. PCT/US15/023742, (Jun. 29, 2015) pp. 1-3.

Cole, Philip, "Biophysics of Nasal Airflow: A Review", American Journal of Rhinology, vol. 14, No. 4, Jul.-Aug. 2000, 245-249.

Cole, Philip, "The Four Components of the Nasal Valve", American Journal of Rhinology, vol. 17, No. 2, Mar.-Apr. 2003, 107-110.

Kjaergaard, Thomas et al., "Relation of Nasal Air Flow to Nasal Cavity Dimensions", Arch Otolaryngol Head Neck Surg., vol. 135, No. 6, Jun. 2009, 565-570.

Stupak, Howard D., "A Perspective on the Nasal Valve", Power Point Presentation, Department of Otorhinolaryngology, Albert Einstein College of Medicine, Nov. 6, 2009, 1-9.

Stupak, Howard D., "Endonasal Repositioning of the Upper Lateral Cartilage and the Internal Nasal Valve", Annals of Otology, Rhinology & Laryngology, Annals Publishing Company, vol. 120(2), 2011, 88-94.

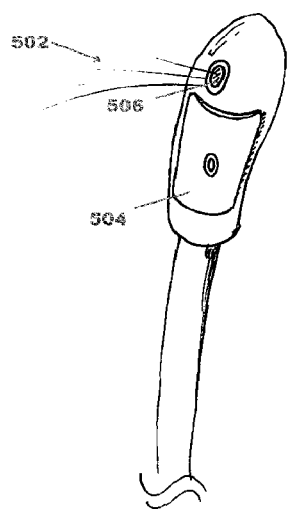
FIG. 19A
FIG. 19B
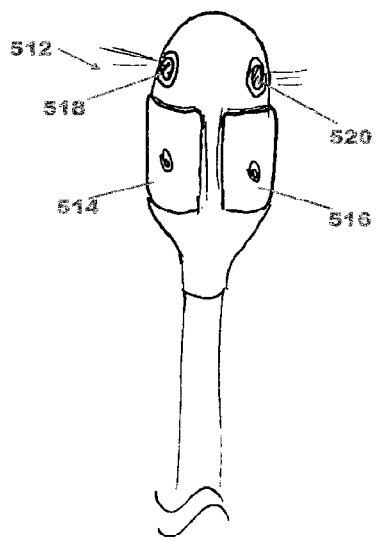
FIG. 20A
FIG. 20B

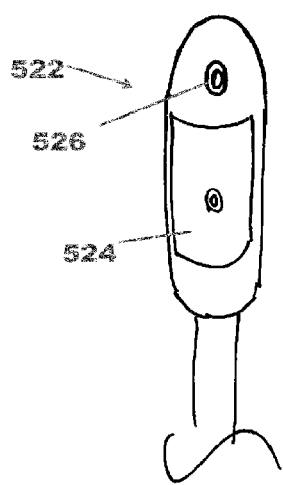 
FIG. 21A   FIG. 21B

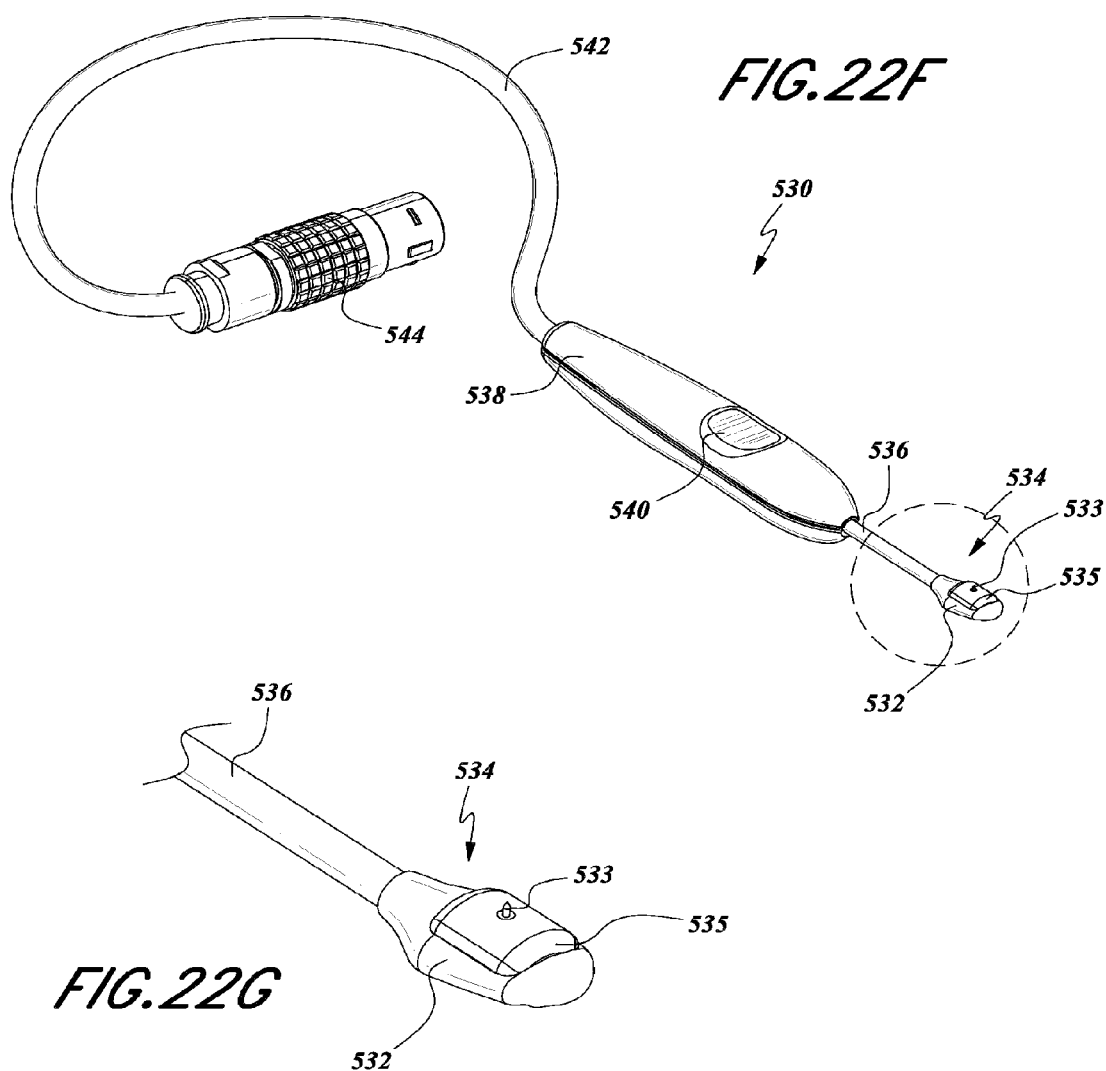

METHODS AND DEVICES TO TREAT NASAL AIRWAYS

CROSS-REFERENCE TO RELATED APPLICATIONS

This application is a continuation of U.S. patent application Ser. No. 13/495,844, now U.S. Pat. No. 8,936,564, entitled METHODS AND DEVICES TO TREAT NASAL AIRWAYS, filed Jun. 13, 2012, which claims priority to U.S. Provisional Patent Application Ser. No. 61/603,864, filed on Feb. 27, 2012, and U.S. Provisional Patent Application Ser. No. 61/496,930, filed on Jun. 14, 2011. The disclosures of all the above-referenced patent applications are hereby incorporated by reference in their entireties herein.

This application is related to Applicant's U.S. applications entitled METHODS AND DEVICES TO TREAT NASAL AIRWAYS, U.S. application Ser. No. 14/319,087, now U.S. Pat. No. 9,072,597, filed Jun. 30 2014; U.S. application Ser. No. 14/026,922, now U.S. Pat. No. 8,986,301, filed Sep. 13, 2013; and U.S. application Ser. No. 13/495,879, now U.S. Pat. No. 9,237,924, filed Jun. 13, 2012, the entireties of which are hereby incorporated by reference in their entireties herein.

BACKGROUND

This application relates generally to the field of medical devices and treatments, and in particular to systems, devices and methods for treating structures within the nose and upper airway to reduce resistance to airflow and/or change the pressure level in the nose, nasal cavities, and/or and nasal passages and improve airflow and/or the feeling and effects of nasal obstruction during breathing.

DESCRIPTION OF THE RELATED ART

During respiration, the anatomy, shape, tissue composition and properties of the human airway produce airflow resistance. The nose is responsible for almost two thirds of this resistance. Most of this resistance occurs in the anterior part of the nose, known as the internal nasal valve, which acts as a flow limiter. The external nasal valve structure also causes resistance to nasal airflow. Effective physiological normal respiration occurs within a range of airflow resistance. However, excessive resistance to airflow can result in abnormalities of respiration, which can significantly affect a patient's quality of life.

Inadequate nasal airflow can result from a number of conditions causing an inadequate cross sectional area of the nasal airway in the absence of any collapse or movement of the cartilages and soft tissues of the nasal airway. These include deviation of the nasal septum, turbinate enlargement, mucosal swelling, excessive mucous production, and nasal valve insufficiency, narrowing or collapse. No matter what the cause of inadequate nasal airflow, the nasal valve area is still a site of significant nasal airflow resistance. Increased nasal valve resistance can be due to static narrowing or movement or collapse of the nasal valve area often due to weakness or malformation of cartilage structures of the nose. In more extreme cases, nasal valve dysfunction is a serious medical condition.

Cartilage is an avascular tissue composed of a specialized matrix of collagens, proteoglycans, and non-collagen proteins, in which chondrocytes constitute the unique cellular component. Cartilage is specialized connective tissue found in various locations throughout the body. Cartilage basically consists of two components: water and a framework of structural macromolecules (matrix) that give the tissue its form and function. The matrix is highly organized and composed of collagens, proteoglycans and noncollagenous proteins.

The interaction of water and the macromolecular framework give the tissue its mechanical properties and thus its function. Up to 65%-80% of the wet weight of cartilage consists of water, while the rest is matrix, mainly collagens and proteoglycans. Chondrocytes are specialized cells that produce and maintain the extracellular matrix (ECM) of cartilage. The ECM makes up most of the tissue, where dense, covalently-linked heterotypic collagen fibrils interact with a number of other specialized matrix components.

The nasal valve was originally described by Mink in 1903. It is divided into external and internal portions. The external nasal valve is the external nasal opening formed by the columella at the base of the septum, the nasal floor, and the nasal rim (the lower region of the nasal wall, also known as the caudal border of the lower lateral cartilage). The nasalis muscle dilates the external nasal valve portion during inspiration.

The internal nasal valve, which accounts for the larger part of the nasal resistance, is located in the area of transition between the skin and respiratory epithelium. The internal nasal valve area is formed by the nasal septum, the caudal border of the upper lateral cartilage (ULC), the head of the inferior turbinate, and the pyriform aperture and the tissues that surround it.

The angle formed between the caudal border of the ULC and the nasal septum is normally between about 10 degrees-15 degrees as illustrated in FIG. 1. The internal nasal valve is usually the narrowest part of the nasal airway and is responsible for more than two thirds of the resistance produced by the nose.

In 1894, Franke performed nasal-flow experiments in models and cadavers and found that whirl formation occurred near the head of the turbinate during calm breathing. Mink in 1903 developed this concept further in 1920, suggesting that the greatest area of resistance was in the limen nasi or the union of the lobular cartilage and ULCs. In 1940, Uddstromer found that 70% of the resistance of the nose was produced in the internal nasal valve area and the remaining 30% was due to the nasal fossa. Van Dishoeck further investigated the mechanisms of the nasal valve in 1942, and in 1970, Bridger and Proctor wrote about a "flow-limiting segment" that included the limen nasi and the pyriform aperture. In 1972, Bachman and Legler found the pyriform aperture to have the smallest cross-sectional area of the nasal airway. In 1983, Haight and Cole continued the study of Bridger and Proctor and demonstrated that the maximal nasal resistance was localized near the pyriform aperture and depended on engorgement of the head of the inferior turbinate. A description of the nasal valve and its functions are more fully described in Cole, "The Four Components of the Nasal Valve", American Journal of Rhinology, Vol. 17, No. 2, pp. 107-110 (2003). See also, Cole, "Biophysics of Nasal Air Flow: A Review", American Journal of Rhinology, Vol. 14, No. 4, pp. 245-249 (2000).

Because ventilation involves pressure changes, the nasal airways must be stable both at rest and under the negative pressures created during quiet and forced inspiration. Proper airflow through the nasal airway depends on satisfactory structural stability (and/or resistance to conformational change resulting from pressure changes) of the upper and lower lateral cartilages and soft tissues respectively. Satisfactory skeletal stability is present when the upper and lower lateral cartilages have sufficient structural stability to resist conformational changes resulting from air pressure changes. When either the skeletal or the soft tissue component is congenitally deficient or has been compromised by surgery or trauma, the patient experiences a conformation change of the valves during inspiration, with resultant change in the airflow and/or pressure in the nasal airway. Normally, the upper lateral cartilages move, change shape, partially collapse and/or change nasal airway pressure with all ventilatory flow rates. Thus, even normal nasal valves are affected by respiration. However, a patient with dynamic nasal valve dysfunction may have a nasal airway walls that inadequately resist the pressure changes and restrict airflow even during normal nasal breathing.

Inadequate nasal valve structural strength, stiffness or conformation can be a consequence of previous surgery, trauma, aging, or primary weakness of the upper lateral cartilage and is often symptomatic and debilitating. As many as 13% of the patients with chronic nasal obstruction have some degree of nasal valve collapse. Of these patients, 88% have unilateral collapse.

Poor nasal breathing and/or nasal congestion has profound effects on a person's health and quality of life, which can be measured by validated questionnaires such as the NOSE score, as described in Stewart M G, Witsell D L, Smith T L, Weaver E M, Yueh B, Hannley M T. Development and validation of the Nasal Obstruction Symptom Evaluation (NOSE) scale. Otolaryngol Head Neck Surg 2004; 130:157-63.

Causes of inadequate nasal airflow and the structure of the nasal valve inadequacy can be clinically detected by direct visualization (preferably with minimal disturbance so as not to alter the structure by visualizing) or endoscopic examination. Alternatively, CT, MRI, ultrasound or other non-invasive imaging technologies may be employed. One method of evaluating the potential improvement in nasal airflow from widening the nasal valve area nasal valve obstruction is the cottle test, which involves gently pulling the skin of a patient's cheek laterally away from the nose with two fingers, thereby opening the internal nasal valve.

Existing methods of correcting nasal valve inadequacy include surgically repositioning the upper lateral cartilage or adding structural grafts to support the lateral wall of the nose. Surgical structural enhancement of the valve can include the use of cartilage grafts and grafts made from a number of materials. The most frequent methods surgically correct internal nasal valve collapse and involve the use of spreader grafts placed between the upper lateral cartilage and septum. Alternately, stents, spreaders or other devices may be implanted to reposition the ULC. Invasive surgical and implant solutions carry substantial risk and discomfort.

External (non-implanted) nasal dilators which are placed temporarily and removed by the patient are also available. Such external devices are possibly placed on the outside surface of the nose such as the "Breathe Right" strips as shown for example in U.S. Pat. No. 5,533,499 to Johnson or similar devices taught by U.S. Pat. No. 7,114,495 to Lockwood. Other devices may be temporarily placed in the nasal cavity (but not implanted in the nose), such as those taught in U.S. Pat. No. 7,055,523 to Brown, and U.S. Pat. No. 6,978,781 to Jordan. However, such devices can be uncomfortable, unsightly, and require the patient to remove and replace the device on a periodic basis. These devices can cause skin irritation.

Poor nasal airflow can also occur in people with a structurally normal nasal and/or nasal valve anatomy, as well as a normal nasal passage cross-sectional area. The strength, structure and resistance to collapse of the nasal passage can also be normal in people with poor nasal airflow. People can have poor nasal airflow from other causes, including deviated septum, allergic rhinitis, non-allergic rhinitis, turbinate hyperplasia, nasal tip ptosis, and nasal polyposis. Whatever the cause, the tissues of the nasal valves are intimately involved in nasal airflow and nasal airflow inadequacy. Thus, there remains an unmet need in the art for non-invasive and minimally invasive methods and devices to improve nasal airflow.

SUMMARY

Embodiments of the present application are directed to devices, systems and methods for treating nasal airways. Such embodiments may be utilized to improve breathing by decreasing airflow resistance and/or improving nasal airflow or perceived airflow resistance in the nasal airways. For example, the devices, systems and methods described herein may be utilized to reshape, remodel, strengthen, or change the properties of the tissues of the nose, including, but not limited to the skin, muscle, mucosa, submucosa and cartilage in the area of the nasal valves.

According to one aspect, a device for treating a patient's nasal airway is provided. In one embodiment, the device comprises an energy delivery element sized to be inserted into a nose or to be delivered external to a nose. The energy delivery element is configured to deliver energy to tissues within the nose and to reshape a region of the nose to a new conformation.

According to one embodiment, a device for treating a patient's nasal airway comprises an elongate shaft having a proximal end and a distal end. The device further comprises a handle at the proximal end of the elongate shaft. The device also comprises a treatment element at the distal end of the elongate shaft. The treatment element is sized to be inserted into the nasal airway or to be delivered external to a nose. The treatment element is configured to reshape a region of the nose to a new conformation and comprises an electrode configured to deliver radiofrequency (RF) energy to the nasal tissue.

Other embodiments of devices for treating a patient's nasal airway include devices that apply other types of treatment. For example, a treatment device may apply energy in the form selected from the group consisting of ultrasound, quantic molecular resonance, microwave, heat, cold, radiofrequency, electrical, light and laser. The treatment device may also be configured to inject a polymerizing liquid or to deliver a cauterizing agent to nasal tissue. Other embodiments are described below.

The devices described herein may be configured to be positioned internally within the nose, external to the nose, or both. Certain embodiments are configured to be delivered into one nostril, and other embodiments are configured to be delivered into both nostrils. In some embodiments the device may comprise a reshaping element having a shape configured to alter a conformation of a region of the nose to a new conformation. For embodiments utilizing an energy delivery element, the reshaping element may be a separate element from the energy delivery element, or the energy delivery element and the reshaping element may be part of the same element. The energy delivery element and/or reshaping element in one embodiment may have a convex shape to create a concavity in nasal tissue.

In embodiments utilizing energy delivery, a handle may be provided comprising a button or other input control to active one or more electrodes. Electrodes may comprise one or more monopolar needles, one or more monopolar plates, or one or more bipolar electrode pairs (which may also comprise one or more needles or plates). These electrodes may be located in various locations, for example, inside the nasal passageway, external to the nose or both. For example, when using bipolar electrode pairs, a first electrode surface may be positioned internal to the nose and a second electrode surface may be positioned external to the nose, so that the two electrode surfaces are positioned on opposite sides of nasal tissue.

Furthermore, in embodiments utilizing energy delivery, the reshaping element may incorporate features designed to assist location of the device in the nose as well as protection of tissue around the treatment area.

The device of one energy delivery embodiment may comprise an adaptor configured to be connected to an energy source, such as an RF energy source. The device may also comprise a control system configured to control the characteristics of energy applied to tissue. A thermocouple or other sensor may be provided to measure a temperature near tissue or other tissue or device parameter.

In another aspect, a system is provided comprising a device as described above and further below in combination with one or more other components. One such component may be an energy source, such as an RF energy source. Another component may be a control system for controlling the energy source and/or treatment device. In another embodiment, the device or system may comprise a cooling mechanism to cool desired tissue locations while treatment is being applied. In monopolar electrode embodiments, a grounding pad may also be provided as part of the system. Another system includes a positioning device that may be used pre-treatment to determine the optimal device and positioning and/or other parameters for using the device to be treat to the nasal airway.

According to another aspect, a method of treating a patient's nasal airway is provided. In one embodiment, the method comprises alerting a structure, shape or conformation of one or more nasal structures in an area of a nasal valve by applying a treatment sufficient to modify, by reshaping, tissue at or adjacent to the nasal valve.

According to one embodiment, a method of treating a patient's nasal airway comprises positioning a treatment element within the nasal airway adjacent to nasal tissue to be treated. The treatment element comprises one or more electrodes, such as described above and in further detail below. The method further comprises deforming the nasal tissue into a desired shape by pressing a surface of the treatment element against the nasal tissue to be treated. The method further comprises delivering radiofrequency (RF) energy to the one or more electrodes to locally heat the nasal tissue, wherein delivering RF energy while deforming the nasal tissue causes the nasal tissue to change shape. The method also comprises removing the treatment element from the nasal airway.

The methods, devices and systems described herein may be used to reshape tissue without a surgical incision or implant. In certain embodiments, the reshaping of tissue may be accomplished by ablating tissue. In other embodiments, the reshaping of tissue is accomplished without ablation of tissue. In one embodiment, a treatment element is positioned within a nasal passageway. The treatment element may be used to simultaneously mechanically alter the shape of the internal or external nasal valve and apply treatment to tissue of the nose. The treatment applied may comprise modifying a nasal structure in a manner that increases a volumetric airflow rate of air flowing from an exterior of the patient's body into the patient's nasopharynx without changing a shape of an internal nasal valve, said modifying comprising modifying a mechanical property of at least one nasal valve. A positioning element may be used to determine a desired position of a treatment element before the treatment element is delivered to the nasal tissue.

The treatment may involve delivering energy in the form selected from the group selected from the group consisting of ultrasound, microwave, heat, radiofrequency, electrical, light and laser. The nasal tissue to be treated may be cooled prior to, during or after delivering energy. Delivering energy may comprise measuring a temperature near nasal tissue to be treated, and adjusting a level of energy delivered to the tissue. When RF or other types of energy are used, the energy may be delivered to at least one of the nasal valve, tissue near the nasal valve, or the upper lateral cartilage of tissue. For example, RF energy or other energy may be delivered to the one or more electrodes for about 15 seconds to about 1 minute. RF energy or other energy may be delivered to heat an area of tissue to a temperature of about 50 degrees C. to about 70 degrees C.

Other methods not utilizing energy delivery include injecting a polymerizing liquid, delivering a cauterizing agent, or other embodiments described below.

Energy or treatment may be delivered for a sufficient period of time or in a sufficient quantity to cause a desired effect. For example, the treatment may cause stress relaxation in the nasal tissue without weakening the tissue. The treatment may also be applied to injure a tissue to be re-shaped.

BRIEF DESCRIPTION OF DRAWINGS

Certain preferred embodiments and modifications thereof will become apparent to those skilled in the art from the detailed description below having reference to the figures that follow.

FIGS. 19A and 19B illustrate an embodiment of a device for applying energy to the nasal valve area configured for use in only one nostril.

FIGS. 20A and 20B illustrate an embodiment of a device for applying energy to the nasal valve area configured for use in either nostril.

FIGS. 21A and 21B illustrate an embodiment of a device for applying energy to the nasal valve area having a symmetrical shape.

FIGS. 22A-22G illustrate an embodiment of a device for applying energy to the nasal valve area using a monopolar electrode.

DETAILED DESCRIPTION

Figure 1:
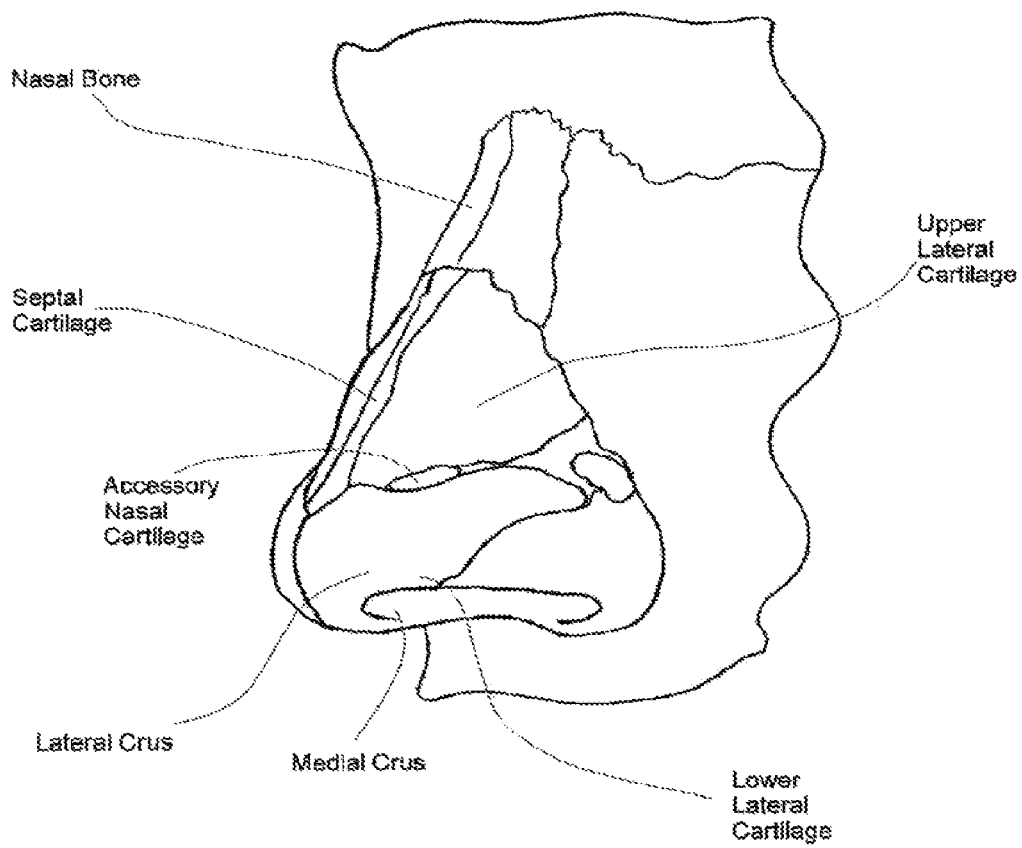
FIG. 1 depicts an illustration of bone and cartilage structures of a human nose.

The following disclosure provides embodiments of systems and methods for improving breathing by decreasing airflow resistance or perceived airflow resistance at or near a site of an internal or external nasal valve. Such embodiments may include methods and devices for reshaping, remodeling, strengthening, or changing the properties of the tissues of the nose, including, but not limited to the skin, muscle, mucosa, submucosa, and cartilage in the area of the nasal valves.

While, in some instances, nasal dysfunction can lead to poor airflow, nasal breathing can also be improved in people with normal breathing and/or normal nasal anatomy by decreasing nasal airflow resistance in the nasal valve and associated nasal anatomy. Remodeling or changing the structure of the nasal valve can improve nasal airflow in people with inadequate nasal airflow resulting from causes other than nasal valve dysfunction, such as deviated septum, enlarged turbinates, mucosal swelling, and/or mucous production. The methods and devices described above are generally invasive methods or unsightly devices that a person with normal breathing and/or anatomy may not necessarily be inclined to use or undergo. Thus, there remains an unmet need in the art for non-invasive and minimally invasive methods and devices to decrease nasal airflow resistance or perceived nasal airflow resistance and/or to improve nasal airflow or perceived nasal airflow and the resulting symptoms or sequella of poor nasal airflow including but not limited to snoring, sleep disordered breathing, perceived nasal congestion and poor quality of life through the change of structures within the nose that form the passageways for airflow. Methods and devices described herein may be used to treat nasal airways without the need for more invasive procedures (e.g., ablation, surgery).

Nasal breathing can be improved in people with normal breathing and/or normal nasal anatomy by decreasing nasal airflow resistance or perceived nasal airflow resistance in the nasal valve and associated nasal anatomy. Restructuring the shape, conformation, angle, strength, and cross sectional area of the nasal valve may improve nasal airflow. Changing the nasal valve can be performed alone or together with other procedures (e.g., surgical procedures), such as those described above. Such methods and devices can lead to improved nasal airflow, increased volume of nasal airflow in patients with normal or reduced nasal airflow.

The internal nasal valve area is the narrowest portion of the nasal passage and thus functions as the primary regulator of airflow and resistance. The cross-sectional area of the internal nasal valve area is normally about 55-83 mm.sup.2. As described by the Poiseuille law, airflow through the nose is proportional to the fourth power of the radius of the narrowest portion of the nasal passageway. Thus, changes as small as 1 mm in the size of the nasal valve have an exponential effect on airflow and resistance through the nasal cavity and the entire respiratory system.

FIGS. 1 and 2A-C illustrate anatomical elements of a human nose. The lower lateral cartilage (LLC) includes an external component referred to as the lateral crus and an internal component referred to as the medial crus. The medial crus and septal nasal cartilage create a nasal septum that separates the left and right nostrils. Upper lateral cartilage lies between the lower lateral cartilages and the nasal bone. The left ULC is separated from the right ULC by the septal cartilage extending down the bridge of the nose. The opposing edges of the LLC and ULC may move relative to one another. Disposed between the opposing edges is an accessory nasal cartilage. The septal nasal cartilage and the ULC form an angle (.THETA.) called the nasal valve angle.

Figure 2A:
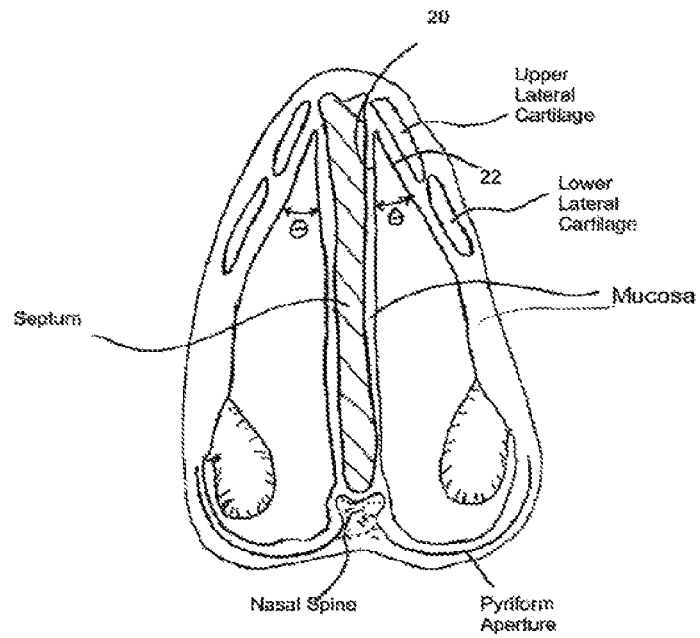
FIG. 2A illustrates a cross-sectional view illustrating tissues and structures of a human nose.
Figure 2B:
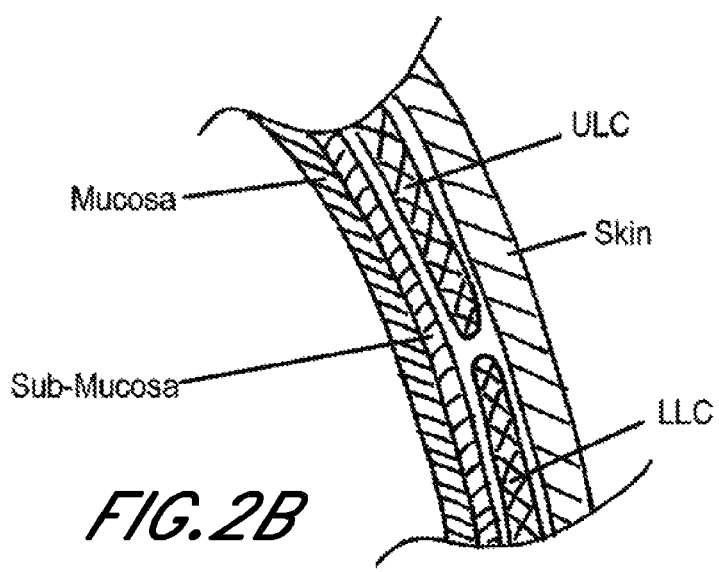
FIG. 2B shows a detailed cross-sectional view illustrating a detailed section of the structures of FIG. 2A.

FIG. 2B illustrates a detailed cross-section of a segment of nose tissue in the area of the intersection of the ULC and the LLC. As shown in the detailed view of FIG. 2A, both inner and outer surfaces of the nasal cartilage are covered with soft tissue including mucosa, sub-mucosa and skin.

Figure 2C:
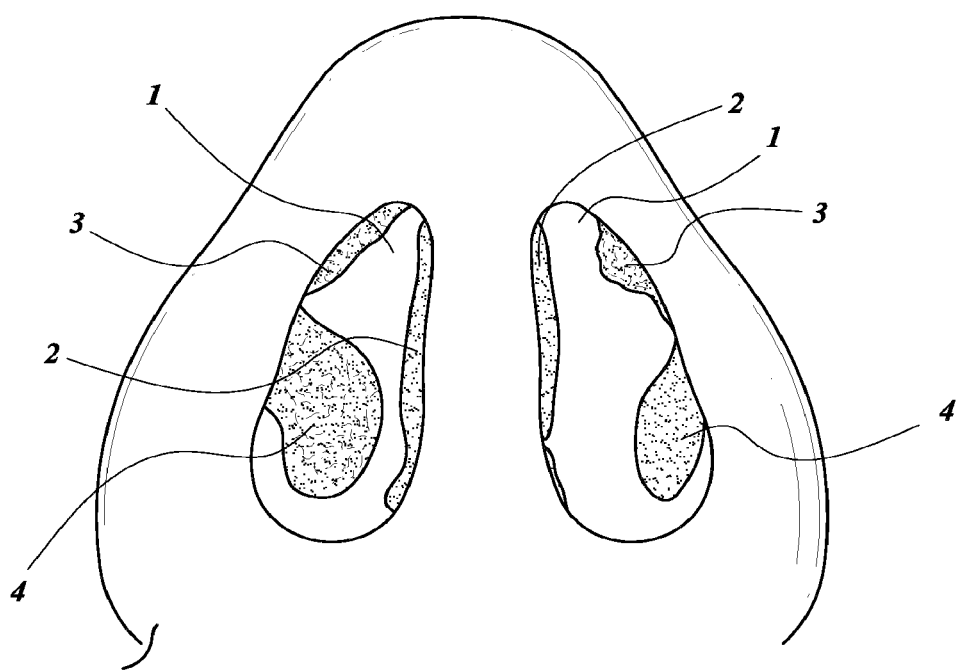
FIG. 2C illustrates a view of the nostrils illustrating tissues and structures of a human nose.

FIG. 2C illustrates a view of the nose as seen from the nostrils. FIG. 2 depicts the nasal valve 1 shown between the septum 2 and the Upper Lateral Cartilage 3. FIG. 2A also depicts the position of the turbinate 4.

The internal nasal valve area of the nasal airway passage can be visualized prior to and/or during any treatment by any suitable method, including but not limited to direct visualization, endoscopic visualization, visualization by the use of a speculum, transillumination, ultrasound, MRI, x-ray or any other method. In some embodiments, treatments of the nasal valve area as described herein may be performed in conjunction with or following another procedure (e.g., a surgical procedure such as surgically repairing a deviated septum). In such embodiments, the nasal valve area may be visualized and accessed during surgery. In some embodiments, it may be desirable to visualize the internal nasal valve with minimum disturbance, so as to avoid incorrect assessments due to altering the shape of the nasal valve during visualization. In some embodiments, visualization elements may be incorporated into or combined with treatment devices configured for treating internal and/or external nasal valves.

Airflow through the nasal passage can be measured prior to and/or during any treatment by any suitable method, including, but not limited to, a nasal cannula connected to a pressure measurement system, rhinomanometry, and rhinohygrometer. Nasal airflow and resistance can also be evaluated by subjective evaluation before and after a manipulation to increase the cross-sectional area of the nasal passage, such as the Cottle maneuver. In some embodiments, it may be desirable to measure nasal airflow and/or resistance prior to, during and/or after a procedure.

The internal nasal valve area of the nasal airway passage can be accessed through the nares. In some embodiments, one or more devices may be used to pull the tip of the nose caudally and increase the diameter of the nares in order to further facilitate access to the internal nasal valve for treatment. Such devices may include speculum type devices and retractors. In other embodiments, access to the internal nasal valve may also be achieved endoscopically via the nares, or via the mouth and throat. In some embodiments, visualization devices may be incorporated or combined with treatment devices for treating internal and/or external nasal valves. These and any other access and/or visualization devices may be used with any of the methods and devices below.

During inhalation, airflow through the nostrils creates an inward pressure at the junction between the upper and lower cartilages. This pressure may be expressed as a function of nasal resistance which may be estimated as 10 centimeters of water per one liter per second in congested patients (see "The Four Components of the Nasal Valve" by Cole, published in the American Journal of Rhinology, pages 107-110, 2003). In response to these low pressures relative to the environment outside the nose, a normal, weakened and/or structurally inadequate nasal valve may move inwardly with the junction between the upper and lower cartilages acting as a hinge point for the inward deflection. Furthermore, a small increase in area through which air flows can greatly decrease the pressure differential in these structures resulting in less inward movement of the internal nasal valve structures. Increasing the cross sectional area of the nasal valve area thus has the beneficial effects of decreasing nasal airflow resistance and decreasing the amount and likelihood of inward movement of the nasal valve structures during inspiration.

Some embodiments below provide apparatus and methods for increasing the area of the opening at the nasal valve and/or treating nasal valve insufficiency by modifying the structure and/or structural properties of tissues at or adjacent to the internal and/or external nasal valve. Other embodiments below provide apparatus and methods for treating nasal valve insufficiency and/or increasing the area of the opening at nasal valve by re-shaping structures within and/or adjacent to an internal and/or external nasal valve to achieve a more optimum shape and minimize or remove airflow obstructions. Still other embodiments combine the two approaches of re-shaping and modifying tissue and structures of and adjacent to the internal and/or external nasal valves. Still other embodiments provide apparatus and methods for increasing the area of the opening at the nasal valve and treating nasal obstruction resulting from causes other than nasal valve restriction or insufficiency by improving the structure or function of the nasal valve tissue to increase airflow. Still other embodiments below provide apparatus and methods for decreasing airflow resistance in a structurally normal nasal valve and/or increasing the area of the opening at nasal valve by re-shaping structures within and/or adjacent to an internal and/or external nasal valve to achieve a more optimum shape and minimize or remove airflow obstructions. For example, patients having a normal nasal valve anatomy may still benefit from the devices and treatments described herein, as improvement in the nasal valve structure and/or increasing the area of the opening at the nasal valve may improve breathing problems caused by other conditions. Still other embodiments provide for structural changes in the nasal cavity and airway that improve the relative positions of the structures of the nasal cavity to improve nasal breathing.

In some embodiments, airflow restrictions to the internal nasal valve may be the result of a smaller-than-optimal internal nasal valve angle, shown as .theta. in FIG. 2. An internal nasal valve angle (i.e. the angle formed between the caudal border of the ULC and the nasal septum) of less than the normally optimal range of between about 10.degree.-15.degree. can result in airflow restrictions. Thus, in some embodiments, treatments may be designed to re-shape structures at or adjacent to the internal nasal valve in order to increase the internal nasal valve angle sufficiently that after such treatments, the nasal valve angle falls within the optimal range of 10-15 degrees. In some embodiments, the internal valve angle may also be increased to be greater than 15 degrees.

In some embodiments, airflow restrictions to the internal nasal valve may be the result of a smaller-than-optimal area of the internal nasal valve. An internal nasal valve with a less than optimal area can result in airflow restrictions. Thus, in some embodiments, treatments may be designed to re-shape structures at or adjacent to the internal nasal valve in order to increase the internal nasal valve angle sufficiently that after such treatments, the area of the nasal valve falls within an optimal range. In some embodiments, increasing the area of the opening at the nasal valve without increasing the angle of the nasal valve may improve airflow. In some embodiments, increasing the angle of the nasal valve without increasing the area of the opening at the nasal valve may improve airflow. In some embodiments, both the opening at the area of the nasal valve and the angle of the nasal valve may be increased to improve airflow.

In some embodiments, nasal airflow can be increased in the presence of normal nasal valve anatomy and/or normal or enlarged nasal valve angle or area.

With reference to FIG. 2A, in some embodiments, the internal valve angle .theta. or area may be increased by mechanically pressing laterally outwards against the internal lateral nasal wall. In some embodiments, this outward pressing may be performed by an inflatable balloon (such as those discussed below with reference to FIGS. 4A-4B) which may be positioned between the upper portion of the nasal septum 20 and the outer lateral wall 22 and then inflated, pressing against the lateral nasal wall until the nasal valve angle reaches a desired size. Similarly, other mechanical devices such as spreaders or retractors (such as those discussed below with reference to FIGS. 5A & 5B) or molds may be used. In alternative embodiments, short-term removable implants may be used to re-shape the nasal valve. Some examples of short-term implants may include stents, molds or plugs. In further alternative embodiments, external re-shaping elements, such as adhesive strips or face masks may be used to modify the shape of a nasal valve. In some embodiments, energy application or other treatments as described below may be applied to substantially fix the re-shaped tissue in a desired conformational shape before, during or after applying a mechanical re-shaping force (e.g., with the balloon, mechanical devices, molds, short-term implants, or external re-shaping elements described above or any of the mechanical devices described below).

In another embodiment, a re-shaping device may be used to expand the diameter of the nasal passage at the site of the internal or external nasal valve. The expansion device can be a balloon, user controlled mechanical device, self expanding mechanical device, fixed shape device or any combination thereof. The expansion can increase the diameter over the normal range in order for the diameter to remain expanded after removal of the device and healing of the tissue.

In some embodiments, a re-shaping device may be used to conformationally change the structure of the internal or external nasal valve anatomy to allow greater airflow without necessarily expanding the diameter of the nasal passage.

In some embodiments, a re-shaping or remodeling device can be used to conformationally change the structure of areas of the internal nasal valve other than the nasal valve that causes the cross sectional or three dimensional structure of the nasal airway to assume a shape less restrictive to airflow without widening the nasal valve angle.

In some embodiments, the tissue of the internal and/or external nasal valve and/or surrounding tissues may be strengthened or otherwise modified to resist a conformational change in response to the negative pressure of inspiration. In some embodiments, this strengthening may be performed by applying treatments selected to change mechanical or structural properties of the treated tissue. In some embodiments, such treatments may include the application of energy to selected regions of nasal valve and/or surrounding tissues.

In some embodiments, energy may be applied in the form of heat, radiofrequency (RF), laser, light, ultrasound (e.g. high intensity focused ultrasound), microwave energy, electromechanical, mechanical force, cooling, alternating or direct electrical current (DC current), chemical, electrochemical, or others. In alternative embodiments, the nasal valve and/or surrounding tissues may be strengthened through the application of cryogenic therapy, or through the injection or application of bulking agents, glues, polymers, collagen and/or other allogenic or autogenic tissues, or growth agents.

Any one or more of the above energy-application mechanisms may also be used to re-shape, remodel, or change mechanical or physiologic properties of structures of a nasal valve or surrounding tissues. For example, in some embodiments, energy may be applied to a targeted region of tissue adjacent a nasal valve such that the tissue modification results in a tightening, shrinking or enlarging of such targeted tissues resulting in a change of shape. In some such embodiments, re-shaping of a nasal valve section may be achieved by applying energy without necessarily applying a mechanical re-shaping force. For example energy can be used to selectively shrink tissue in specific locations of the nasal airway that will lead to a controlled conformational change.

In alternative embodiments, strengthening and/or conformation change (i.e., re-shaping) of nasal valve tissue to reduce negative pressure during inspiration may include modification of tissue growth and/or the healing and fibrogenic process. For example, in some embodiments energy may be applied to a targeted tissue in the region of the internal nasal valve in such a way that the healing process causes a change to the shape of the nasal valve and/or a change in the structural properties of the tissue. In some embodiments, such targeted energy application and subsequent healing may be further controlled through the use of temporary implants or re-shaping devices (e.g. internal stents or molds, or external adhesive strips).

In some embodiments, energy may be delivered into the cartilage tissue to cause a conformational change and/or a change in the physical properties of the cartilage. Energy delivery may be accomplished by transferring the energy through the tissue covering the cartilage such as the epithelium, mucosa, sub-mucosa, muscle, ligaments, tendon and/or skin. In some embodiments, energy may also be delivered to the cartilage using needles, probes or microneedles that pass through the epithelium, mucosa, submucosa, muscle, ligaments, tendon and/or skin (as illustrated for example in FIG. 4D).

In some embodiments, energy may be delivered into the submucosal tissue to cause a conformational change and/or a change in the physical properties of the submucosal tissue. Energy delivery may be accomplished by transferring the energy through the tissue covering the submucosa such as the epithelium, mucosa, muscle, ligaments, cartilage, tendon and/or skin. In some embodiments, energy may also be delivered to the submucosa using needles, probes, microneedles, micro blades, or other non-round needles that pass through the epithelium, mucosa, muscle, ligaments, tendon and/or skin.

Figure 3:
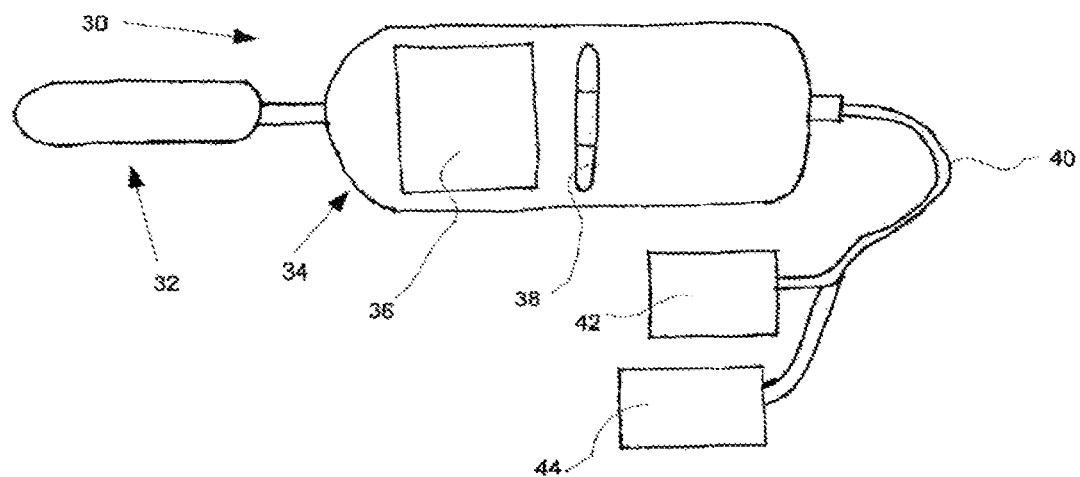
FIG. 3 depicts a schematic illustration of a nasal valve re-shaping treatment device.

FIG. 3 illustrates an embodiment of a nasal valve treatment device 30. The device 30 comprises a treatment element 32 which may be configured to be placed inside the nasal cavity, nasal passage, and/or nasal airway to deliver the desired treatment. In some embodiments, the device 30 may further comprise a handle section 34 which may be sized and configured for easy handheld operation by a clinician. In some embodiments, a display 36 may be provided for displaying information to a clinician during treatment.

In some embodiments, the information provided on the display 36 may include treatment delivery information (e.g. quantitative information describing the energy being delivered to the treatment element) and/or feedback information from sensors within the device and/or within the treatment element. In some embodiments, the display may provide information on physician selected parameters of treatment, including time, power level, temperature, electric impedance, electric current, depth of treatment and/or other selectable parameters.

In some embodiments, the handle section 34 may also comprise input controls 38, such as buttons, knobs, dials, touchpad, joystick, etc. In some embodiments, controls may be incorporated into the display, such as by the use of a touch screen. In further embodiments, controls may be located on an auxiliary device which may be configured to communicate with the treatment device 30 via analog or digital signals sent over a cable 40 or wirelessly, such as via bluetooth, WiFi (or other 802.11 standard wireless protocol), infrared or any other wired or wireless communication method.

In some embodiments the treatment system may comprise an electronic control system 42 configured to control the timing, location, intensity and/or other properties and characteristics of energy or other treatment applied to targeted regions of a nasal passageway. In some embodiments, a control system 42 may be integrally incorporated into the handle section 34. Alternatively, the control system 42 may be located in an external device which may be configured to communicate with electronics within the handle section 34. A control system may include a closed-loop control system having any number of sensors, such as thermocouples, electric resistance or impedance sensors, ultrasound transducers, or any other sensors configured to detect treatment variables or other control parameters.

The treatment system may also comprise a power supply 44. In some embodiments, a power supply may be integrally incorporated within the handle section 34. In alternative embodiments, a power supply 44 may be external to the handle section 34. An external power supply 44 may be configured to deliver power to the handle section 34 and/or the treatment element 32 by a cable or other suitable connection. In some embodiments, a power supply 44 may include a battery or other electrical energy storage or energy generation device. In other embodiments, a power supply may be configured to draw electrical power from a standard wall outlet. In some embodiments, a power supply 44 may also include a system configured for driving a specific energy delivery technology in the treatment element 32. For example, the power supply 44 may be configured to deliver a radio frequency alternating current signal to an RF energy delivery element. Alternatively, the power supply may be configured to deliver a signal suitable for delivering ultrasound or microwave energy via suitable transducers. In further alternative embodiments, the power supply 44 may be configured to deliver a high-temperature or low-temperature fluid (e.g. air, water, steam, saline, or other gas or liquid) to the treatment element 32 by way of a fluid conduit.

In some embodiments, the treatment element 32 may have a substantially rigid or minimally elastic shape sized and shaped such that it substantially conforms to an ideal shape and size of a patient's nasal passageway, including the internal and external nasal valves. In some embodiments, the treatment element 32 may have a curved shape, either concave or convex with respect to the interior of the lateral wall of the nasal passage. In some embodiments, the shape of a fixed-shape treatment element may be substantially in a shape to be imparted to the cartilage or other structures of the internal or external nasal valve area.

Figure 4A:
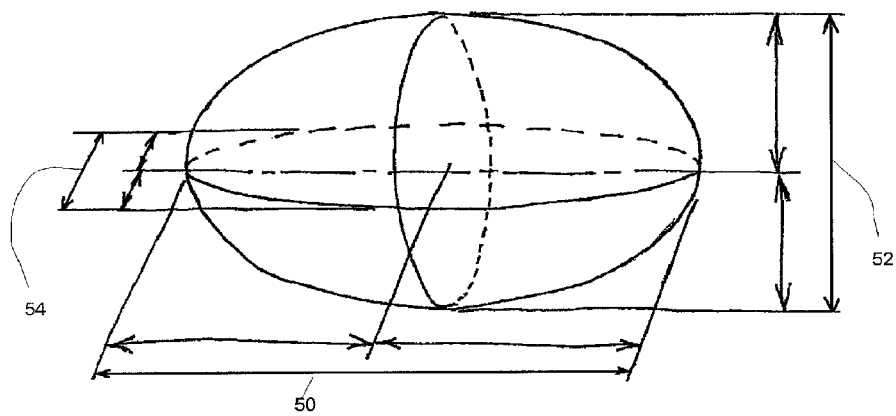
FIG. 4A is a perspective illustration of an embodiment of a treatment element shape.

In some embodiments, as shown for example in FIG. 3, the treatment element 32 may comprise a substantially cylindrical central portion with a semi-spherical or semi-ellipsoid or another shaped end-cap section at proximal and/or distal ends of the treatment element 32. In alternative embodiments, the treatment element may comprise a substantially ellipsoid shape as shown, for example in FIGS. 4A-4D. In some embodiments, an ellipsoid balloon as shown in FIG. 4A may have an asymmetrical shape. In alternative embodiments, the treatment element 32 may have an asymmetrical "egg-shape" with a large-diameter proximal end and a smaller-diameter distal end. In some embodiments, the element 32 can be shaped so as to impart a shape to the tissue treated that is conducive to optimal nasal airflow. Any suitable solid or expandable medical balloon material and construction available to the skilled artisan may be used.

Figure 4B:
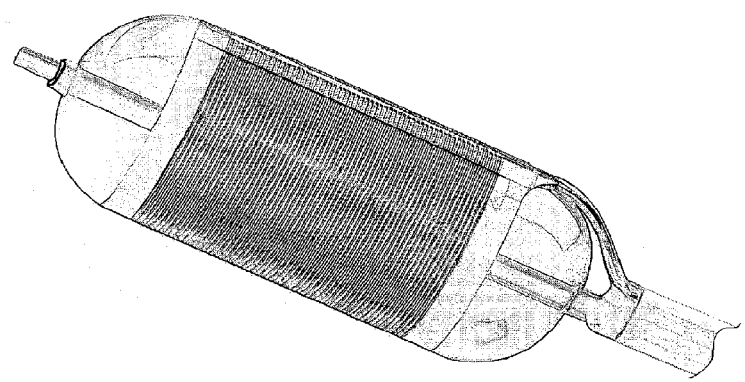
FIG. 4B depicts a perspective illustration of another embodiment of a treatment element shape.

FIG. 4B illustrates an embodiment of a treatment element configured to deliver energy to an interior of a nasal valve. In some embodiments, the treatment element of FIG. 4B also includes an expandable balloon.

Figure 4C:
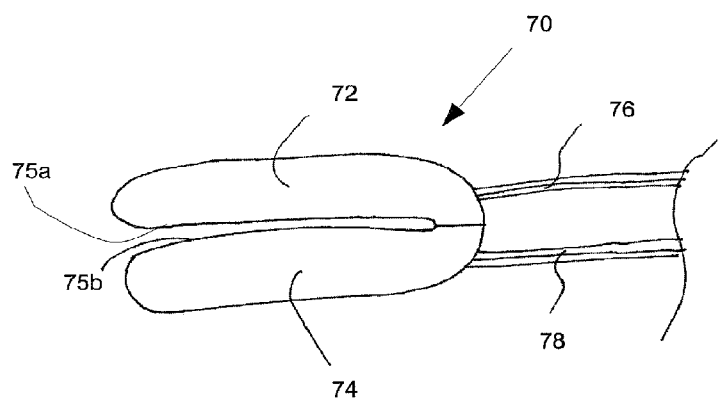
FIG. 4C shows a perspective illustration of another embodiment of a treatment element shape.
Figure 4D:
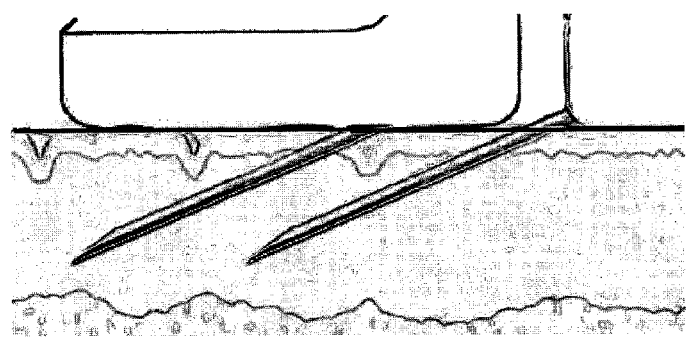
FIG. 4D depicts a cross-sectional view of a treatment device comprising a plurality of microneedles puncturing tissue in order to apply treatment at a desired tissue depth.

FIG. 4C illustrates an embodiment of a bifurcated treatment element 70 having a pair of semi-ellipsoid elements 72, 74 sized and configured to be inserted into the nose with one element 72, 74 on either side of the septum. The elements may each have a medial surface 75a & 75b which may be substantially flat, curved or otherwise shaped and configured to lie adjacent to (and possibly in contact with) the nasal septum. In some embodiments, the elements 72, 74 may include expandable balloons with independent inflation lumens 76, 78. In alternative embodiments, the elements 72, 74 have substantially fixed non-expandable shapes. In still further embodiments, the elements 72, 74 may include substantially self-expandable sections. In some embodiments, the bifurcated treatment element halves 72, 74 may also carry energy delivery structures as described elsewhere herein. In some embodiments, the shape of the elements 72, 74 may be modified by the operator to impart an optimal configuration to the treated tissue. The shape modification of elements 72, 74 can be accomplished pre-procedure or during the procedure and can be either fixed after modification or capable of continuous modification.

In some embodiments, a nasal valve treatment system may also comprise a re-shaping device configured to mechanically alter a shape of soft tissue and/or cartilage in a region of a nasal valve in order to impart a desired shape and mechanical properties to the tissue of the walls of the nasal airway. In some embodiments the re-shaping device may be configured to re-shape the internal and/or external nasal valve into a shape that improves the patency of one or both nasal valve sections at rest and during inspiration and/or expiration. In some embodiments, the reshaping device may comprise balloons, stents, mechanical devices, molds, external nasal strips, spreader forceps or any other suitable structure. In some embodiments, a re-shaping device may be integrally formed with the treatment element 32. In alternative embodiments, a re-shaping device may be provided as a separate device which may be used independently of the treatment element 32. As described in more detail below, such re-shaping may be performed before, during or after treatment of the nose tissue with energy, injectable compositions or cryo-therapy.

With reference to FIGS. 4A-4C, some embodiments of treatment elements 32 may comprise one or more inflatable or expandable sections configured to expand from a collapsed configuration for insertion into the nasal passageway, to an expanded configuration in which some portion of the treatment element 32 contacts and engages an internal surface of a nasal passageway. In some embodiments, an expandable treatment element may comprise an inflation lumen configured to facilitate injection of an inflation medium into an expandable portion of the treatment element. In alternative embodiments, an expandable treatment element may comprise one or more segments comprising a shape-memory alloy material which may be configured to expand to a desired size and shape in response to a change of temperature past a transition temperature. In some embodiments, such a temperature change may be brought about by activating an energy-delivery (or removal) element in the treatment element 32.

In some embodiments, the treatment element 32 may expand with various locations on the element expanding to different configurations or not expanding at all to achieve a desired shape of the treatment element. In some embodiments, such expandable treatment elements or sections may be elastic, inelastic, or pre-shaped. In some embodiments, expandable treatment elements or sections there of may be made from shape-memory metals such as nickel-cobalt or nickel-titanium, shape memory polymers, biodegradable polymers or other metals or polymers. Expandable balloon elements may be made of any elastic or inelastic expandable balloon material.

In alternative embodiments, the treatment element 32 can act to change the properties of the internal soft tissue of the nasal airway in conjunction with an external treatment device of fixed or variable shape to provide additional force to change the shape of the internal and/or external nasal valve. In some embodiments, an external mold element can be combined with an internal element.

Figure 5A:
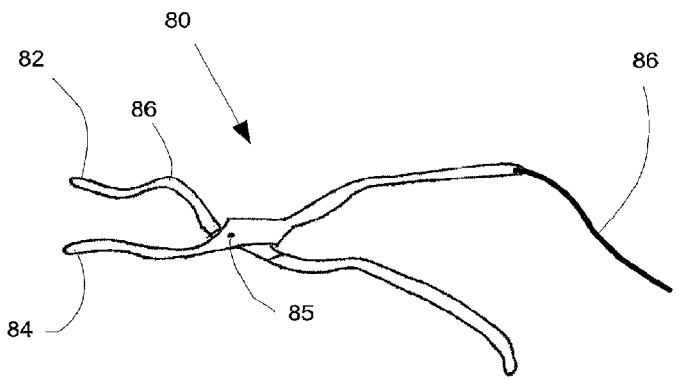
FIG. 5A illustrates one embodiment of a clamp-type nasal valve treatment device.
Figure 5B:
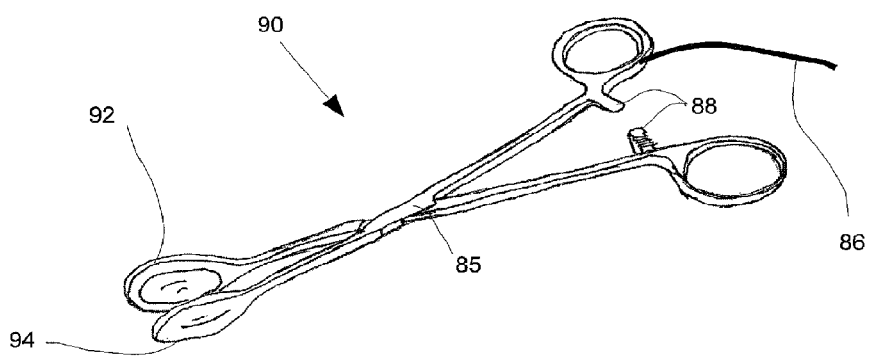
FIG. 5B illustrates another embodiment of a clamp-type nasal valve treatment device.

FIGS. 5A and 5B illustrate re-shaping treatment devices 80 and 90, respectively. The treatment devices 80 and 90 are structured as clamp devices configured to engage a targeted section of the nasal valve with either a clamping force or a spreading force. In some embodiments, the treatment devices of FIGS. 5A and 5B may include energy delivery elements (of any type described herein) which may be powered by a fluid lumen or cable 86.

The treatment device of FIG. 5A includes an outer clamp member 82 and an inner clamp member 84 joined at a hinge point 85. In some embodiments, the outer clamp member 82 may include an outwardly-bent section 86 sized and configured to extend around the bulk of a patient's nose when the inner clamp member may be positioned inside the patient's nose. The inner and outer tissue-engaging tips at the distal ends of the inner and outer clamp members may be configured to impart a desired shape to the internal and/or external nasal valve. In some embodiments, the tissue-engaging tips may be removable to allow for sterilization and/or to allow for tips of a wide range of shapes and sizes to be used with a single clamp handle.

The treatment device of FIG. 5B includes an outer clamp member 92 and an inner clamp member 94 joined at a hinge point 95. The inner and outer tissue-engaging tips at the distal ends of the inner and outer clamp members may be configured to impart a desired shape to the internal and/or external nasal valve. In the illustrated embodiment, the outer clamp member 92 includes a concave inner surface, and the inner clamp member includes a mating convex inner surface. The shape and dimensions of the mating surfaces may be designed to impart a desired shape to the structures of a patient's nose. In some embodiments, the shape of the mating surfaces may be modified by the operator to impart an optimal configuration to the treated tissue. The shape modification of the mating surfaces can be accomplished pre-procedure or during the procedure and can be either fixed after modification or capable of continuous modification.

In some embodiments, the tissue-engaging tips may be removable to allow for sterilization and/or to allow for tips of a wide range of shapes and sizes to be used with a single clamp handle.

In alternative embodiments, the devices of FIGS. 5A and 5B may be used as spreader devices by placing both clamp tips in one nasal valve and separating the handles, thereby separating the distal tips. In alternative embodiments, the handles may be configured to expand in response to a squeezing force. The shapes of the distal tips may be designed to impart a desired shape when used as a spreading device.

Figure 6:
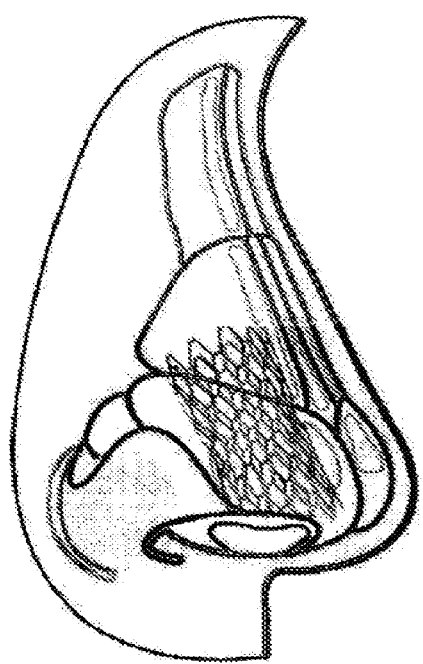
FIG. 6 depicts a partially-transparent perspective view showing a stent implanted in a nose.

The re-shaping elements of FIGS. 3-5B are generally configured to be used once and removed from a patient's nose once a treatment is delivered. In some embodiments, treatments may further involve placing longer term treatment elements, such as stents, molds, external strips, etc. for a period of time after treatment. An example of such a stent placed within a patient's nose after treatment is shown in FIG. 6. In some embodiments, the stent may be configured to be removed after a therapeutically effective period of time following the treatment. In some embodiments, such a therapeutically effective period of time may be on the order of days, weeks or more.

In some embodiments, the treatment element 32 may be configured to deliver heat energy to the nasal valve. In such embodiments, the treatment element may comprise any suitable heating element available to the skilled artisan. For example, the treatment element 32 may comprise electrical resistance heating elements. In alternative embodiments, the heating element may comprise conduits for delivering high-temperature fluids (e.g. hot water or steam) onto the nasal tissue. In some embodiments, a high-temperature fluid heating element may comprise flow channels which place high-temperature fluids into conductive contact with nasal tissues (e.g. through a membrane wall) without injecting such fluids into the patients nose. In further embodiments, any other suitable heating element may be provided. In further embodiments, the treatment element 32 may comprise elements for delivering energy in other forms such as light, laser, RF, microwave, cryogenic cooling, DC current and/or ultrasound in addition to or in place of heating elements.

U.S. Pat. No. 6,551,310 describes embodiments of endoscopic treatment devices configured to ablate tissue at a controlled depth from within a body lumen by applying radio frequency spectrum energy, non-ionizing ultraviolet radiation, warm fluid or microwave radiation. U.S. Pat. No. 6,451,013 and related applications referenced therein describe devices for ablating tissue at a targeted depth from within a body lumen. Embodiments of laser-treatment elements are described for example in U.S. Pat. No. 4,887,605 among others. U.S. Pat. No. 6,589,235 teaches methods and device for cartilage reshaping by radiofrequency heating. U.S. Pat. No. 7,416,550 also teaches methods and devices for controlling and monitoring shape change in tissues, such as cartilage. The devices described in these and other patents and publications available to the skilled artisan may be adapted for use in treating portions of a nasal valve or adjacent tissue as described herein. U.S. Pat. Nos. 7,416,550, 6,589,235, 6,551,310, 6,451,013 and 4,887,605 are hereby incorporated by reference in their entireties.

In alternative embodiments, similar effects can be achieved through the use of energy removal devices, such as cryogenic therapies configured to transfer heat energy out of selected tissues, thereby lowering the temperature of targeted tissues until a desired level of tissue modification is achieved. Examples of suitable cryogenic therapy delivery elements are shown and described for example in U.S. Pat. Nos. 6,383,181 and 5,846,235, the entirety of each of which is hereby incorporated by reference.

In some embodiments, the treatment element 32 may be configured to deliver energy (e.g. heat, RF, ultrasound, microwave) or cryo-therapy uniformly over an entire outer surface of the treatment element 32, thereby treating all nasal tissues in contact with the treatment element 32. Alternatively, the treatment element 32 may be configured to deliver energy at only selective locations on the outer surface of the treatment element 32 in order to treat selected regions of nasal tissues. In such embodiments, the treatment element 32 may be configured so that energy being delivered to selected regions of the treatment element can be individually controlled. In some embodiments, portions of the treatment element 32 are inert and do not deliver energy to the tissue. In further alternative embodiments, the treatment element 32 may be configured with energy-delivery (or removal) elements distributed over an entire outer surface of the treatment element 32. The control system 42 may be configured to engage such distributed elements individually or in selected groups so as to treat only targeted areas of the nasal passageway.

Figure 7:
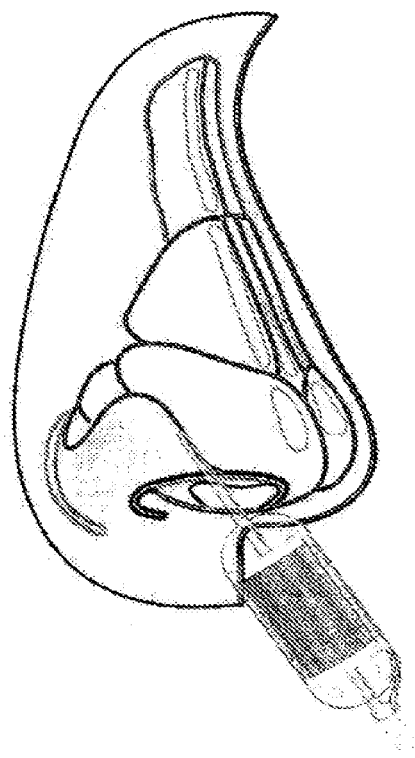
FIG. 7 depicts a perspective view illustrating an energy delivery balloon being inserted into a nose.

In some embodiments, the treatment element 32 may be a balloon with energy delivery elements positioned at locations where energy transfer is sufficient or optimal to effect change in breathing. Such a balloon may be configured to deliver energy while the balloon is in an inflated state, thereby providing a dual effect of repositioning tissue and delivering energy to effect a change the nasal valve. In other embodiments, a balloon may also deliver heat by circulating a fluid of elevated temperature though the balloon during treatment. The balloon can also delivery cryotherapy (e.g. by circulating a low-temperature liquid such as liquid nitrogen) while it is enlarged to increase the nasal valve diameter or otherwise alter the shape of a nasal valve. FIG. 7 illustrates an example of an energy-delivery balloon being inserted into a patient's nose for treatment. Several embodiments may be employed for delivering energy treatment over a desired target area. For example, in some embodiments, a laser treatment system may treat a large surface area by scanning a desired treatment pattern over an area to be treated. In the case of microwave or ultrasound, suitably configured transducers may be positioned adjacent to a target area and desired transducer elements may be activated under suitable depth focus and power controls to treat a desired tissue depth and region. In some embodiments, ultrasound and/or microwave treatment devices may also make use of lenses or other beam shaping of focusing devices or controls. In some embodiments, one or more electrical resistance heating elements may be positioned adjacent to a target region, and activated at a desired power level for a therapeutically effective duration. In some embodiments, such heating elements may be operated in a cyclical fashion to repeatedly heat and cool a target tissue. In other embodiments, RF electrodes may be positioned adjacent to and in contact with a targeted tissue region. The RF electrodes may then be activated at some frequency and power level therapeutically effective duration. In some embodiments, the depth of treatment may be controlled by controlling a spacing between electrodes. In alternative embodiments, RF electrodes may include needles which may puncture a nasal valve tissue to a desired depth (as shown for example in FIG. 4D and in other embodiments below).

In some embodiments, the treatment element 32 and control system 42 may be configured to deliver treatment energy or cryotherapy to a selected tissue depth in order to target treatment at specific tissues. For example, in some embodiments, treatments may be targeted at tightening sections of the epithelium of the inner surface of the nasal valve. In other embodiments, treatments may be targeted at strengthening soft tissues underlying the epithelium. In further embodiments, treatments may be targeted at strengthening cartilage in the area of the upper lateral cartilage. In still further embodiments, treatments may be targeted at stimulating or modifying the tissue of muscles of the nose or face in order to dilate the nasal valve.

In some embodiments, the treatment element 32 and control system 42 may be configured to deliver treatment energy to create specific localized tissue damage or ablation, stimulating the body's healing response to create desired conformational or structural changes in the nasal valve tissue.

In some embodiments, the treatment element 32 and control system 42 may be configured to create specific localized tissue damage or ablation without the application of energy. For example the treatment element 32 may be configured to chemically cauterize tissue around a nasal valve by delivering a cauterizing agent (e.g., silver nitrate, trichloroacetic acid, cantharidin, etc.) to the tissue. The treatment element 32 may comprise apertures configured to permit the cauterizing agent pass through to the nose. In some embodiment, the treatment element 32 may aerosolize the cauterizing agent. Other delivery methods are also contemplated. The treatment element 32 may comprise a lumen through which the cauterizing agent passes. The lumen may be fluidly connected to a reservoir or container holding the cauterizing agent. The device may comprise an input control (e.g., a button or switch) configured to control the delivery of the cauterizing agent. In some embodiments, the treatment element 32 comprises an applicator that can be coated in a cauterizing agent (e.g., dipped in a reservoir of cauterizing agent, swabbed with cauterizing agent, etc.) and the coated treatment element applicator may be applied to tissue to be treated. In some embodiments, the treatment element may be configured to apply cauterizing agent to the patient over a prolonged period of time (e.g., 30 seconds, 1 minute, 2 minutes, etc.). In some embodiment, the treatment element 32 comprises shields configured to protect tissue surrounding the tissue to be treated from coming into contact with the cauterizing agent. In some embodiments, a separate element is used to shield tissue surrounding the tissue to be treated from coming into contact with the cauterizing agent. While such treatments may be performed without the application of energy, in some embodiments, they are performed in conjunction with energy treatments.

In some embodiments, a treatment element may be configured to treat a patient's nasal valve by applying treatment (energy, cryotherapy, or other treatments) from a position outside the patient's nose. For example, in some embodiments, the devices of FIGS. 5A and 5B may be configured to apply energy from an element positioned outside a patient's nose, such as on the skin. In another embodiment, a device may be placed on the external surface of the nose that would pull skin to effect a change in the nasal airway. Treatment may then be applied to the internal or external nasal tissue to achieve a desired nasal valve function.

In some embodiments, the device is configured to position tissue to be re-shaped. In some embodiments, the device comprises features and mechanisms to pull, push or position the nasal tissue into a mold for re-shaping. For example, suction, counter traction, or compression between two parts of the device may be used.

In some embodiments, the treatment device comprises one, two, three, four, or more molds configured to re-shape tissue. The mold or re-shaping element may be fixed in size or may vary in size. The mold may also be fixed in shape or may vary in shape. For example, the size or shape of the element may be varied or adjusted to better conform to a nasal valve of a patient. Adjustability may be accomplished using a variety of means, including, for example, mechanically moving the mold by way of joints, arms, guidewires, balloons, screws, stents, and scissoring arms, among other means. The mold may be adjusted manually or automatically. The mold is configured to impart a shape to the tissues of the nasal valve area to improve airflow or perceived airflow. The mold is configured to act near the apex of the nasal valve angle, the point at which the upper lateral cartilage meets the cartilage of the nasal septum. It may be desirable to treat in an area near, but not at, the nasal valve so as to avoid post procedure scarring and/or adhesions. This may be accomplished by focusing treatment on the lateral part of the nasal valve angle.

In some embodiments, the mold or re-shaping element comprises a separate or integrated energy delivery or treatment element (e.g., an electrode such as those described below with respect to FIGS. 8A-8J). The treatment element may be fixed or adjustable in size. For example, the treatment element may be adjusted to better conform to the nasal valve of a patient. In the case of a separate re-shaping element and treatment element, a distance between the two elements may either be fixed or adjustable. Adjustability may be accomplished using a variety of means, including, for example, mechanically moving the mold by way of joints, arms, guidewires, balloons, screws, stents, and scissoring arms, among other means.

In some embodiments, the mold or another part of the device is configured to deliver cooling (discussed in more detail below). In some embodiments, the mold or re-shaping element comprises a balloon configured to reshape and/or deform tissue. A balloon may also be configured to deliver energy such as heat using hot liquid or gas.

Examples of Various Electrode Arrangements

Described below are embodiments of various treatment devices and, more particularly, electrode arrangements that may be used for applying energy to the nasal valve area. These electrodes may, for example, deliver RF energy to preferentially shape the tissue to provide improved nasal breathing. In some embodiments, one or more electrodes may be used alone or in combination with a tissue shaping device or mold. In other embodiments, one or more electrodes may be integrally formed with a tissue shaping device or mold, so that the electrodes themselves create the shape for the tissue. In some embodiments, the energy delivery devices may utilize alternating current. In some embodiments, the energy delivery devices may utilize direct current. In certain such embodiments, the energy delivery device may comprise a configuration utilizing a grounding pad.

In some embodiments, the term "electrode" refers to any conductive or semi-conductive element that may be used to treat the tissue. This includes, but is not limited to metallic plates, needles, and various intermediate shapes such as dimpled plates, rods, domed plates, etc. Electrodes may also be configured to provide tissue deformation in addition to energy delivery. Unless specified otherwise, electrodes described can be monopolar (e.g., used in conjunction with a grounding pad) or bipolar (e.g., alternate polarities within the electrode body, used in conjunction with other tissue-applied electrodes).

In some embodiments, "mold", "tissue shaper", "re-shaping element" and the like refer to any electrode or non-electrode surface or structure used to shape, configure or deflect tissue during treatment.

In some embodiments, "counter-traction" refers to applying a force opposite the electrode's primary force on the tissue to increase stability, adjustability, or for creating a specific shape.

Figure 8A:
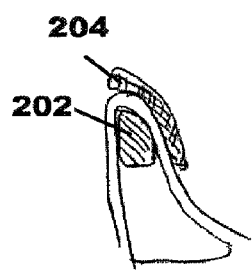
FIGS. 8A-8J depict embodiments of various electrode arrangements for applying energy to the nasal valve area.
Figure 8C:
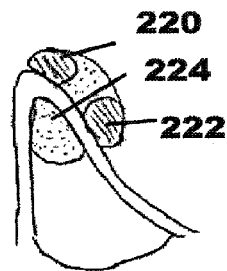
Figure 8B:
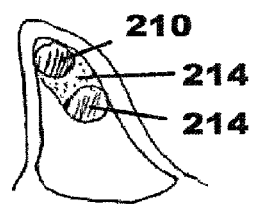

As shown in FIG. 8A, in some embodiments, bipolar electrodes may be used to deliver energy, with one electrode 202 placed internally in the nasal valve, for example against the upper lateral cartilage, and one electrode 204 placed externally on the outside of the nose. This embodiment may advantageously provide direct current flow through the tissue with no physical trauma from needles (as shown in some embodiments below). As shown in FIG. 8B, in some embodiments, bipolar electrodes may be used to deliver energy, with both electrodes 210, 212 placed internally. An insulating spacer 214 may be placed between them. This embodiment may be simple and may advantageously minimize current flow through the skin layer. In some embodiments, bipolar electrodes 220, 222 may be both placed externally and may be connected to a passive molding element 224 placed inside the nasal valve adjacent to tissue to be treated, as shown in FIG. 8C. This embodiment may advantageously minimize the potential for mucosal damage. In some embodiments, electrodes placed internally may be shaped to function as a mold or may comprise an additional structure that may function as a mold.

Figure 8D:
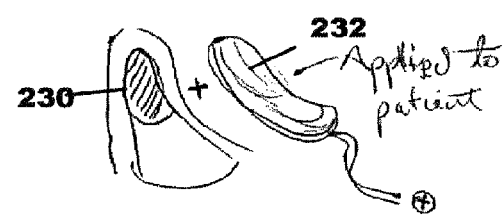

In some embodiments, a monopolar electrode may be used to deliver energy. As shown in FIG. 8D, the electrode 230 may be placed internally and may be connected to an external, remote grounding pad 232. The grounding pad 232 may, for example, be placed on the abdomen of a patient or in other desired locations. This embodiment may advantageously be simple to manufacture and may minimize current flow through the skin. In some embodiments, a monopolar electrode may be placed externally and may be connected to a molding element placed inside the nasal valve as well as a remote grounding pad. This embodiment may also advantageously be simple to manufacture, may minimize mucosal current flow, and may also be simple to position. In some embodiments, electrodes placed internally may be shaped to function as a mold or may comprise an additional structure that may function as a mold.

Figure 8E:
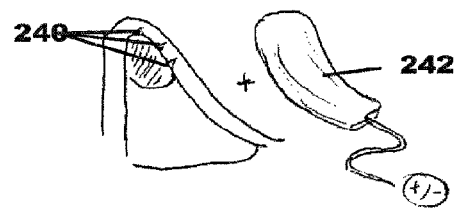

In some embodiments, monopolar transmucosal needles may be used to deliver energy. The needle electrodes 240 may be placed internally, as shown in FIG. 8E penetrating through the mucosa to the cartilage, and a remote grounding pad 242 or element may be placed externally. In some embodiments, monopolar transmucosal needles may be used in conjunction with one or more molding elements which may be disposed on or around the needles. In some embodiments, monopolar transdermal needles may be used to deliver energy. In other embodiments (not shown), the needles may be placed external to the nose, and penetrate through to tissue to be treated. Needle configurations may advantageously target the cartilage tissue to be treated specifically. The monopolar transdermal needles may be used in conjunction with an internal molding device (not shown).

In some embodiments, bipolar transmucosal needles may be used to deliver energy to tissue to be treated. The needles may be placed internally, with an insulating spacer between them and may penetrate through the mucosa to the cartilage to be treated. In some embodiments, the bipolar transmucosal needles may be used in combination with one or more internal molding elements. The one or more molding elements may be placed on or near the needles. In some embodiments, bipolar transdermal needles may be used to deliver energy. In other embodiments, the transdermal needles may be placed externally and penetrate through to tissue to be treated. Needle configurations may advantageously target the cartilage tissue to be treated specifically. The transdermal bipolar needles may be utilized in conjunction with an internal molding element.

Figure 8F:
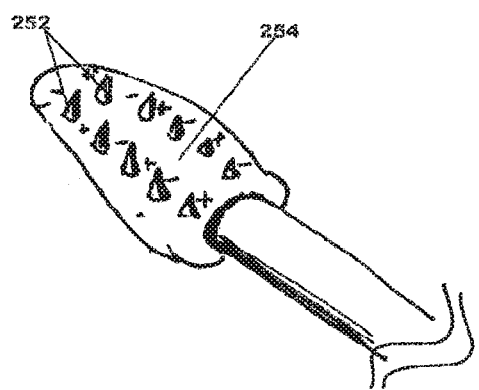

As shown in FIG. 8F, in some embodiments, an array of electrodes comprising one, two, or many pairs of bipolar needles 252 are located on a treatment element configured to be placed into contact with the cartilage. An insulator 254 may be disposed between the bipolar needles 252. An insulator may also be utilized on part of the needle's length to allow energy to be delivered only to certain tissue structures, such as cartilage. The electrodes may be placed either internally or transmucosally or they may be placed externally or transdermally. In the embodiment illustrated in FIG. 8F, the insulator 254 may also function as a mold or molding element. In other embodiments (not shown), the array of electrodes is used in conjunction with a separate tissue re-shaping element.

Figure 8G:
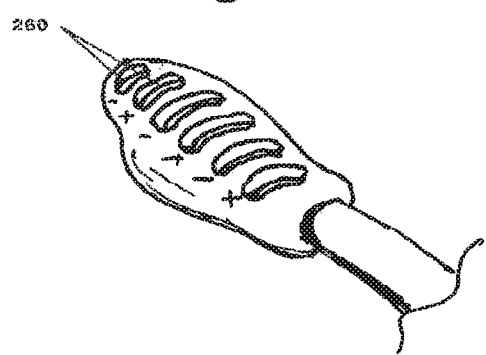

FIG. 8G illustrates another embodiment of a treatment element comprises one, two or many pairs of bipolar electrodes 260. As opposed to FIG. 8F, where the pairs of electrodes are arranged side-by-side, the embodiment of FIG. 8G arranges the pairs of electrodes along the length of the treatment element. The electrodes of FIG. 8G are also non-penetrating, in contrast to the needles of FIG. 8F. The electrodes 260 may be placed against either the skin, externally, or the mucosa, internally as a means of delivering energy to target tissue such as cartilage.

In some embodiments of treatment devices comprising an array or multiple pairs of electrodes, each pair of electrodes (bipolar) or each electrode (monopolar) may have a separate, controlled electrical channel to allow for different regions of the treatment element to be activated separately. For example, the needles or needle pairs of FIG. 8F may be individually controlled to produce an optimal treatment effect. For another example, the separate electrodes of FIGS. 8B and 8C may be individually controlled to produce an optimal treatment effect. Other examples are also contemplated. The channels may also comprise separate or integrated feedback. This may advantageously allow for more accurate temperature control and more precise targeting of tissue. Separate control may also allow energy to be focused and/or intensified on a desired region of the treatment element in cases where the anatomy of the nasal tissue/structures does not allow the entire electrode region of the treatment element to engage the tissue. In such embodiments, the nasal tissue that is in contact with the treatment element may receive sufficient energy to treat the tissue.

Figure 8H:
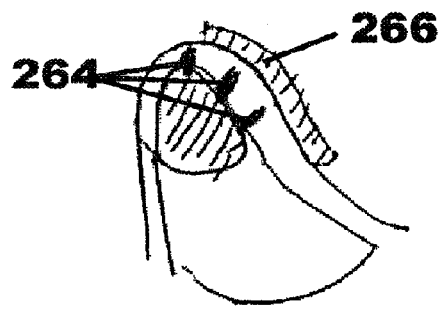
Figure 8I:
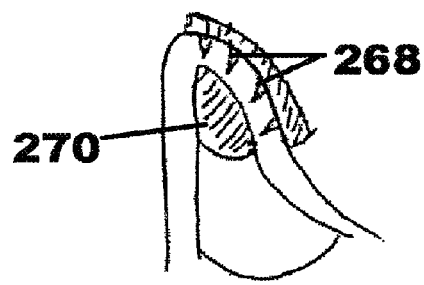
Figure 8J:
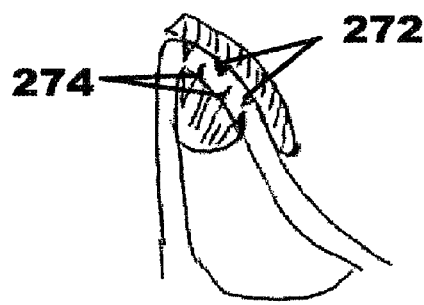

Combinations of the described electrode configurations may also be utilized to deliver energy to tissue to be treated (e.g., by being reshaped). For example, transmucosal needles 264 may be placed internally, penetrating through to the tissue to be treated, and an electrode 266 may be placed externally, as shown in FIG. 8H. This embodiment may advantageously target the cartilage tissue specifically and be biased for mucosal preservation. For another example, transdermal needles 268 may be placed externally and an electrode 270 may be placed internally, as shown in FIG. 8I. This embodiment may advantageously target the cartilage tissue specifically and be biased towards skin preservation. For another example bipolar needle electrodes 272, 274 can be placed both transdermally or externally and transmucosally or internally, as shown in FIG. 8J. This embodiment may advantageously target the cartilage tissue specifically. Some embodiments of treatment elements may include inert areas which do not delivery energy to the tissue. Other combinations of electrode configuration are also possible.

Examples of Treatment Devices Including Electrodes

Embodiments of treatment devices incorporating treatment elements such as the electrodes described above are illustrated in FIGS. 9A-21B. The instrument designs described in these embodiments may be used in a device such as the device 30, described above, and in the system of FIG. 3. In some embodiments, the devices provide tissue re-shaping or molding in addition to energy delivery. Applying energy to the nasal valve may require properly positioning the electrode(s) at the nasal valve, deflecting or deforming the tissue into a more functional shape, and delivering or applying energy consistently prior to device removal. Embodiments described herein may advantageously provide adjustability, visualization of effect, ease of use, ease of manufacturability and component cost. Molding and reshaping of the tissues of the nasal valve may allow for non-surgical nasal breathing improvement without the use of implants.

Figure 9A:
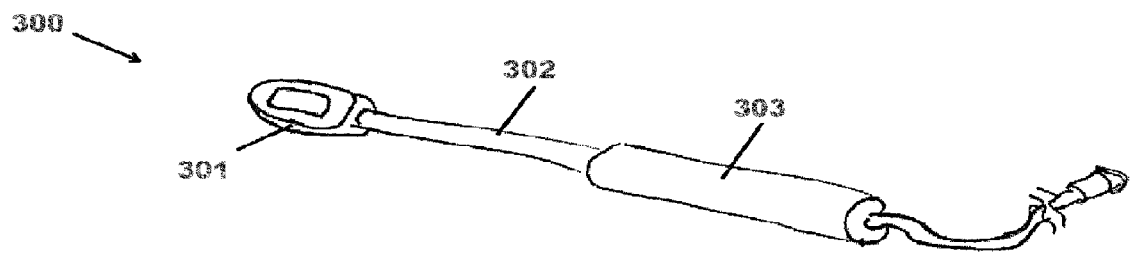
FIGS. 9A and 9B illustrate embodiments of devices for applying energy to the nasal valve area using a monopolar electrode.
Figure 9B:
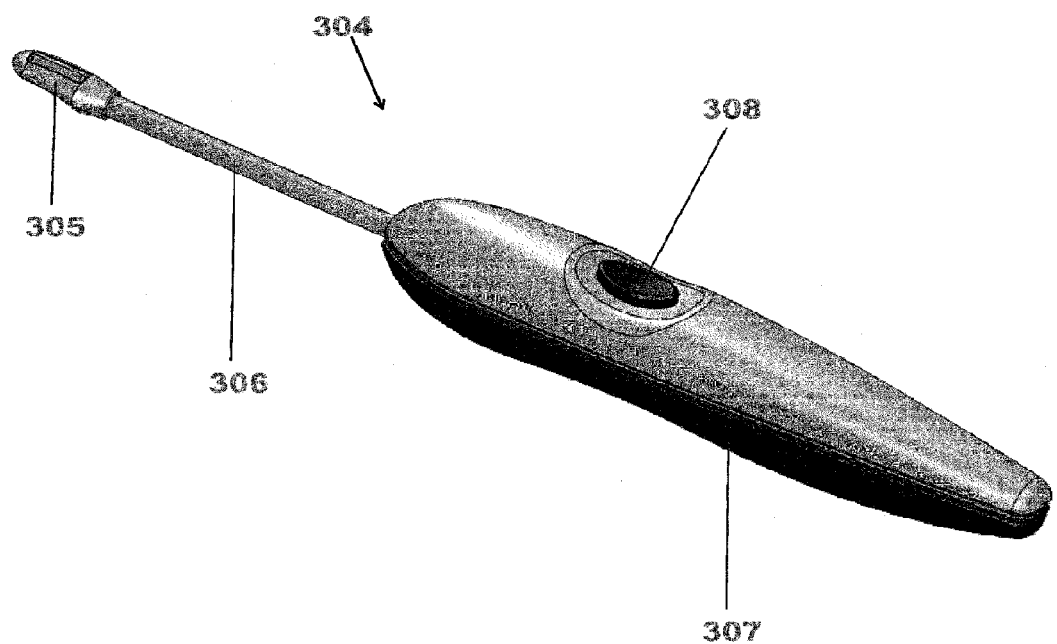

FIG. 9A depicts a device 300 comprising a single inter-nasal monopolar electrode 301 located at the end of a shaft 302. The shaft is attached to a handle 303. The electrode configuration may be similar to that described with respect to FIG. 8D. FIG. 9B depicts another device 304 comprising a single inter-nasal, monopolar electrode 305. The electrode 305 is located at the distal end of a shaft 306, which is attached to a handle 307. The handle comprises a power button 308 that may be used to activate and deactivate the electrode. As stated above, the device 304 may either comprise a generator or be connected to a remote generator. The electrode 305 may be provided on an enlarged, distal end of the shaft 306, and in the embodiment illustrated has a convex shape configured to press against and create a concavity in the nasal valve cartilage.

Figure 10A:
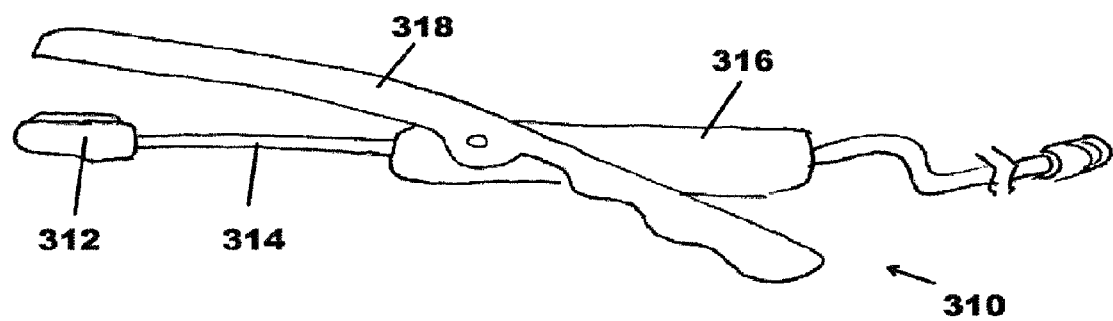
FIGS. 10A and 10B illustrate an embodiment of a device for applying energy to the nasal valve area using a monopolar electrode and an external mold.
Figure 10B:
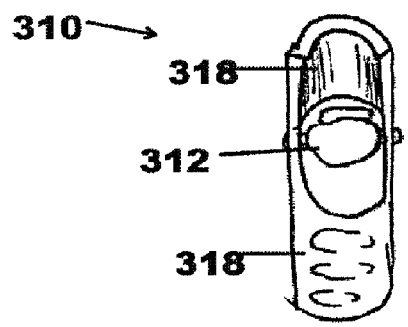

FIG. 10A depicts a side view of a device 310 comprising a single inter-nasal electrode 312 located at the end of a shaft 314. The shaft is attached to a handle 316. An external mold 318 is attached to the handle 316 and can be moved relative to the electrode shaft 314. The external mold 318 has a curved shape with an inner concave surface that may be moved in order to press against an external surface of a patient's nose to compress tissue between the external mold 318 and the electrode 312. FIG. 10B provides a front view of the device 310.

Figure 11A:
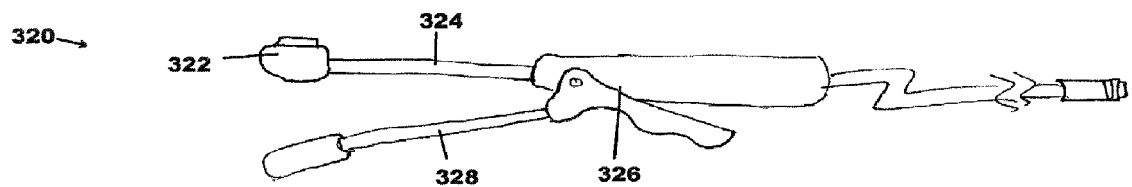
FIGS. 11A and 11B illustrate embodiments of devices for applying energy to the nasal valve area using electrode(s) and a counter-traction element.

FIG. 11A depicts a device 320 comprising a single inter-nasal electrode 322 attached to the end of a shaft 324. The shaft 324 is attached to a handle 326. An internal shaft 328 comprising a tissue-contacting surface is attached to the handle 326. The internal shaft 328 can be moved relative to the electrode shaft 324 and may provide counter-traction and/or positioning. For example, when the electrode 322 is placed against a patient's upper lateral cartilage, the counter-traction element 328 may be pressed against the patient's nasal septum.

Figure 11B:
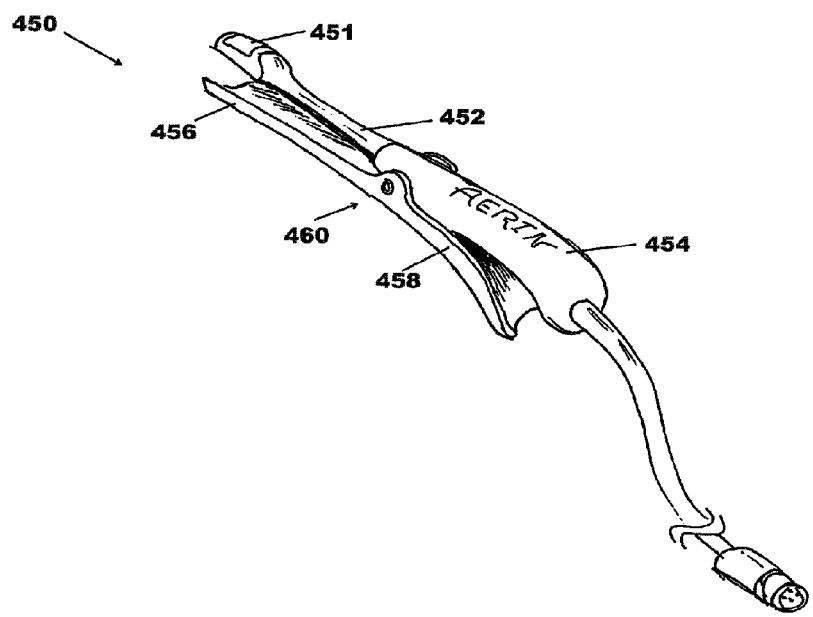

FIG. 11B depicts a device 450 similar to device 320 of FIG. 11A comprising an inter-nasal electrode 451 located at a distal end of a shaft 452 connected to a handle 454. The device 450 further comprises a counter-traction element 456 connected to a handle 458. Like the device 320 depicted in FIG. 11A, the connection 460 between the two handles 454, 458 is such that squeezing the two handles 454, 458 together causes the electrode 451 and the counter-traction element 456 to move away from each other, spreading the tissue they are contacting.

Figure 12A:
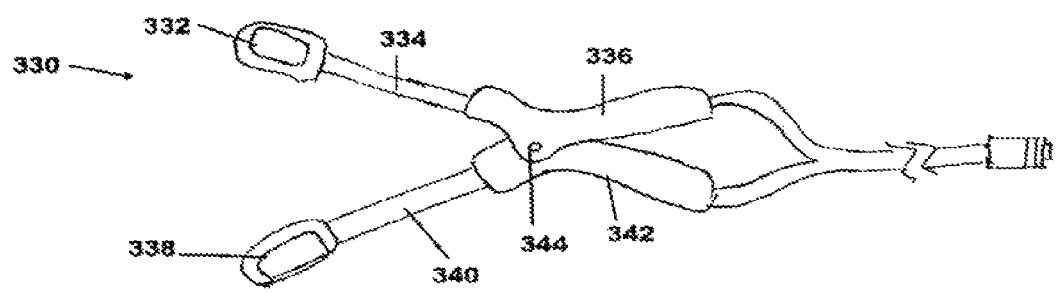
FIGS. 12A and 12B illustrate embodiments of devices for applying energy to the nasal valve area configured to be inserted into both nostrils simultaneously.

FIG. 12A depicts a device 330 comprising a single inter-nasal electrode 332 located at the end of a shaft 334. The shaft 334 is attached to a handle 336. The device 330 comprises another single inter-nasal electrode 338 attached to the end of a shaft 340. The shaft 340 is attached to a handle 342. The device comprises a connection 344 between the two handles 340, 342 that allows simultaneous deformation and treatment of both nostrils.

Figure 12B:
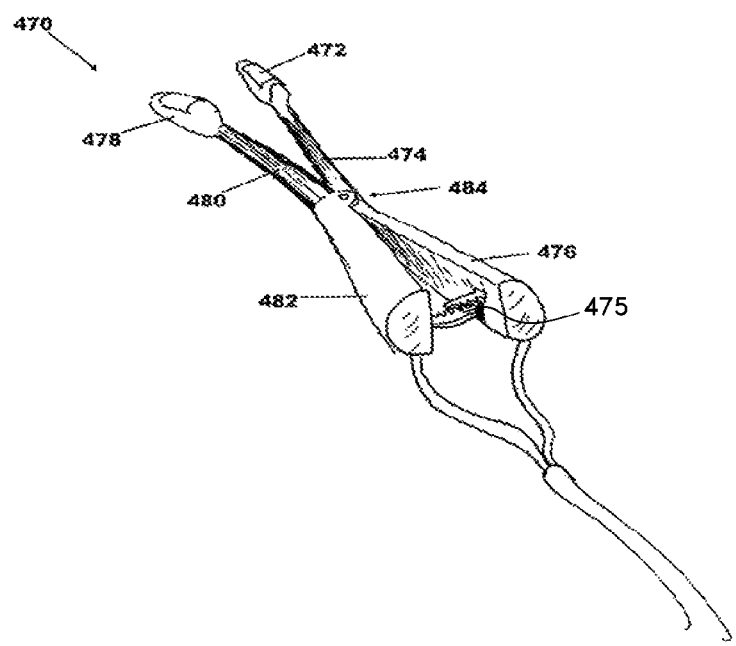

FIG. 12B depicts a device 470 similar to device 330 of FIG. 12A comprising a first inter-nasal electrode 472 located at a distal end of a shaft 474 connected to a handle 476. The device 470 comprises a second inter-nasal electrode 478 located at a distal end of a second shaft 480 connected to a second handle 482. The connection 484 between the two handles 476, 482 is such that squeezing the handles 476, 482 together causes the electrodes 472, 478 to move away from one another, spreading any tissue they may be in contact with. The device 470 comprises a ratcheting mechanism 475 between the two handles 476, 482 that allows the relative positions of the electrodes 472, 478 to be locked during treatment.

Figure 13A:
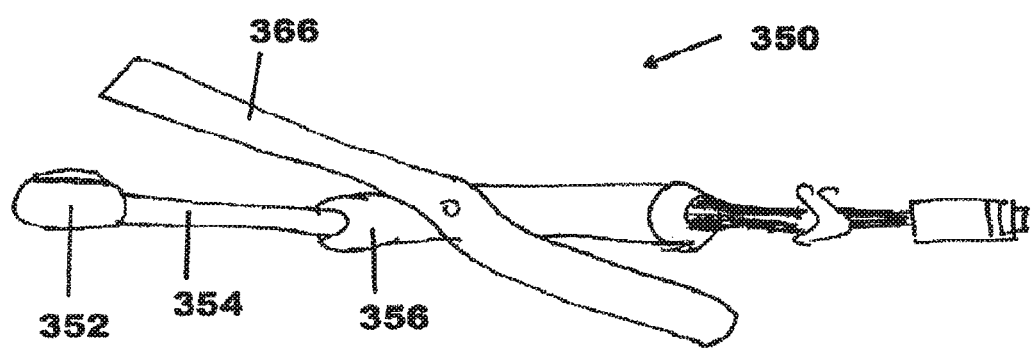
FIGS. 13A-13E illustrate embodiments of devices for applying energy to the nasal valve area configured to be inserted into both nostrils simultaneously, having a mold or counter-traction element for engaging the nose externally.

FIG. 13A depicts a side view of a device 350 also used for treating two nostrils comprising an inter-nasal electrode 352 attached to the end of a shaft 354. The shaft 354 is attached to a handle 356. As seen in the front view provided in FIG. 13B, the device 350 comprises a second inter-nasal electrode 358. The second inter-nasal electrode 358 is attached to the end of a shaft which is attached to a handle. A connection between the two handles allows simultaneous deformation and treatment of the nostrils. An external mold 366 is attached to the handles. The mold 366 may be moved relative to the electrode shafts 354, 360 and may provide counter-traction (e.g., against the bridge of the nose) and positioning.

Figure 13B:
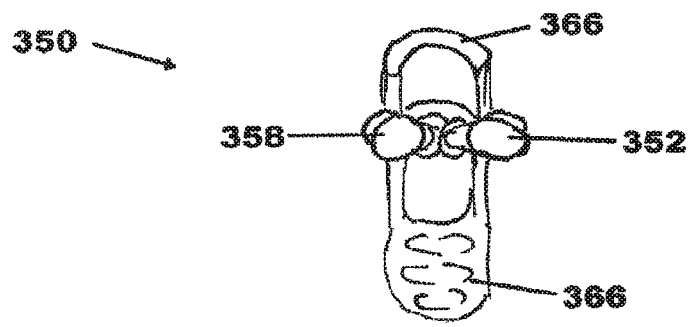
Figure 13C:
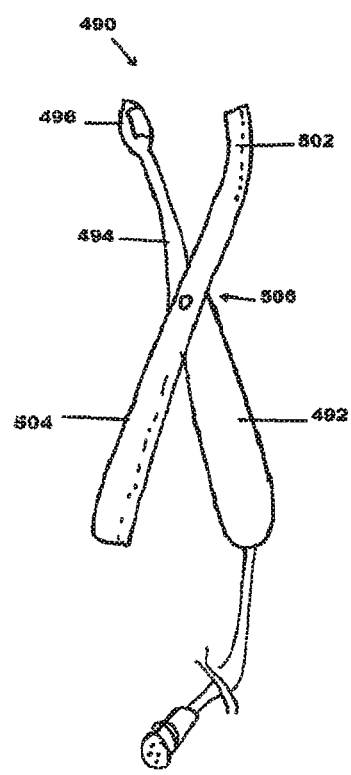
Figure 13D:
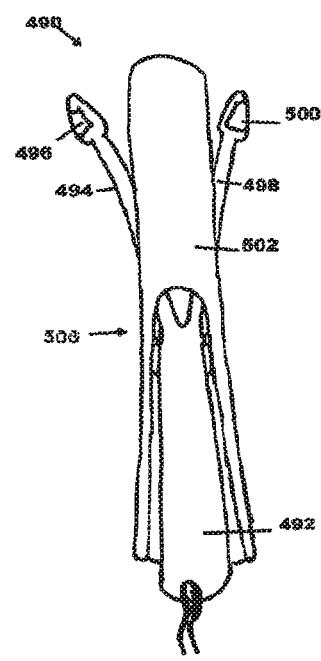
Figure 13E:
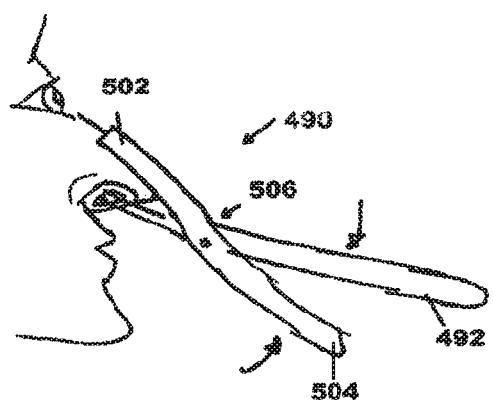

FIGS. 13C-E depicts a device 490 similar to the device 350 shown in FIG. 13A and FIG. 13B. FIGS. 13C and 13D depict side and top views of a device 490 comprising a handle 492. The handle 492 bifurcates into a first shaft 494 with a first inter-nasal electrode 496 located at a distal end of the shaft 494 and a second shaft 498 with a second inter-nasal electrode 500 located at a distal end of the shaft 498. The device 490 comprises a mold 502 configured to provide counter-traction or compression of the bridge of the nose. The mold 502 comprises a handle 504. The connection 506 between the handles 492, 504 is such that squeezing the two handles 492, 504 causes the electrodes 496, 600 and the mold 502 to be compressed together. FIG. 13E depicts the device 490 being used on a patient. The arrows indicate the directions in which the handles 492, 504 are configured to be squeezed.

Figure 14A:
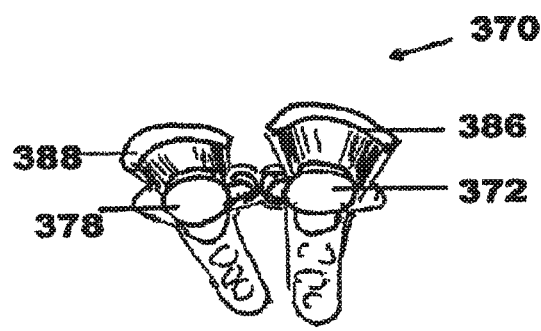
FIGS. 14A and 14B illustrate embodiments of devices for applying energy to the nasal valve area configured to be inserted into both nostrils simultaneously, having separate external molds.
Figure 14B:
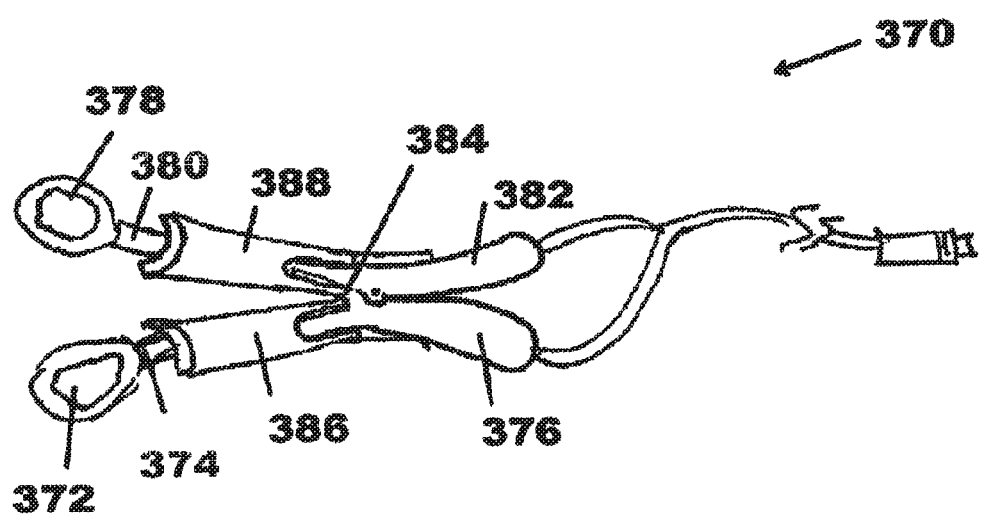

FIG. 14A depicts a front view of a device 370 comprising an inter-nasal electrode 372 attached to the end of a shaft 374 (shown in top view of FIG. 14B). The shaft 374 is attached to a handle 376. The device 370 comprises a second inter-nasal electrode 378 attached to the end of a second shaft 380. The second shaft 380 is attached to a second handle 382. A connection 384 between the two handles 376, 382 may allow simultaneous deformation and treatment of the nostrils. External molds 386, 388 are attached to the handles and can be moved relative to each electrode shaft 374, 380. The molds 386, 388 may provide counter-traction, compression of tissue, positioning, and external tissue deformation.

Figure 15A:
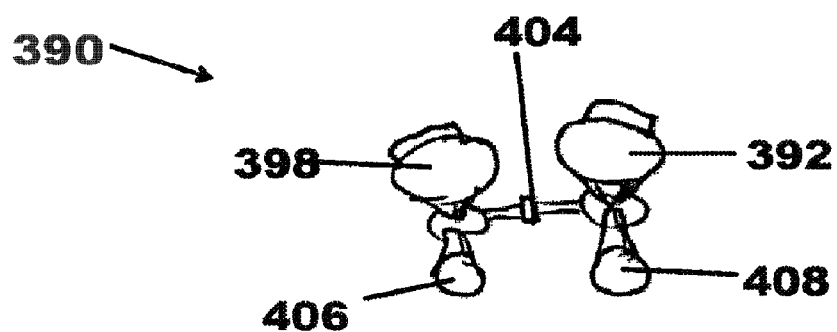
FIGS. 15A-15C illustrate embodiments of devices for applying energy to the nasal valve area configured to be inserted into both nostrils simultaneously, having separate counter-traction elements.
Figure 15B:
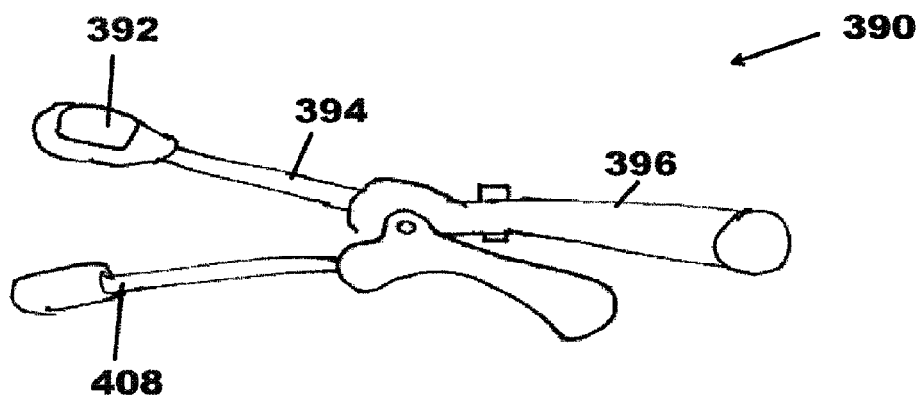
Figure 15C:
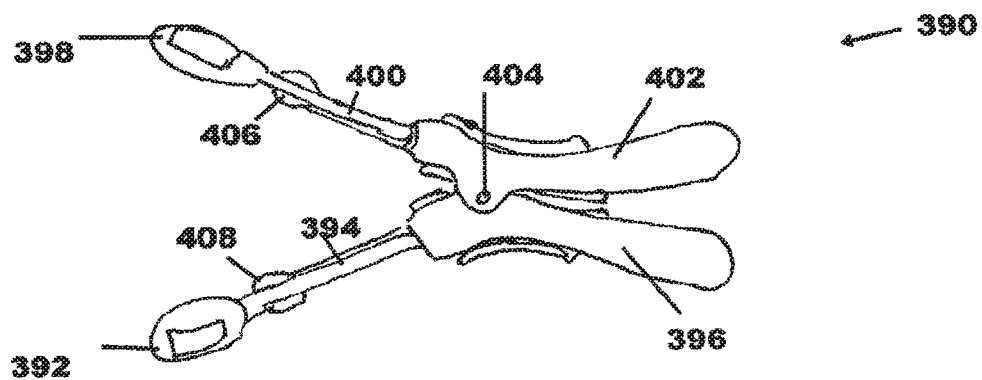

FIG. 15A depicts a front view of device 390 comprising a first inter-nasal electrode 392 and a second inter-nasal electrode 398. As shown in the side view of FIG. 15B, the device 390 comprises a first inter-nasal electrode 392 attached to the end of a shaft 394. The shaft is attached to a handle 396. A second inter-nasal electrode 398 is attached to the end of a second shaft 400, as shown in the top view of FIG. 15C. The second shaft 400 is attached to a second handle 402. A connection 404 between the two handles 396, 402 may allow simultaneous deformation and treatment of the nostrils. Additional internal shafts 406, 408 comprise tissue-contacting surfaces and are attached to the handles 396,402. The internal shafts 406, 408 may be moved relative to each electrode shaft 394, 400 (shown in FIG. 15B) and may provide counter-traction and positioning.

Figure 16:
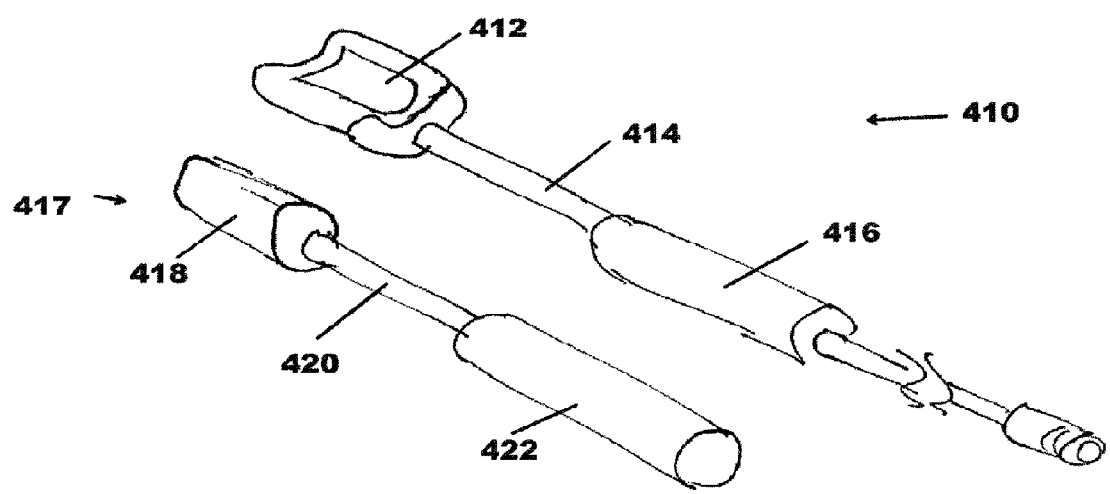
FIG. 16 shows an embodiment of a system comprising a device for applying energy to the nasal valve area with an external electrode and a separate internal mold.

FIG. 16 depicts a system 410 comprising a first device having an extra-nasal electrode 412 along a concave surface configured to positioned against an external surface of a patient's nose, the electrode 412 being attached to the end of a shaft 414. The shaft 414 is attached to a handle 416. A separate device 417 comprising an internal tissue mold 418 is attached to a shaft 420. The internal tissue mold is configured to be positioned inside the patient's nasal valve. The shaft 420 is attached to a handle 422. Each handle 422, 416 may be manipulated individually and may apply energy and deformation to create a desired tissue effect.

Figure 17A:
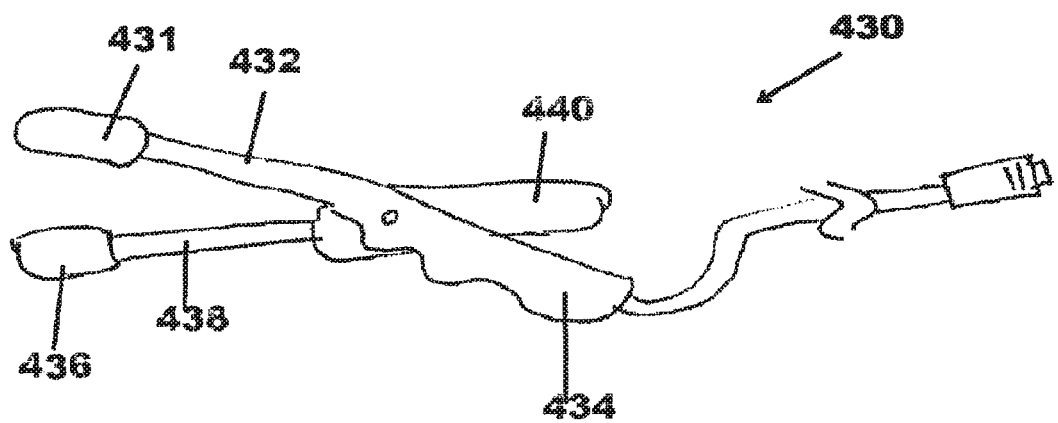
FIGS. 17A and 17B illustrate an embodiment of a device for applying energy to the nasal valve area comprising an external electrode and an internal mold.
Figure 17B:
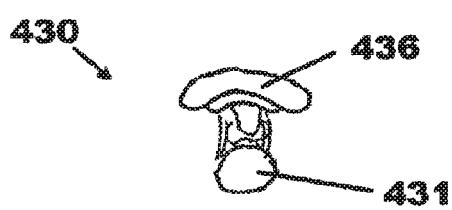

FIG. 17A depicts a side view of a device 430 comprising an extra-nasal electrode 431 attached to the end of a shaft 432. The shaft 432 is attached to a handle 434. The device 430 also comprises an internal tissue mold 436 attached to a shaft 438 which is attached to a handle 440. The handles 434, 440 are attached together and may be moved relative to each other to simultaneously deliver energy and deform tissue. FIG. 17B depicts a front view of the device 430.

Figure 18:
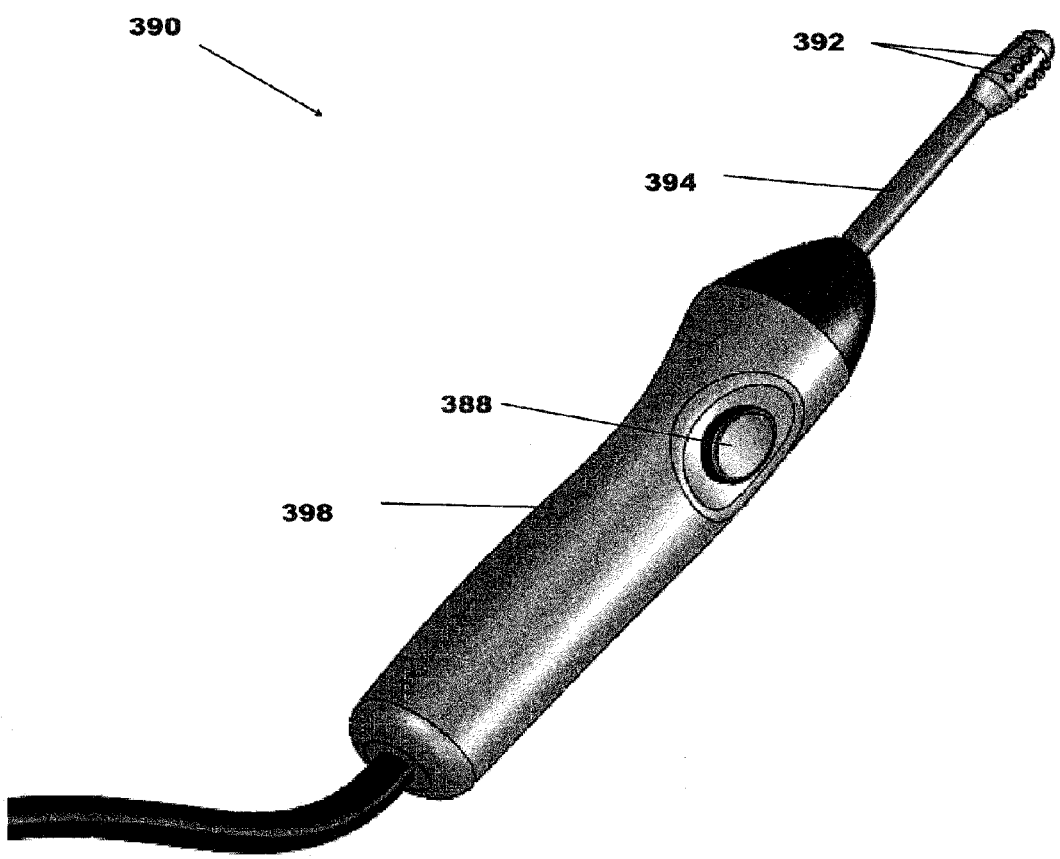
FIG. 18 shows an embodiment of a device for applying energy to the nasal valve area comprising an array of non-penetrating electrodes.

FIG. 18 depicts a device 390 comprising pairs of bipolar electrodes 392 located at the distal end of a shaft 394. The electrodes may be similar to the electrodes described with respect to the electrode configuration of FIG. 8G in that they are non-penetrating. The shaft 394 is connected to a handle 398 which comprises a button configured to activate and deactivate the electrodes. As stated above, the device 380 may either comprise a generator or be connected to a remote generator.

FIG. 19A depicts the treatment element 502 of a treatment device (e.g., device 30). The treatment element 502 of the device comprises a monopolar electrode 504. A cross-section of the treatment element 502 is shown in FIG. 19B. It comprises an asymmetrical shape and has a convex surface where the electrode is positioned configured to conform to only one of a patient's nostrils (for example, a patient's right nostril). More specifically, the convex surface is configured such that when inserted into the particular nostril, the convex surface would be located adjacent the upper lateral cartilage of the nasal valve of that nostril. The treatment element 502 further comprises a light 506 configured to illuminate the treatment area. For example an LED or a visible laser may be used. The visible laser may experience less diffusion in the tissue. Furthermore, the light 506 can be situated such that light can be transmitted through the nasal tissue (including the skin) and can be visualized externally by the user. The user can then use the light to properly position the device in the desired location. Because the electrode 504 is not centered on the treatment element 502 of the device, a separate device having a mirror-image configuration may be required to treat the other nostril.

FIG. 20A depicts the treatment element 512 of a treatment device (e.g., device 30). The treatment element 512 of the device comprises two monopolar electrodes 514, 516 provided side-by-side on a convex surface of the treatment element. The cross section of the treatment element 512, shown in FIG. 20B, is configured to conform to the shape either nostril, depending on which side of the device (and accordingly, which of electrode 514 or 516) is placed in contact with the patient's nasal valve. Comprising two monopolar electrodes 514, 516 may allow the same treatment element 512 to be used for treatment in both nostrils, and each electrode may be activated separately depending on which side needs to be utilized. The treatment element 512 also comprises two lights 518, 520 (e.g., LEDs, lasers) configured to illuminate the treatment area for both nostrils. One or both of the lights 518, 520 can also be situated such that light can be transmitted through the nasal tissue (including the skin) and can be visualized externally by the user. The user can then use the light to properly position the device in the desired location.

FIG. 21A depicts a treatment element 522 of a treatment device (e.g., device 30). The tip 522 of the device comprises a monopolar electrode 524. The tip 522 comprises a symmetrical cross-section as shown in FIG. 21B. The tip 522 comprises a light 526 (e.g., LED) configured to illuminate the treatment area. The light 526 can also be situated such that light can be transmitted through the nasal tissue (including the skin) and can be visualized externally by the user. The symmetrical tip allows the user to treat either left or right nostril. The user can then use the light to properly position the device in the desired location.

Figure 22A:
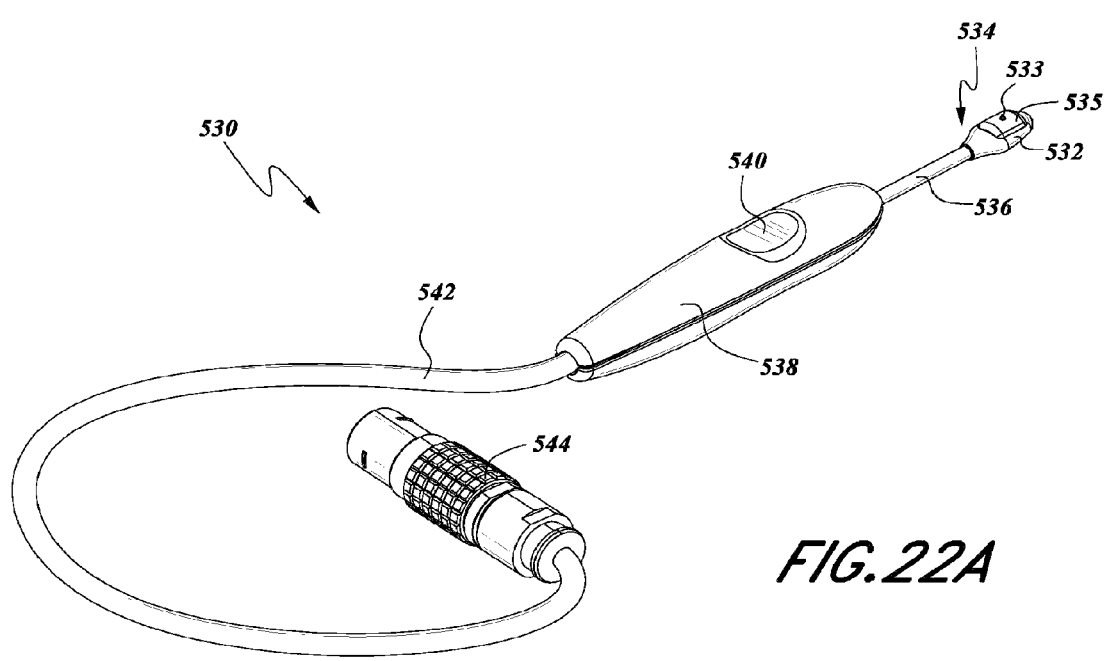

FIGS. 22A-G depict a treatment device 530 similar to the embodiments of FIGS. 8D, 9A, and 9B. FIGS. 22A and 22F provide perspective views of the device 530. The device 530 comprises a treatment element 532 at its distal tip 534. The treatment element 532 comprises an electrode 535. The body of the treatment element 532, itself, may comprise an insulating material. The treatment element 532 may be provided on an enlarged distal tip 534 of an elongate shaft 536, and as in the embodiment illustrated, may have a convex shape configured to press against and create a concavity in the nasal valve cartilage (e.g., in the upper lateral cartilage near the nasal valve). The distal tip 534 is located at the distal end of shaft 536. The shaft is attached at its proximal end to a handle 538. The handle 538 comprises an input control such as a power button 540 on its front side that may be used to activate and deactivate the electrode. The power button 540 may be positioned in a recess of the handle to allow for finger stability when activating and deactivating the electrode. In other embodiments, the input control is in the form of a switch or dial. Other configurations are also possible as described above.

The device 530 comprises a flexible wire or cable 542 electrically connected to an adaptor 544. The adaptor 544 can be used to connect the device 530 to a remote generator (not shown). The adaptor 544 may allow transmission of treatment energy between a remote generator and the device 530. The adaptor may also allow transmission of any sensor signals between the device 530 and a generator or control unit. The device 530 may either comprise an integrated generator or be connected to a remote generator. The treatment device 530 may be provided in a system or kit also including the remote generator. The system or kit (with or without the remote generator) may also include a grounding device and/or a cooling device as described above and further below. In some embodiments, the kit incudes a positioning element (e.g., a "cottle" device) configured to help a user locate the optimal treatment area.

Figure 22B:
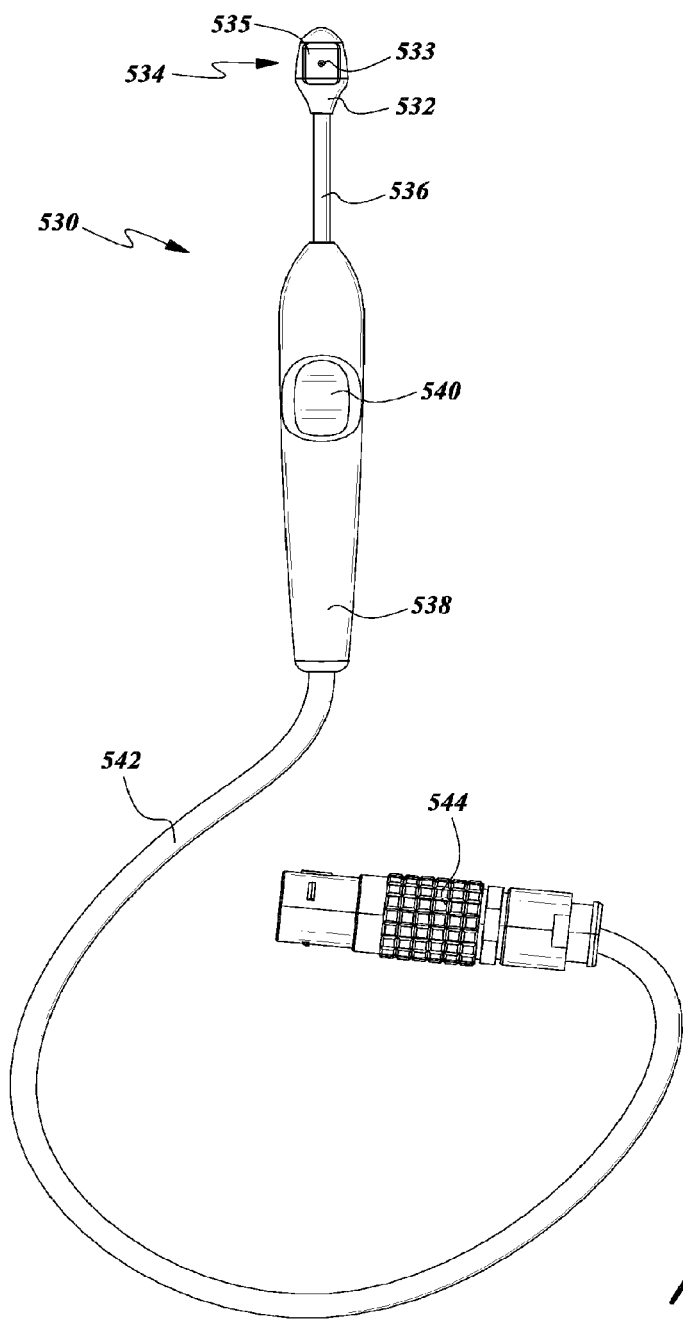
Figure 22C:
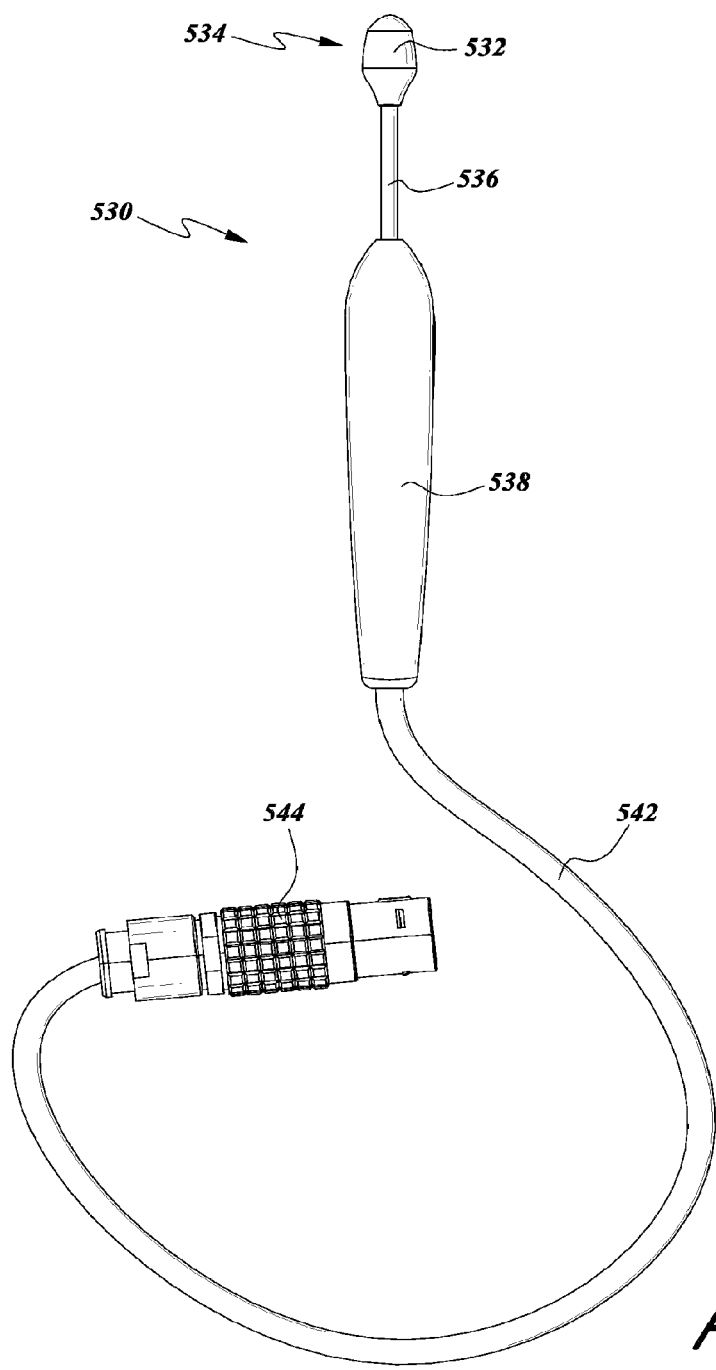

FIGS. 22B and 22C depict front and back views of the device. As shown in FIGS. 22B and 22C, the handle 538 of the device generally as a rounded elongate shape. Other shapes are also possible. For example the device 530 may have a square shaped cross section. In some embodiments, a circumference (or width or cross-sectional area) of the handle 538 may increase distally along the length of the handle 538.

Figure 22D:
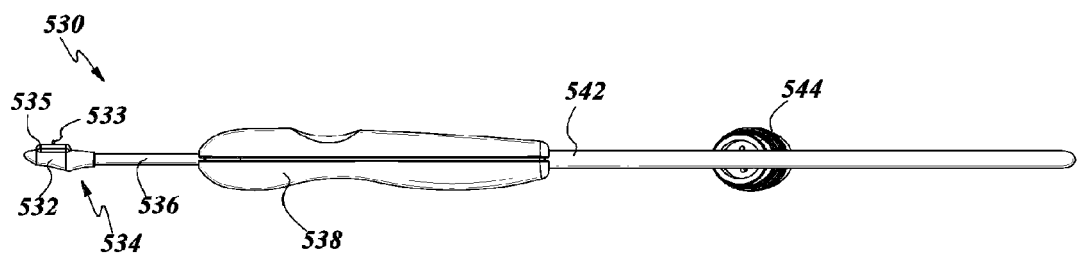
Figure 22E:
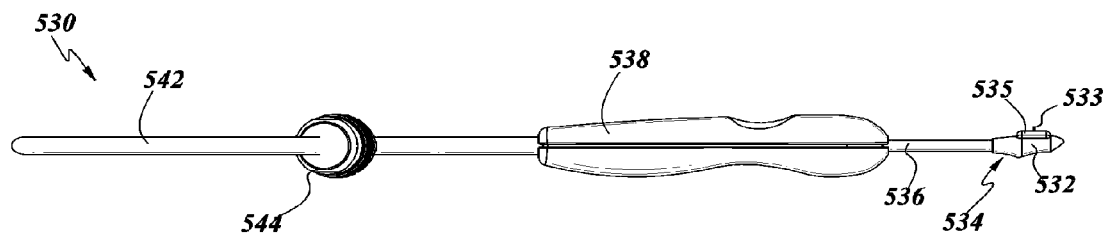

FIGS. 22D and 22E depict side views of the device. As shown in FIGS. 22D and 22E, the handle 538 of the device 530 may comprise an indentation or recess around the middle of the handle 538. This may allow for enhanced grip and control when a user is holding the device. The indentation or recess may be near the input control or power button 540 to allow a user to easily activate and deactivate the device while holding it in a comfortable position.

In some embodiments, the shaft has a width or diameter of about 0.125 inches to about 0.25 inches. In some embodiments, the shaft is about 1.5 inches to about 4 inches long. In some embodiments, the shaft comprises a polymer such as polycarbonate or PEEK. In other embodiments, the shaft comprises stainless steel or other metals. The metals may be coated with an external and/or internal insulating coating (e.g., polyester, polyolefin, etc.). The handle may comprise the same material as the shaft, in some embodiments. In some embodiments, the shaft is rigid. This may allow a user of the device increased control over the deformation of nasal tissue. In some embodiments, the shaft comprises some amount of flexibility. This flexibility may allow a user adjust an angle of the distal tip by bending the distal end of the shaft.

FIG. 22G depicts a larger view of the distal tip 534 of the device 530. As shown best in FIG. 22G, the treatment element 532 comprises a generally elongate shape. The front of the treatment element 532 comprises a shallow, curved surface, providing a convex shape configured to deform the nasal tissue and create a concavity therein. In some embodiments, the front of the treatment element comprises a concave shape. The shape of the front surface of the treatment element may be selected to conform to the nasal tissue. The back of the treatment element 532 also comprises a shallow curved surface. As best seen in FIGS. 22D and 22E, the back surface varies in width along the length of the back surface of the treatment element 532. The back surface widens, moving distally along the tip until it is nearly in line with the proximal end of the electrode plate 532. The back surface then narrows towards the distal tip of the treatment element 532. This shape may maximize visualization of the area to be treated, while, at the same time, providing sufficient rigidity for treatment. Other shapes are also possible. For example, the treatment element may comprise a generally spherical or cylindrical shape. In some embodiments, the treatment element comprises an angular shape (e.g., triangular, conical) which may allow for close conformation to the tissue structures. The treatment element 532 comprises a monopolar electrode plate 532. The monopolar electrode plate 532 can be in the shape of a rectangle having a curved or convex tissue-facing surface. Other shapes are also possible (e.g., square, circular, ovular, etc.). The electrode 532 may protrude slightly from the treatment element 535. This may allow the electrode to itself provide a convex shape configured to create a concavity in tissue to be treated.

In some embodiments, the treatment element has a width or diameter of about 0.25 inches to about 0.45 inches. In some embodiments, the treatment element is about 0.4 inches to about 0.5 inches long. The treatment element can, in some embodiments, comprise a ceramic material (e.g., zirconium, alumina, silicon glass). Such ceramics may advantageously possess high dielectric strength and high temperature resistance. In some embodiments, the treatment element comprises polyimides or polyamides which may advantageously possess good dielectric strength and elasticity and be easy to manufacture. In some embodiments, the treatment element comprises thermoplastic polymers. Thermoplastic polymers may advantageously provide good dielectric strength and high elasticity. In some embodiments, the treatment element comprises thermoset polymers, which may advantageously provide good dielectric strength and good elasticity. In some embodiments, the treatment element comprises glass or ceramic infused polymers. Such polymers may advantageously provide good strength, good elasticity, and good dielectric strength.

In some embodiments, the electrode has a width of about 0.15 inches to about 0.25 inches. In some embodiments, the electrode is about 0.2 inches to about 0.5 inches long. In some embodiments, the treatment element comprises steel (e.g., stainless, carbon, alloy). Steel may advantageously provide high strength while being low in cost and minimally reactive. In some embodiments, the electrodes or energy delivery elements described herein comprise materials such as platinum, gold, or silver. Such materials may advantageously provide high conductivity while being minimally reactive. In some embodiments, the electrodes or energy delivery elements described herein comprise anodized aluminum. Anodized aluminum may advantageously be highly stiff and low in cost. In some embodiments, the electrodes or energy delivery elements described herein comprise titanium which may advantageously possess a high strength to weight ratio and be highly biocompatible. In some embodiments, the electrodes or energy delivery elements described herein comprise nickel titanium alloys. These alloys may advantageously provide high elasticity and be biocompatible. Other similar materials are also possible.

As shown in the embodiment of FIG. 22G, the treatment element 532 further comprises a pin-shaped structure comprising a thermocouple 533 within an insulating bushing extending through a middle portion of the plate 532. In some embodiments, different heat sensors (e.g., thermistors) may be used. In some embodiments, the thermocouple 533 is configured to measure a temperature of the surface or subsurface of tissue to be treated or tissue near the tissue to be treated. A pin-shape having a sharp point may allow the structure to penetrate the tissue to obtain temperature readings from below the surface. The thermocouple can also be configured to measure a temperature of the treatment element 532 itself. The temperature measurements taken by the thermocouple can be routed as feedback signals to a control unit (e.g., the control unit 42 described with respect to FIG. 3) and the control unit can use the temperature measurements to adjust the intensity of energy being delivered through the electrode. In some embodiments, thermocouples or other sensing devices may be used to measure multiple tissue and device parameters. For example, multiple thermocouples or thermistors may be used to measure a temperature at different locations along the treatment element. In some embodiments, one of the sensors may be configured to penetrate deeper into the tissue to take a measurement of a more interior section of tissue. For example, a device may have multiple sensors configured to measure a temperature at the mucosa, the cartilage, and/or the treatment element itself. As described above, in some embodiments, the sensors described herein are configured to take a measurement of a different parameter. For example, tissue impedance can be measured. These measurements can be used to adjust the intensity and/or duration of energy being delivered through the treatment element. This type of feedback may be useful from both an efficacy and a safety perspective.

As shown in FIG. 22G, in some embodiments the thermocouple is within a pin shaped protrusion on the surface of the electrode 532. In other embodiments, the thermocouple can simply be on the surface of the electrode. In other embodiments, the thermocouple can protrude from the surface of the electrode in a rounded fashion. Rounded structures may be pressed into the tissue to obtain subsurface temperature readings. Other configurations and locations for the thermocouple are also possible. The use of thermocouples or temperature sensors may be applied not only to the embodiment of FIG. 22G, but also to any of the other embodiments described herein.

Figure 23A:
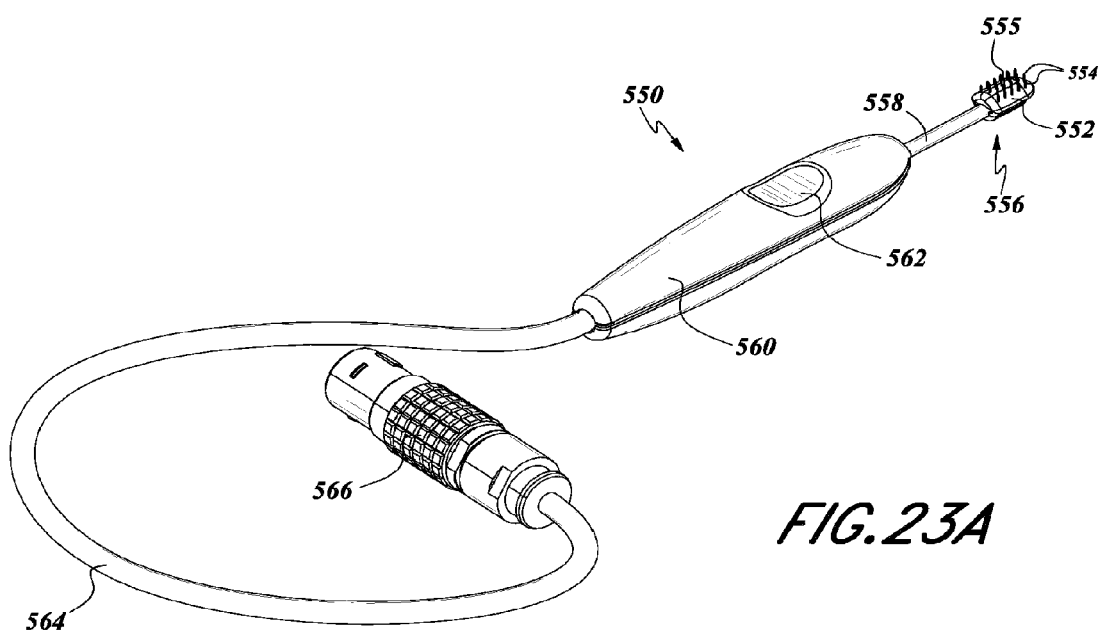
FIGS. 23A-23G illustrate an embodiment of a device for applying energy to the nasal valve area using an array of needle electrodes.
Figure 23B:
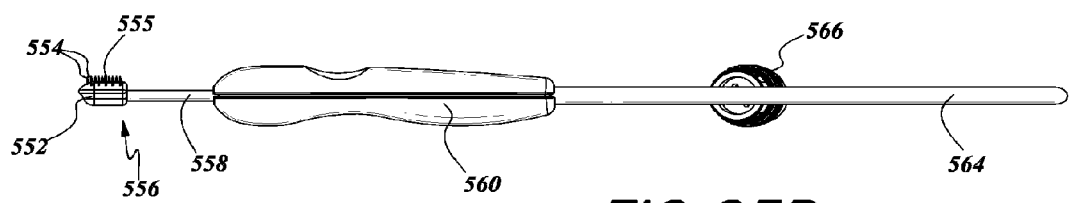
Figure 23C:
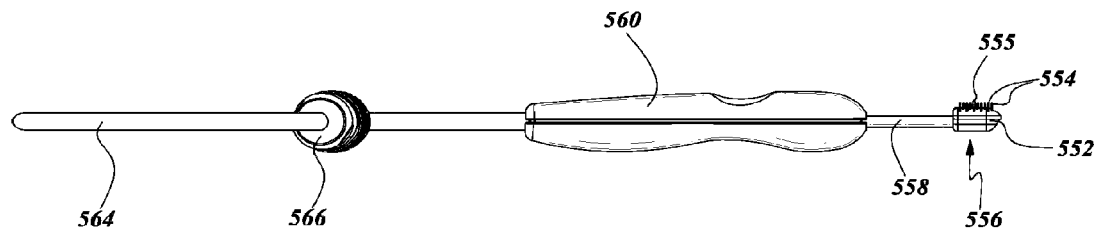
Figure 23D:
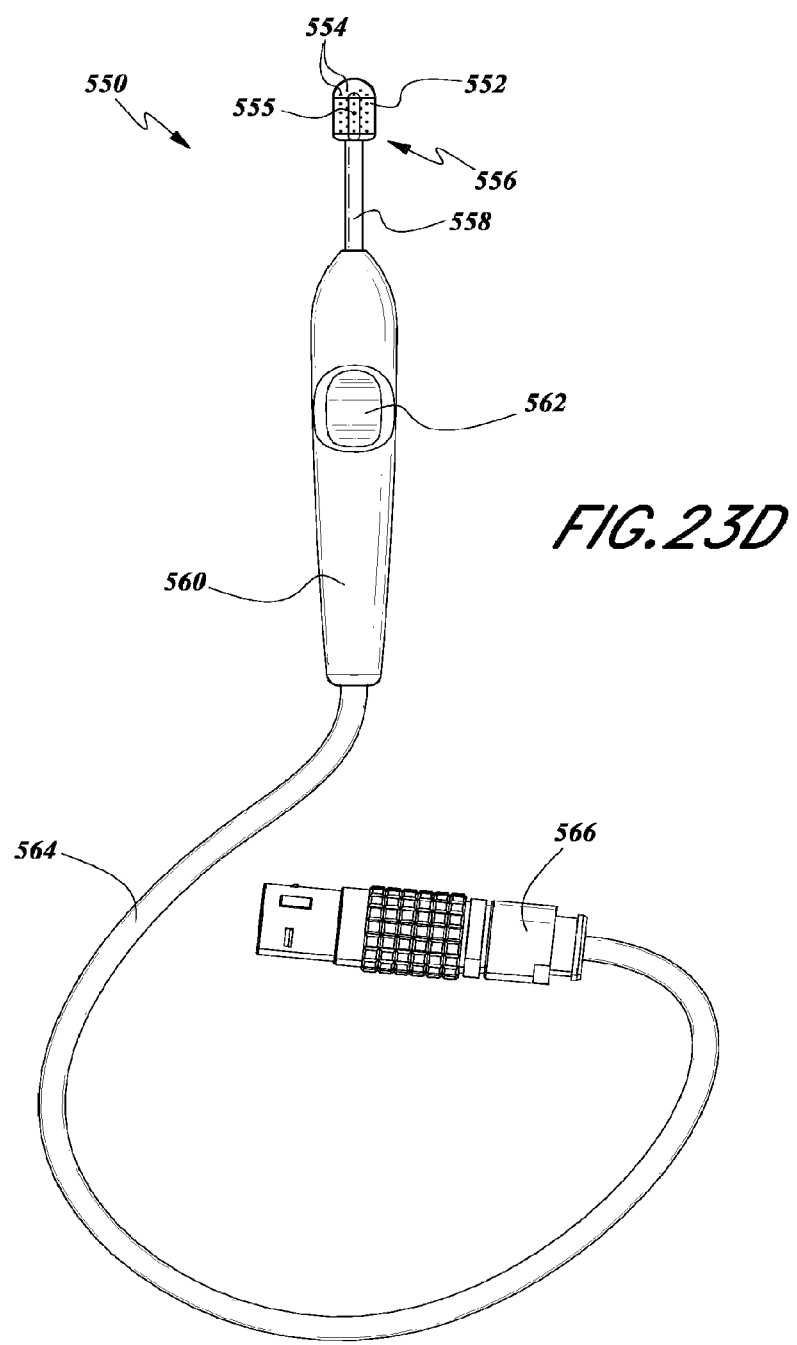
Figure 23E:
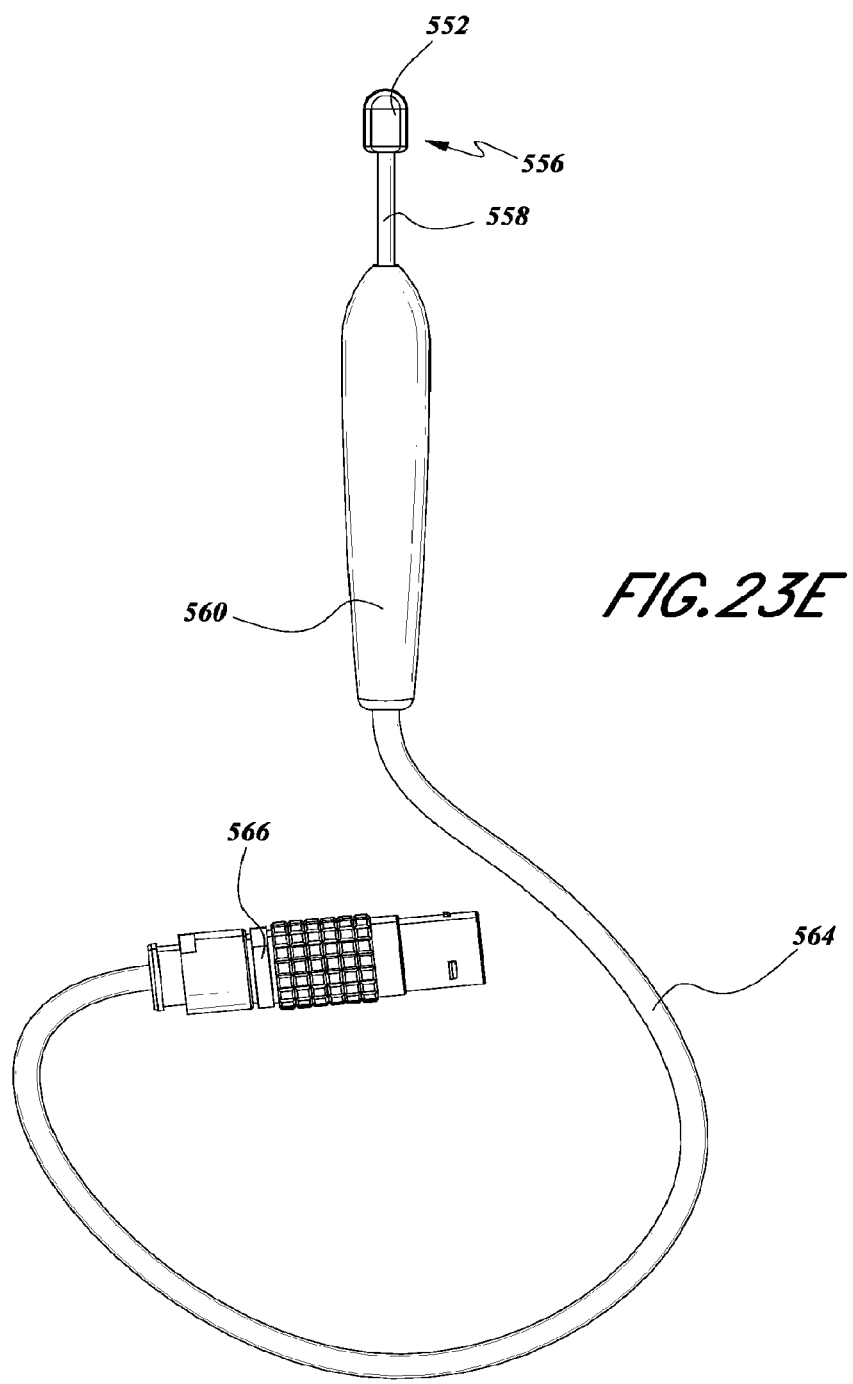
Figure 23F:
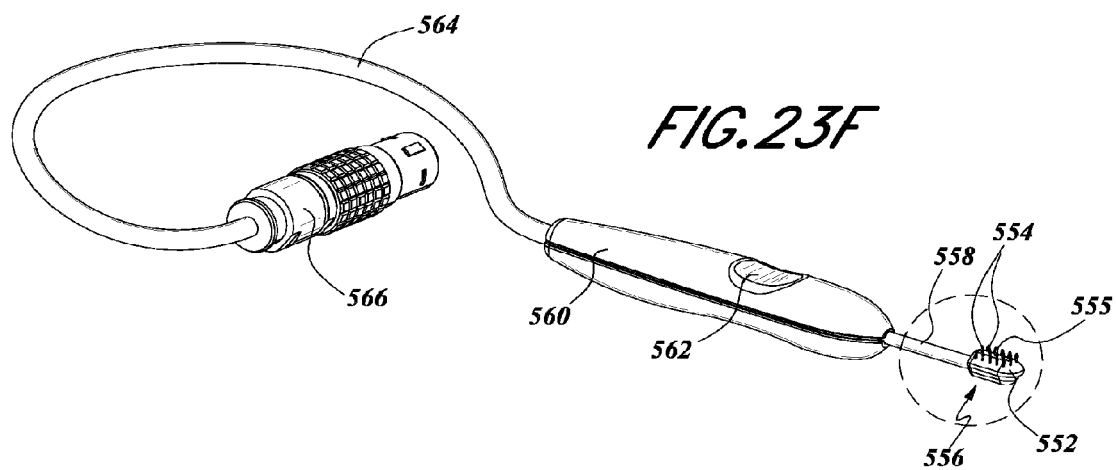

FIGS. 23A-G depict a treatment device 550 similar to the embodiments of FIGS. 8F and 18. FIGS. 23A and 23F are perspective views of the device 550 and show the device 550 comprising a treatment element 552 at the distal tip 556 of the device 550. The treatment element 552 may be provided on an enlarged distal tip 556 of an elongate shaft 558, and as in the embodiment illustrated, may have a convex shape configured to press against and create a concavity in the nasal valve cartilage (e.g., in upper lateral cartilage of the nasal valve). The distal tip 556 is located at a distal end of shaft 558. The shaft is attached at its proximal end to a handle 560. The handle 560 comprises an input control, such as a power button 562, on its front side that may be used to activate and deactivate the electrode. The power button may be positioned in a recess of the handle to allow for finger stability when activating and deactivating the electrode. In other embodiments, the input control is in the form of a switch or dial. Other configurations are also possible as described above. The device 550 may either comprise a generator or be connected to a remote generator. The device 550 may comprise a flexible wire or cable 564 that connects to an adaptor 566 that is configured to be plugged into a remote generator (not shown). The adaptor 566 may allow transmission of treatment energy between a remote generator and the device 550. The adaptor 566 may also allow transmission of any sensor signals between the device 550 and a generator or control unit. The treatment device 550 may be provided in a system or kit also including the remote generator. The system or kit (with or without the remote generator) may also include a grounding device and/or a cooling device as described above and further below. In some embodiments, the kit includes a positioning element (e.g., a "cottle" device) configured to help a user locate the optimal treatment area.

In some embodiments, the shaft has a width or diameter or about 0.235 inches to about 0.25 inches. In some embodiments, the shaft is about 1.5 inches to about 4 inches long. In some embodiments, the shaft and/or handle comprises a polymer such as polycarbonate or PEEK. In other embodiments, the shaft comprises stainless steel or other metals. The metals may be coated with an external and/or internal insulating coating (e.g., polyester, polyolefin, etc.). The handle may comprise the same material as the shaft, in some embodiments. In some embodiments, the shaft is rigid. This may allow a user of the device increased control over the deformation of nasal tissue. In some embodiments, the shaft comprises some amount of flexibility. This flexibility may allow a user adjust an angle of the distal tip by bending the distal end of the shaft.

FIGS. 23B and 23C depict side views of the device. As shown in FIGS. 23B and 23C, the handle 560 of the device 550 may comprise an indentation or recess around the middle of the handle 560. This may allow for enhanced grip and control when a user is holding the device. The indentation or recess may be near the input control or power button 562 to allow a user to easily activate and deactivate the device while holding it in a comfortable position.

FIGS. 23D and 23E depict front and back views of the device. As shown in FIGS. 23D and 23E, the handle 560 of the device generally comprises a rounded elongate shape. Other shapes are also possible. For example the device 550 may have a square shaped cross section. In some embodiments, a circumference (or width or cross-sectional area) of the handle 560 may increase distally along the length of the handle 560.

Figure 23G:
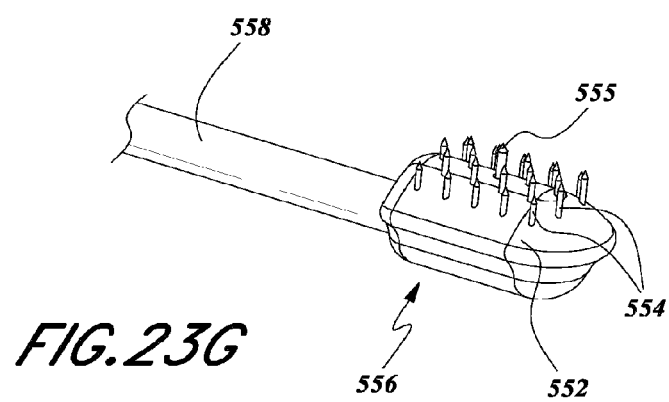

FIG. 23G depicts a larger view of the distal tip 556 of the device 550. As shown best in FIG. 23G, the treatment element 552 comprises a generally elongate shape. The front of the treatment element 552 comprises a shallow curved surface, providing a convex shape configured to deform the nasal tissue and create a concavity therein. In some embodiments, the front of the treatment element comprises a concave shape. The shape of the front surface of the treatment element may be selected to conform to the nasal tissue. The back surface of the treatment element 552 comprises a shallow curved surface along most of its length. As best seen in FIGS. 23B and 23C, the back surface narrows distally along the length of the element 552 from approximately the distal end of the needle electrodes to the distal tip of the treatment element 552. This shape may maximize visualization of the area to be treated, while, at the same time, providing sufficient rigidity for treatment. Other shapes are also possible. For example, the treatment element may comprise a generally spherical or cylindrical shape. In some embodiments, the treatment element comprises an angular shape (e.g., triangular, conical) which may allow for close conformation to the tissue structures. The treatment element 552 comprises a monopolar or bipolar needle array comprising multiple needles 554. In some embodiments, the needles 554 are energized in between select needles to deliver bipolar energy. In other embodiments, the energy is delivered between the needles (554) and a remote grounding pad (not shown). In some embodiments, the electrode needle pairs are arranged horizontally across the treatment element 552. In some embodiments, the electrode needle pairs are arranged vertically across the treatment element 552, or along the direction of the shaft 558 and handle 560. Other configurations are also possible. For example, the needle pairs may be arranged diagonally across the treatment element 552. The treatment element 552 may be placed either internally, with the needle pairs 554 positioned transmucosally or the treatment element 552 may be placed externally with the needle pairs 554 positioned transdermally. The distal tip 556 of the device 550 may also function as a mold or molding element. In a monopolar embodiment, the energy may be selectively delivered between certain sets of needles, all needles, or even individual needles to optimize the treatment effect.

The treatment element 552 of the device 550 further comprises a pin-shaped structure comprising a thermocouple 555 within an insulating bushing extending through a middle portion of the front surface of the treatment element 552. In some embodiments, different heat sensors (e.g., thermistors) may be used. As described above, in some embodiments, the thermocouple 555 is configured to measure a temperature of the surface or subsurface of tissue to be treated or tissue near the tissue to be treated. A pin-shape having a sharp point may allow the structure to penetrate the tissue to obtain temperature readings from below the surface. The thermocouple can also be configured to measure a temperature of the treatment element 552 itself. The temperature measurements taken by the thermocouple can be routed as feedback signals to a control unit (e.g., the control unit 42 described with respect to FIG. 3) and the control unit can use the temperature measurements to adjust the intensity of energy being delivered through the electrode. In some embodiments, thermocouples or other sensing devices may be used to measure multiple tissue and device parameters. For example, multiple thermocouples or thermistors may be used to measure a temperature at different locations along the treatment element. In some embodiments, one of the sensors may be configured to penetrate deeper into the tissue to take a measurement of a more interior section of tissue. For example, a device may have multiple sensors configured to measure a temperature at the mucosa, the cartilage, and/or the treatment element itself. As described above, in some embodiments, the sensors described herein are configured to take a measurement of a different parameter. For example, tissue impedance can be measured. These measurements can be used to adjust the intensity and/or duration of energy being delivered through the treatment element. This type of feedback may be useful from both an efficacy and a safety perspective.

In some embodiments, the treatment element has a width or diameter of about 0.25 inches to about 0.45 inches. In some embodiments, the treatment element is about 0.4 inches to about 0.5 inches long. The treatment element can, in some embodiments, comprise a ceramic material (e.g., zirconium, alumina, silicon glass). Such ceramics may advantageously possess high dielectric strength and high temperature resistance. In some embodiments, the treatment element comprises polyimides or polyamides which may advantageously possess good dielectric strength and elasticity and be easy to manufacture. In some embodiments, the treatment element comprises thermoplastic polymers. Thermoplastic polymers may advantageously provide good dielectric strength and high elasticity. In some embodiments, the treatment element comprises thermoset polymers, which may advantageously provide good dielectric strength and good elasticity. In some embodiments, the treatment element comprises glass or ceramic infused polymers. Such polymers may advantageously provide good strength, good elasticity, and good dielectric strength.

In some embodiments, the electrodes have a width or diameter of about 0.15 inches to about 0.25 inches. In some embodiments, the electrode is about 0.2 inches to about 0.5 inches long. In some embodiments, the treatment element comprises steel (e.g., stainless, carbon, alloy). Steel may advantageously provide high strength while being low in cost and minimally reactive. In some embodiments, the electrodes or energy delivery elements described herein comprise materials such as platinum, gold, or silver. Such materials may advantageously provide high conductivity while being minimally reactive. In some embodiments, the electrodes or energy delivery elements described herein comprise anodized aluminum. Anodized aluminum may advantageously be highly stiff and low in cost. In some embodiments, the electrodes or energy delivery elements described herein comprise titanium which may advantageously possess a high strength to weight ratio and be highly biocompatible. In some embodiments, the electrodes or energy delivery elements described herein comprise nickel titanium alloys. These alloys may advantageously provide high elasticity and be biocompatible. Other similar materials are also possible.

Energy applied to the tissue to be treated using any combination of the embodiments described in this application may be controlled by a variety of methods. In some embodiments, temperature or a combination of temperature and time may be used to control the amount of energy applied to the tissue. Tissue is particularly sensitive to temperature; so providing just enough energy to reach the target tissue may provide a specific tissue effect while minimizing damage resulting from energy causing excessive temperature readings. For example, a maximum temperature may be used to control the energy. In some embodiments, time at a specified maximum temperature may be used to control the energy. In some embodiments, thermocouples, such as those described above, are provided to monitor the temperature at the electrode and provide feedback to a control unit (e.g., control system 42 described with respect to FIG. 3). In some embodiments, tissue impedance may be used to control the energy. Impedance of tissue changes as it is affected by energy delivery. By determining the impedance reached when a tissue effect has been achieved, a maximum tissue impedance can be used to control energy applied.

In the embodiments described herein, energy may be produced and controlled via a generator that is either integrated into the electrode handpiece or as part of a separate assembly that delivers energy or control signals to the handpiece via a cable or other connection. In some embodiments, the generator is an RF energy source configured to communicate RF energy to the treatment element. For example, the generator may comprise a 460 KHz sinusoid wave generator. In some embodiments, the generator is configured to run between about 1 and 100 watts. In some embodiments, the generator is configured to run between about 5 and about 75 watts. In some embodiments, the generator is configured to run between about 10 and 50 watts.

In some embodiments, the energy delivery element comprises a monopolar electrode (e.g., electrode 535 of FIG. 22G). Monopolar electrodes are used in conjunction with a grounding pad. The grounding pad may be a rectangular, flat, metal pad. Other shapes are also possible. The grounding pad may comprise wires configured to electrically connect the grounding pad to an energy source (e.g., an RF energy source).

In some embodiments, the energy delivery element such as the electrodes described above can be flat. Other shapes are also possible. For example, the energy delivery element can be curved or comprise a complex shape. For example, a curved shape may be used to place pressure or deform the tissue to be treated. The energy delivery element may comprise needles or microneedles. The needles or microneedles may be partially or fully insulated. Such needles or microneedles may be configured to deliver energy or heat to specific tissues while avoiding tissues that should not receive energy delivery.

In some embodiments, the electrodes or energy delivery elements described herein comprise steel (e.g., stainless, carbon, alloy). Steel may advantageously provide high strength while being low in cost and minimally reactive. In some embodiments, the electrodes or energy delivery elements described herein comprise materials such as platinum, gold, or silver. Such materials may advantageously provide high conductivity while being minimally reactive. In some embodiments, the electrodes or energy delivery elements described herein comprise anodized aluminum. Anodized aluminum may advantageously be highly stiff and low in cost. In some embodiments, the electrodes or energy delivery elements described herein comprise titanium which may advantageously possess a high strength to weight ratio and be highly biocompatible. In some embodiments, the electrodes or energy delivery elements described herein comprise nickel titanium alloys. These alloys may advantageously provide high elasticity and be biocompatible. Other similar materials are also possible.

In some embodiments, the treatment elements (e.g., non-electrode portion of treatment element) of the devices described herein, including but not limited to FIGS. 8A-J, 9A-B, 10A-b, 11A-B, 12A-B, 13A-E, 14A-B, 15A-C, 16, 17A-B, 18, 22A-G, 19A-B, 20A-B, 21A-B, 22A-G, 23A-G, 25A-B, 26, 27, 28A-E, and 29, comprise an insulating material such as a ceramic material (e.g., zirconium, alumina, silicon glass). In some embodiments, the treatment elements comprise an insulating material interposed between multiple electrodes or electrode section. These insulating sections may provide an inert portion of the treatment element that does not delivery energy to the tissue. Such ceramics may advantageously possess high dielectric strength and high temperature resistance. In some embodiments, the insulators described herein comprise polyimides or polyamides which may advantageously possess good dielectric strength and elasticity and be easy to manufacture. In some embodiments, the insulators described herein comprise thermoplastic polymers. Thermoplastic polymers may advantageously provide good dielectric strength and high elasticity. In some embodiments, the insulators described herein comprise thermoset polymers, which may advantageously provide good dielectric strength and good elasticity. In some embodiments, the insulators described herein comprise glass or ceramic infused polymers. Such polymers may advantageously provide good strength, good elasticity, and good dielectric strength.

In some embodiments, the handle and/or shaft of the devices comprise the same materials as those described with respect to the insulators. In some embodiments, the handle and/or shaft of the device comprises a metal, such as stainless steel. In other embodiments, the handle and/or shaft of the device comprises a polymer, such as polycarbonate. Other metals and polymers are also contemplated.

In some embodiments, the device may be used in conjunction with a positioning element that can be used to aid in positioning of the device. The positioning element may be integrated into the device itself or can be separate. The positioning element may be used to determine the optimal placement of the device to achieve maximal increase in efficacy. In some embodiments, a positioning element is configured to be inserted and manipulated within the nose until the patient reports a desired improvement in breathing. The treatment device may then be used to treat while the positioning element is holding the nose in the desired configuration. In some embodiments, molds described herein may be used for the same purpose.

In some embodiments, a positioning element comprises a shaft comprising measurement marks indicating depth. For example, a physician may insert this element into the nose to manipulate the tissue to find the depth of treatment at which the patient reports the best breathing experience. The positioning element may comprise marks around the base of the shaft indicating which point of rotation of the device within the nostril provides the best breathing experience. The positioning element may also comprise marks indicating angle of insertion. The physician may then use the measurement marks to guide insertion of the treatment element to the same spot.

It will be appreciated that any combination of electrode configurations, molds, handles, connection between handles, and the like may be used to treat the nasal valve.

Cooling Systems

Embodiments of devices configured to heat specific tissue while maintaining lower temperatures in other adjacent tissue are provided. These devices may be incorporated into any of the treatment apparatuses and methods described herein. The nasal valve is an example of a tissue complex that includes adjacent tissues that may benefit from being maintained at different temperatures. Other examples include the skin, which comprises the epidermis, dermis, and subcutaneous fat, the tonsils, which comprise mucosa, glandular tissue, and vessels. Treatment of other tissue complexes is also possible. For example, in some embodiments, the internal structures of the nasal valve may be heated while maintaining a lower temperature in the mucosal lining of the nose and/or skin. In other embodiments, the mucosa may be heated, while maintaining lower temperatures in the skin. Limiting unwanted heating of non-target tissues may allow trauma and pain to be reduced, may reduce scarring, may preserve tissue function, and may also decrease healing time. Combinations of heat transfer and/or heat isolation may allow directed treatment of specific tissue such as cartilage, while excluding another tissue, such as mucosa, without surgical dissection.

Figure 24A:
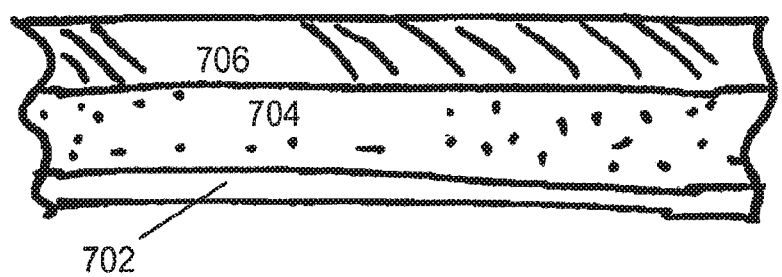
FIG. 24A depicts a cross-section of tissue at the nasal valve.
Figure 24B:
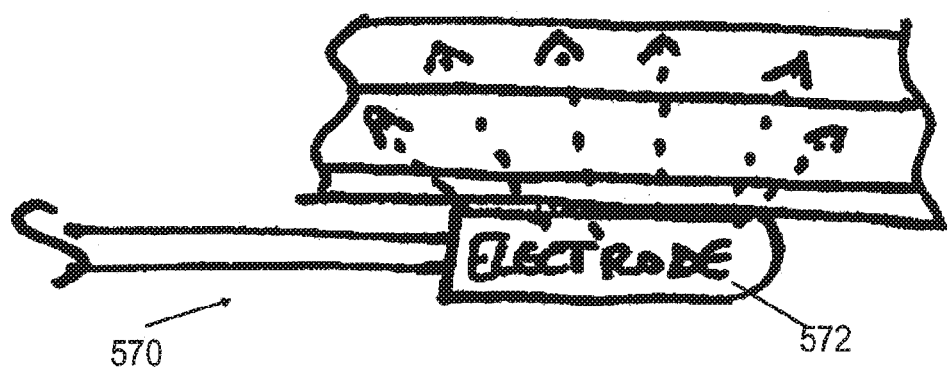
FIG. 24B depicts heat effects of RF treatment of tissue at the nasal valve.

Generally, when using a device 570 with an electrode 572 (e.g., monopolar RF electrode) to heat nasal cartilage, the electrode 572 must be in contact with the mucosa. FIG. 24A shows a cross-section of tissue at the nasal valve. The cross-section shows that the nasal cartilage 704 sits in between a layer of mucosa (internal) 702 and a layer of skin (external) 706. When the electrode 572 is activated, both the mucosa and the cartilage are heated by the current flowing from the electrode to the return (e.g., ground pad), as shown in FIG. 24B. The tissue closest to the electrode 572 receives the highest current density, and thus, the highest heat. A surface cooling mechanism may allow the temperature of the electrode surface to be reduced. Such a cooling mechanism may maintain a lower temperature at the mucosa even though current flow will continue to heat the cartilage.

Figure 25A:
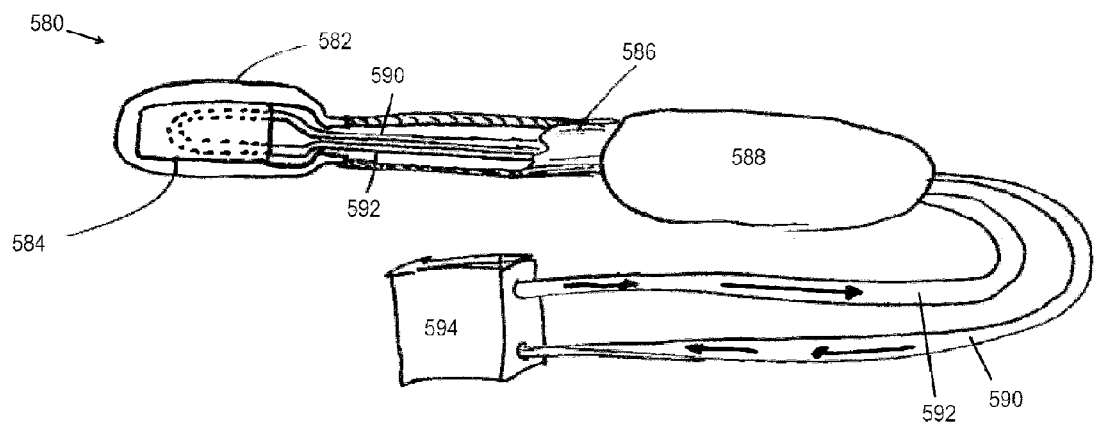
FIGS. 25A and 25B illustrate embodiments of devices for applying energy to the nasal valve area incorporating cooling systems.
Figure 25B:
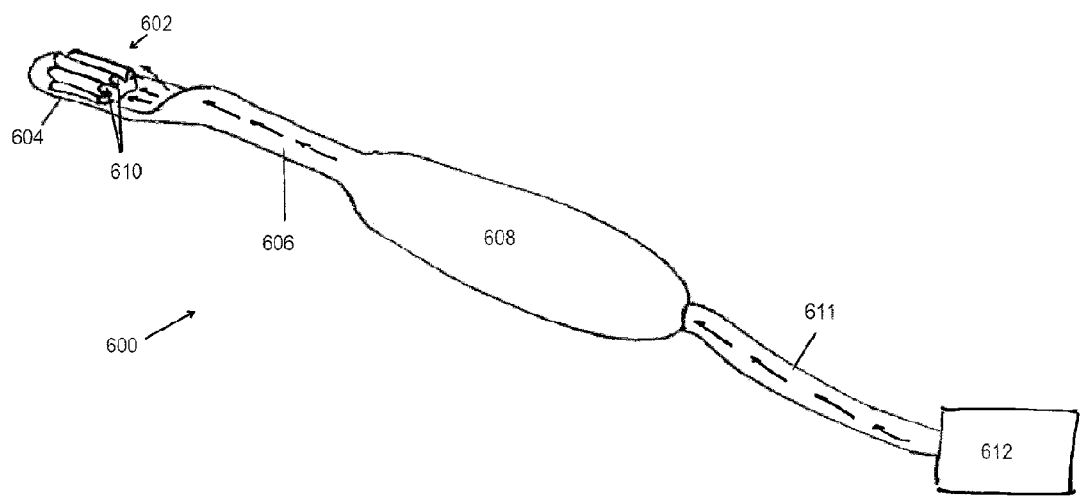

FIG. 25A depicts a device 580 configured to treat the nasal valve using an electrode while maintaining a reduced temperature at the mucosa. The device comprises a treatment element 582 comprising an electrode 584 at the distal tip of the device 580. The treatment element 582 is attached to a distal end of a shaft 586, which is attached to the distal end of a handle 588. Input and output coolant lines 590, 592 are attached to a pump and reservoir 594 and extend into the handle 588, through the distal end of the treatment element 582 to the electrode 582 and return back through the shaft 586 and handle 588 to the pump and reservoir 594. The coolant may be remotely cooled in the reservoir and may comprise a fluid or gas. The coolant flowing through the electrode 582 may allow the treatment element 582 to be maintained at a reduced temperature while still allowing current flow to heat the cartilage. Examples of coolant include air, saline, water, refrigerants, and the like. Water may advantageously provide moderate heat capacity and be non reactive. Refrigerants may advantageously be able to transfer significant amounts of heat through phase change. The coolant may flow through internal or external cavities of the electrode or wand tip. For example, FIG. 25B depicts an embodiment of a device 600 comprising a treatment element 602 with an electrode 604 at the distal tip of the device 600. The treatment element 602 is attached to the distal end of a shaft 606 which is attached to the distal end of a handle 608. The handle may be attached to a cable comprises a lumen or channel 611 through which gas or fluid may flow. The lumen 611 may diverge, near the treatment element 602, into separate external channels flowing over the electrode 604. The lumen 611 and channels 610 or cavities may be attached to a fan or fluid pump 612. In some embodiments, the fan or fluid pump may remotely cool the gas or fluid.

Figure 26:
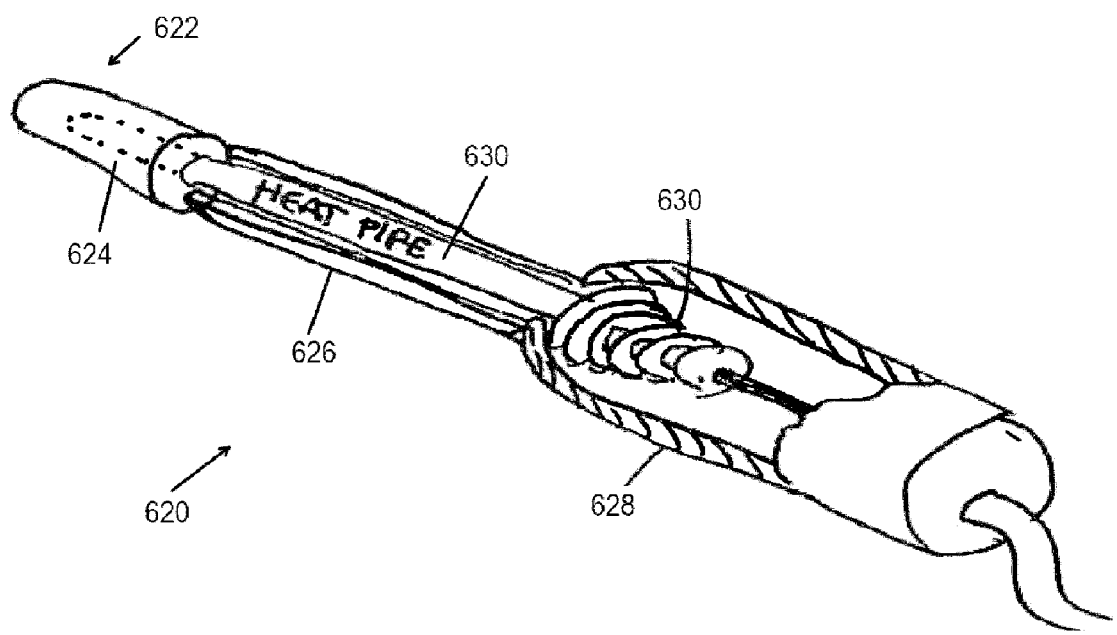
FIG. 26 shows an embodiment of a device for applying energy to the nasal valve area incorporating a heat pipe.

FIG. 26 depicts another embodiment of a device 620 configured to treat the nasal valve using an electrode 624 while maintaining a reduced temperature at the mucosa and/or skin. The device comprises a treatment element 622 comprising an electrode 624 at its distal end. The treatment element 622 is connected to the distal end of a shaft 626 which is connected to the distal end of a handle 628. The device 620 comprises a heat pipe 630 attached to the electrode 624 or treatment element 622. The heat pipe 630 is configured to transfer heat to a remote heat sink 632. As shown in FIG. 26, the heat sink 632 may be placed in the handle of the device. In some embodiments, the heat sink may be placed remotely. The heat pipe 630 may comprise a sealed tube (e.g., a copper tube) filled with a material that evaporates at a given temperature. When one end of the heat pipe 630 is heated, the fluid may evaporate and flow to the opposite end where it may condense and subsequently transfer heat to the heat sink 632. Using a material such as copper for the heat pipe 630 and/or heat sink 632 may advantageously provide high heat and electrical conductivity.

Figure 27:
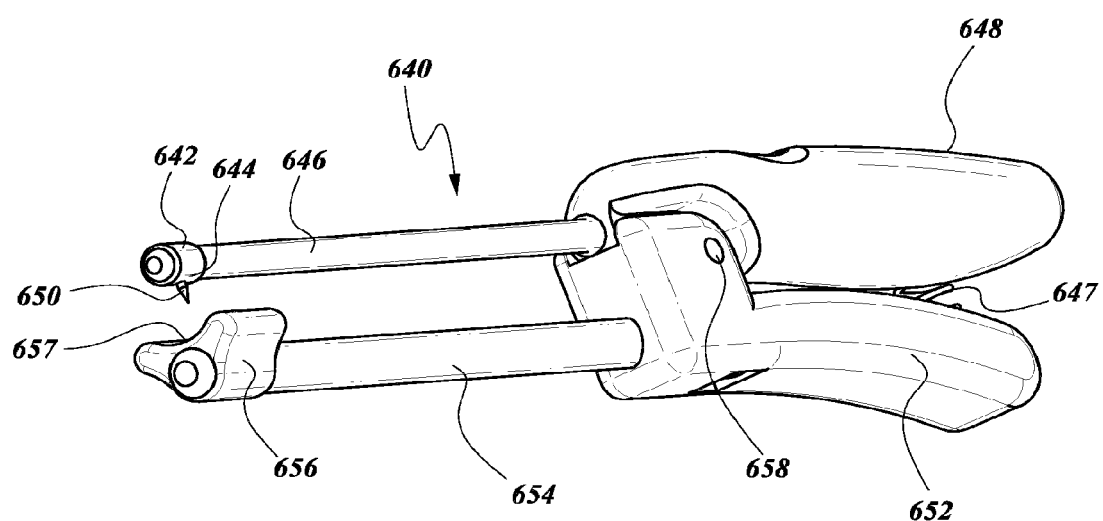
FIG. 27 depicts an embodiment of a device for applying energy to the nasal valve area incorporating heat pipes.

FIG. 27 depicts another embodiment of a device 640 configured to treat the nasal valve using a bipolar electrode pair while maintaining a reduced temperature at the skin. The device 640 comprises a first treatment element 642 comprising a first electrode 644 of a bipolar electrode pair at the distal end of a shaft 646. The treatment element 642 comprises a thermocouple pin 650 like that described with respect to FIG. 22G. The shaft 646 is connected to the distal end of a handle 648. The handle 648 is connected to another handle 652 comprising a shaft 654 with a treatment element 656 at its distal tip. The treatment element 656 comprises a second electrode 657 of the bipolar electrode pair. The first and second treatment elements 642, 656 can be placed on either side of nasal tissue. For example, the first treatment element 642 may be in contact with the mucosa and the second treatment element 656 may be in contact with the skin. Similar to the device depicted in FIG. 26, the device of FIG. 27 comprises a heat pipe within both shafts 654, 646. Thus heat from the tissue is transferred from the treatment elements 642, 656 and is transported down the shafts 654, 646 into an integrated or a remote heat sink (not shown). This heat transfer may keep the skin and the mucosa relatively cool while still delivering sufficient treatment energy to the cartilage. The connection 658 and spring 647 between the two handles 648, 652 is configured to bias the two shafts 646, 654 and treatment elements 642, 656 towards a collapsed state. Squeezing the handles 648, 652 may separate the two shafts 646, 654 and treatment elements 642, 656. Thus, the handles 648, 652 can be squeezed to properly position the device 640 at the nasal tissue to be treated. Releasing the handles 648, 652 can cause the treatment element 642 and the cooling element 656 to contact the tissue. In some embodiments, the device 640 may only comprise one heat pipe. In some embodiments, the device 640 may comprise a treatment element with a monopolar electrode on one shaft and a molding element on the other shaft. Multiple configurations are contemplated. For example, the device may comprise one heat pipe and a bipolar electrode pair. For another example, the device may comprise one heat pipe and a monopolar electrode. For another example, the device may comprise two heat pipes and a monopolar electrode. Other device configurations are also possible.

The embodiments described with respect to FIGS. 25A-27 employ specific differential cooling mechanisms to maintain different and particular temperatures in adjacent tissues. FIGS. 28A-28E depicts various examples of more general mechanisms configured to maintain different temperatures in adjacent tissues. FIGS. 28A-28E depict examples of differential cooling mechanisms as applied to a cross-section of tissue at the nasal valve, like that shown in FIG. 24A.

Figure 28A:
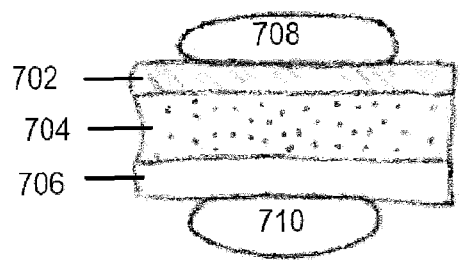
FIGS. 28A-28E depict embodiments of differential cooling mechanisms.

As shown in FIG. 28A, in some embodiments, the differential cooling mechanism comprises two elements: a first element 708 and a second element 710. The two elements are on either side of the thickness of the nasal tissue. In one embodiment, the mechanism is configured to maintain normal temperatures in the cartilage 704 while cooling the mucosa 702 and the skin 706. In such an embodiment, the first and second elements 708, 710 comprise a cooling apparatus such as those described above (e.g., heatsink, coolant lines, etc.). In some embodiments, the mucosa 702 and the skin 706 are heated while normal temperatures are maintained in the cartilaginous middle layer 704. The cartilage 704 may be somewhat warmed, in such embodiments, but may be cooler than the mucosa 702 and the skin 706. In such embodiments, the first and second elements 708, 710 comprise a heating apparatus, such as radio frequency electrodes or resistive heating elements. In some embodiments, the mucosa 702 is heated, the skin 706 is cooled, and normal temperatures are maintained in the cartilage 704. In such embodiments, the first element 708 comprises a heating apparatus and the second element 710 comprises a cooling apparatus. For example, the device 580, described with respect to FIG. 27, may use such a mechanism. In some embodiments, the skin 706 is heated, the mucosa 702 is cooled, and normal temperatures are maintained in the cartilage 704. In such embodiments, the first element 708 comprises a cooling apparatus and the second element 710 comprises a heating apparatus. Again, the device 580, described with respect to FIG. 27, is an example of a device that may use such a mechanism.

Figure 28D:
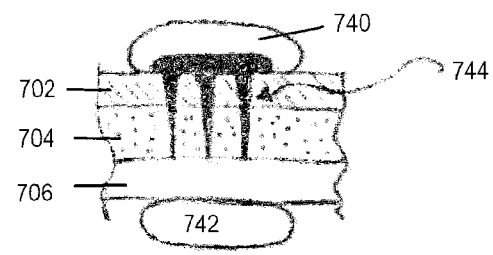
Figure 28B:
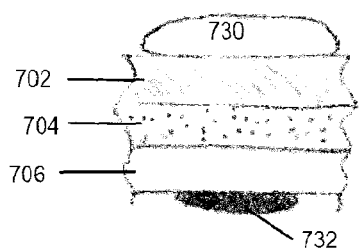

FIG. 28B shows an example of one of the embodiments described with respect to FIG. 28A. The first element 730 is on the mucosal surface 702. The second element 732 is an energy delivery element and is positioned on the skin side 706 of the tissue thickness. The first element 730 comprises a cooling apparatus and the second element 732 comprises an energy delivery element (e.g., an RF electrode). The mucosal layer 702 is cooled while the skin 706 and cartilaginous areas 704 are heated. In other embodiments, the first element 730 can be positioned on the skin 706 and the second element 732 can be positioned on the mucosa 702. In such embodiments, the skin 706 is cooled while the mucosa 702 and the cartilage 704 are heated.

Figure 28E:
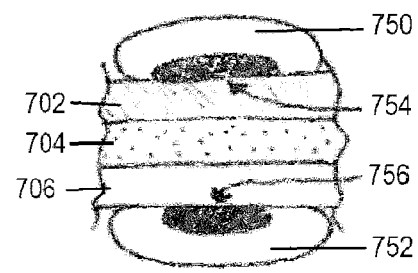
Figure 28C:
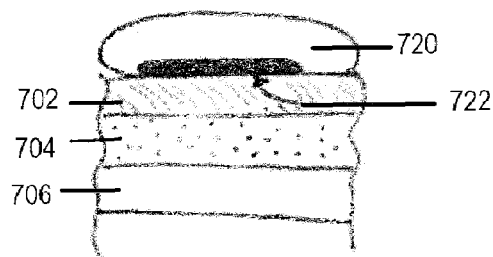

As shown in FIG. 28C, in some embodiments, the differential cooling mechanism comprises a first element 720 and a second element 722. Both elements 720, 722 are on the mucosa 702 side of the tissue thickness. In some embodiments, the mucosal layer 702 is cooled while higher temperatures are maintained in the middle cartilaginous layer 704. In such embodiments, the first element 720 comprises a cooling apparatus, and the second element 722 comprises an energy delivery apparatus (e.g., a monopolar radiofrequency electrode). In some embodiments, the first element 720 is sufficiently efficient to maintain cool temperatures at the mucosa 702 despite the energy provided by the second element 722. In other embodiments, the first and second elements 720, 722 are both positioned on the skin side 706 of the tissue thickness. In such embodiments, the skin 706 is cooled while higher temperatures are maintained in the middle cartilaginous layer.

As shown in FIG. 28D, in some embodiments, the differential cooling mechanism comprises a first surface element 740 and a second surface element 742 on either side of the tissue thickness. A third subsurface element 744 is engaged through the mucosa 702 and into the cartilage area 704. In some embodiments, the mucosa 702 and the skin 706 are cooled while the middle cartilaginous layer 704 is heated. In such embodiments, the first and second elements 740, 742 comprise cooling apparatus while the third element 744 comprises a heating element (e.g., RF monopolar electrode, RF bipolar needles, etc.). In other embodiments, the third subsurface element 744 may be engaged through the skin 706 and into the cartilage area 704.

As shown in FIG. 28E, in some embodiments, the differential cooling mechanism comprises a first surface element 750 and a second surface element 752 on either side of the tissue thickness. The differential cooling mechanism further comprises a third surface element 754 and a fourth surface element 756 on either side of the tissue thickness. In some embodiments, the cartilage layer 704 is heated while the mucosa 702 and the skin 706 are cooled. In such embodiments, the first and second elements 750, 752 comprise cooling apparatus and the third and fourth elements 754, 756 comprise energy delivery apparatuses (e.g., bipolar plate electrodes). In some embodiments, the cartilage 704 and mucosal 702 layers are heated while the skin 706 is cooled. In such embodiments, the first element 750 comprises a heating apparatus; the second element 752 comprises a cooling apparatus; and the third and fourth elements 754, 756 comprise energy delivery apparatuses. It will be appreciated that different differential temperature effects can be achieved by reconfiguring and adding or subtracting to the described configuration of elements.

Figure 29:
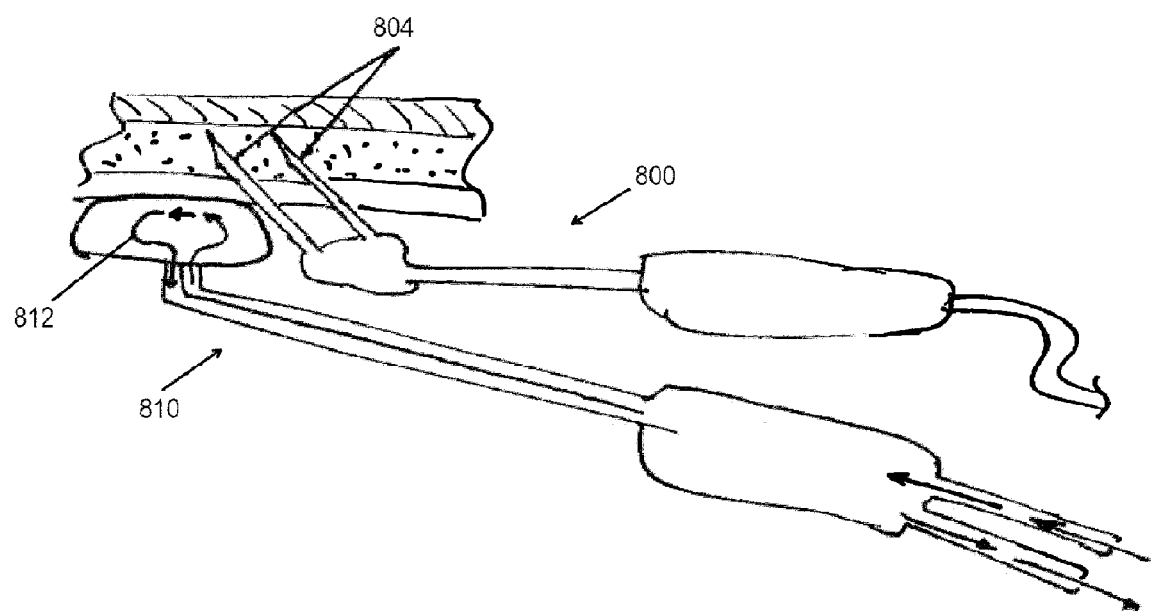
FIG. 29 shows an embodiment of a system comprising a device for applying energy to the nasal valve area with electrode needles and a separate cooling mechanism.

Cooling occurring before, during, or after treatment may effect reduced temperature of the skin and/or mucosa. In some embodiments, attaching passive fins or other structures to the electrode or wand tip may allow for heat dissipation to the surrounding air. In some embodiments, the device may be configured to spray a cool material such as liquid nitrogen before, during, or after treatment. Using a material such as copper for the passive fins or other structure may advantageously provide high heat and electrical conductivity. In some embodiments, using metals with a high heat capacity in the device (e.g., in the energy delivery element, the re-shaping element, or both) may advantageously provide the ability to resist temperature change during energy delivery. In some embodiments, pre-cooling the electrode (e.g., by refrigeration, submersion, spraying with a cool substance like liquid nitrogen, etc.) may maintain a reduced temperature at the mucosa. Any combination of the cooling methods described herein may be used in conjunction with any of the energy delivery methods described herein (e.g., bipolar RF electrodes, arrays needles, plates, etc.). For example, FIG. 29 depicts an embodiment of a device 800 comprising a treatment element 802 comprising electrode needles 804 at its distal tip. The device 800 may be used in conjunction with a separate cooling device 810 which may comprise channels 812 or cavities to circulate air or fluid. The independent cooling device 810 may, in other embodiments, employ a different cooling mechanism.

In embodiments using laser energy to heat cartilage, it is possible to use a combination of two or more lasers whose beams converge at a location within the target tissue. This convergence may cause more heat at that junction as compared to locations where only a single beam is acting. The junction may be controlled manually or via computer control. Specific treatment may be provided.

In some embodiments, insulating material may be used to protect non-target tissue during energy delivery. For example, an electrode needle may be preferentially insulated on a portion of the needle that is in contact with non-target tissue. For another example, flat electrode blades may be insulated on a portion of the blade that is in contact with non-target tissue. Other configurations for heat isolation are also possible.

Any of the cooling mechanisms or combinations of the cooling mechanisms described herein may be used in conjunction with any of the devices or combinations of devices described herein, or the like.

Examples of Methods of Treatment

Embodiments of methods for treating nasal airways are now described. Such methods may treat nasal airways by decreasing the airflow resistance or the perceived airflow resistance at the site of an internal or external nasal valve. Such treatments may also address related conditions, such as snoring.

In one embodiment, a method of decreasing airflow resistance in a nasal valve comprises the steps of inserting an energy-delivery or cryo-therapy device into a nasal passageway, and applying energy or cryo-therapy to a targeted region or tissue of the nasal passageway. For example, in some embodiments, the method may include delivering energy or cryo-therapy to a section of internal nasal valve cartilage in the area of the upper lateral cartilage, or in the area of intersection of the upper and lower lateral cartilage. In alternative embodiments, the method may deliver energy to the epithelium, or underlying soft tissue adjacent to the upper lateral cartilage and/or the intersection of the ULC and the LLC.

In another embodiment, a method comprises heating a section of nasal valve cartilage to be re-shaped, applying a mechanical re-shaping force, and then removing the heat. In some embodiments, the step of applying a mechanical re-shaping force may occur before, during or after the step of applying heat.

In some embodiments, the method may further include the step of inserting a re-shaping device into the nasal passageway after applying an energy or cryo-therapy treatment. In such embodiments, a re-shaping device such as an external adhesive nasal strip (such as those described for example in U.S. Pat. No. 5,533,499 to Johnson or U.S. Pat. No. 7,114,495 to Lockwood, the entirety of each of which is hereby incorporated by reference) may be applied to the exterior of the nose after the treatment in order to allow for long-term re-shaping of nasal valve structures as the treated tissues heal over time. In alternative embodiments, a temporary internal re-shaping device (such as those taught in U.S. Pat. No. 7,055,523 to Brown or U.S. Pat. No. 6,978,781 to Jordan, the entirety of each of which is hereby incorporated by reference) may be placed in the nasal passageway after treatment in order to allow for long-term re-shaping of nasal valve structures as the treated tissues heal over time. In some embodiments, the dilating nasal strips can be worn externally until healing occurs.

In alternative embodiments, internal and/or external re-shaping devices may be used to re-shape a nasal valve section prior to the step of applying energy or cryo-therapy treatments to targeted sections of the epithelial, soft tissue, mucosa, submucosa and/or cartilage of the nose. In some embodiments, the energy or cryo-therapy treatment may be configured to change the properties of treated tissues such that the tissues will retain the modified shape within a very short time of the treatment. In alternative embodiments, the treatment may be configured to re-shape nasal valve structures over time as the tissue heals.

In some embodiments, a portion of the nose, the nasal valve and/or the soft tissue and cartilage of the nasal valve may be reshaped using a re-shaping device and then fixed into place. In some embodiments, such fixation may be achieved by injecting a substance such as a glue, adhesive, bulking agent or a curable polymer into a region of the nasal tissue adjacent the target area. Alternatively, such a fixation substance may be applied to an external or internal surface of the nose.

In some embodiments, an injectable polymer may be injected into a region of the nose, either below the skin on the exterior of the nose, or under the epithelium of the interior of the nose. In some embodiments, an injectable polymer may include a two-part mixture configured to polymerize and solidify through a purely chemical process. One example of a suitable injectable two-part polymer material is described in US Patent Application Publication 2010/0144996, the entirety of which is hereby incorporated by reference. In other embodiments, an injectable polymer may require application of energy in order to cure, polymerize or solidify. A re-shaping device may be used to modify the shape of the nasal valve before or after or during injection of a polymer. In embodiments employing an energy-curable polymer, a re-shaping device may include energy-delivery elements configured to deliver energy suitable for curing the polymer to a desired degree of rigidity.

In another embodiment, the soft tissue of the upper lip under the nares may be debulked or reshaped to reduce airflow resistance. In some embodiments, such re-shaping of the upper lip soft tissue may be achieved by applying energy and/or cryotherapy from an external and/or internal treatment element. In some embodiments, the tissue of the upper lip under the nares may be compressed by an internal or external device prior to or during application of the energy or cryo-therapy. For example, devices such as those shown in FIGS. 5A and 5B may be adapted for this purpose by providing tissue-engaging clamp tips shaped for the purpose.

In another embodiment, the muscles of the nose and/or face are stimulated to dilate the nasal valve area prior to or during application of other treatments such as energy/cryo application or fixation treatments. In such embodiments, the muscles to be treated may include the nasal dilator muscles (nasalis) the levator labii, or other facial muscles affecting the internal and/or external nasal valves. In some embodiments, the targeted muscles may be stimulated by applying an electric current to contract the muscles, mentally by the patient, or manually by the clinician.

In some embodiments, the muscles of the nose and/or face may also be selectively deactivated through chemical, ablative, stimulatory, or mechanical means. For example, muscles may be deactivated by temporarily or permanently paralyzing or otherwise preventing the normal contraction of the muscle tissue. Chemical compounds for deactivating muscle tissues may include botulinum toxin (aka "botox"), or others. Ablative mechanisms for deactivating muscle tissue may include RF ablation, laser ablation or others. Mechanical means of deactivating muscle tissues may include one or more surgical incisions to sever targeted muscle tissue.

In another embodiment, the tissue of the nasal valve may be reshaped by applying energy to the internal and external walls of the nasal valve using a clamp like device as illustrated for example in FIGS. 5A and 5B. One arm of the clamp may provide inward pressure to the external, skin side tissue covering the nasal valve and the other side of the clamp may provide outward pressure to the mucosal tissue on the lateral wall of the nasal airway above the ULC and LLC or both.

In some embodiments, energy may be applied to the skin of the nose to effect a shrinkage of the skin, epidermis, dermis, subdermal, subcutaneous, tendon, ligament, muscle, cartilage and/or cartilage tissue. The tissue shrinkage is intended to result in a change of forces acting on the tissues of the nasal valve to improve airflow through the nasal airway.

In another embodiment, the nasal valve tissue may be damaged or stimulated by energy application, incisions, injections, compression, or other mechanical or chemical actions. Following such damage, a device may be used on the tissue to mold or shape the tissue of the valve during healing. In some embodiments, such a re-shaping device may be temporarily placed or implanted inside or outside the patient's nose to hold a desired shape while the patient's healing process progresses.

In another embodiment, the aesthetic appearance of the nose may be adjusted by varying the device design and/or treatment procedure. The predicted post-procedure appearance of the nose may be shown to the patient through manipulating the nasal tissue to give a post procedure appearance approximation. The patient may then decide if the predicted post procedure appearance of the face and nose is acceptable or if the physician needs to change parameters of the device or procedure to produce an appearance more acceptable to the patient.

In another embodiment, reduction of the negative pressure in the nasal airway can be effected to reduce collapse of the structures of the nasal airway on inspiration without changing a shape of the nasal valve. For example, this may be accomplished by creating an air passage that allows flow of air directly into the site of negative pressure. One example of this is creating a hole through the lateral wall of the nose allowing airflow from the exterior of the nose through the nasal wall and into the nasal airway.

In another embodiment, energy, mechanical or chemical therapy may be applied to the tissue of the nasal airway with the express purpose of changing the properties of the extracellular matrix components to achieve a desired effect without damaging the chondrocytes or other cells of the nasal airway tissue.

In some embodiments, devices (e.g., devices like those described with respect to FIGS. 9A-21B) may be used to provide tissue re-shaping/molding and to impart energy to the nasal valve. The electrode may be placed in contact with the target nasal valve tissue. The electrodes and molds may be moved to shape the tissue as necessary to achieve improvement in nasal airway. The electrodes may be activated while the tissue is deformed in the new shape to treat the tissue. The electrode may then be deactivated and the device may be removed from the nasal valve area.

FIGS. 30A-30D depict a method for using a device 900 similar to those devices described above, including but not limited to FIGS. 8A, 9B, 18, 22A-G, and 23A-G, to provide tissue re-shaping/molding and to impart energy to tissue near the nasal valve.

The method may include identifying a patient who desires to improve the airflow through their nasal passageways and/or who may benefit from an increase in a cross-sectional area of the opening of the nasal valve. The patient may be positioned either in an upright position (e.g., seated or standing) or be lying down. Local anesthesia may be applied to an area near or surrounding the tissue to be treated. General anesthesia may also be used.

Optionally, a positioning element, like that described herein, may be used to measure a desired depth or angle of treatment. As described above, the positioning element may be inserted to the desired depth of treatment and rotated to a desired angle of treatment. Marks along the positioning element can indicate the desired depth. Marks along the base of the shaft of the positioning element can indicate the desired angle. The physician or other medical professional administering the treatment can then insert the treatment device to the desired location. The physician may also assess any other characteristics relevant to the treatment of the patient's nose that may influence the manner of treatment. In some embodiments, a re-shaping element may be used to manipulate the nasal tissue into a configuration allowing improved airflow; and treatment may be performed while such a re-shaping element is maintaining the desired configuration of the nasal tissue.

If the treatment device comprises a monopolar electrode or electrode needles, a ground pad may be attached to the patient. The ground pad may be attached at the patient's torso, for example the shoulder or abdomen. Other locations are also possible, such as the patient's buttocks. Preferably, the point of attachment is a large, fleshy area. After being attached, the ground pad may be plugged into a power source. If the device is powered by a remote generator (e.g., RF generator), the device may then be plugged into the generator.

Figure 30A:
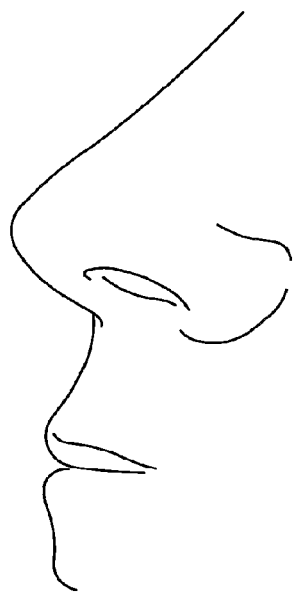
FIG. 30A-30D shows an embodiment of a method for applying energy to the nasal valve area using.
Figure 30B:
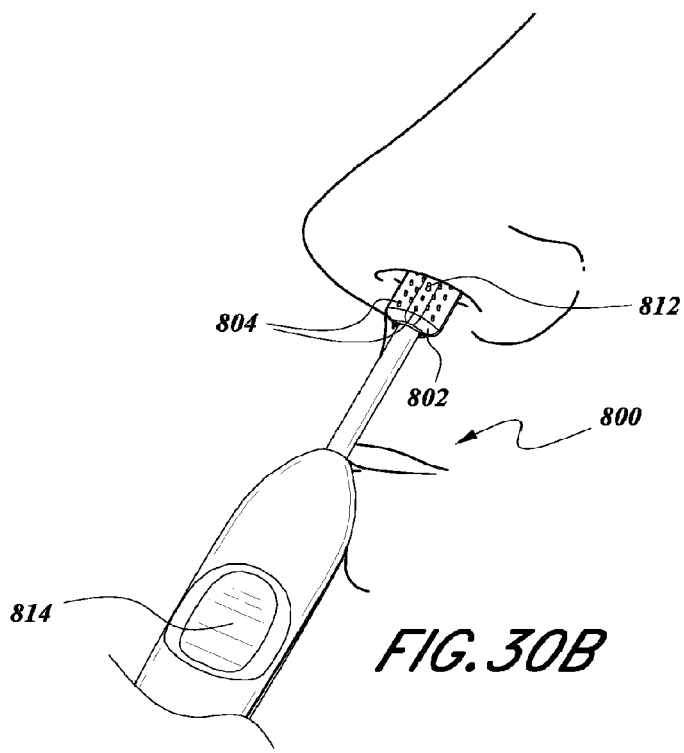
Figure 30C:
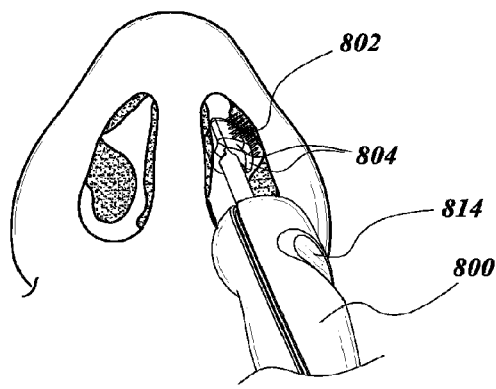

FIG. 30A depicts the nose of a patient prior to insertion of the device. As shown in FIG. 30B, the device is then inserted into a nostril of the patient. The treatment element 802 of the device 800 may be positioned within the nasal airway, adjacent to nasal tissue (e.g., upper lateral cartilage) to be treated. The treatment element 802 may be positioned so that the electrode is in contact with the tissue to be treated. The device 800 (as shown in FIG. 30C) comprises multiple needle electrodes 804. The needle electrodes 804 may be inserted so that they are penetrating or engaging tissue to be treated.

Figure 30D:
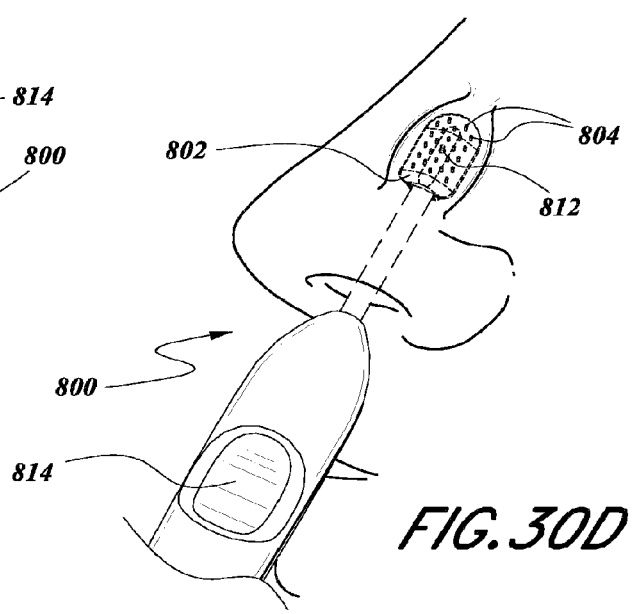

The treatment element 802 may be used to deform the nasal tissue into a desired shape by pressing a convex surface of the treatment element 802 against the nasal tissue to be treated. FIG. 30C shows an internal view, from the nares, of the treatment element 802 pushing against the upper lateral cartilage 806 of the nose, deforming the upper lateral cartilage 806 and increasing the area of the opening of the nasal valve 808. FIG. 30D depicts an external view of the treatment element 802 deforming the upper lateral cartilage 806. Even from the outside, the nose appears to be bulging near the area to be treated. In some embodiments, the deformation required to treat the nose is not visually detectable. A control input such as button 814 may be used to activate the electrode and deliver energy (e.g., RF energy) to the tissue to be treated.

In some embodiments, temperature of the area around the electrode during treating is from about 30.degree. C. to about 90.degree. C. In some embodiments, temperature of the area around the electrode during treating is from about 40.degree. C. to about 80.degree. C. In some embodiments, temperature of the area around the electrode during treating is from about 50.degree. C. to about 70.degree. C. In some embodiments, temperature of the area around the electrode during treating is about 60.degree. C. In some embodiments, for example during cryo-therapy, temperature of the area around the electrode may be lower.

In some embodiments, treating the target tissue comprises treatment for about is to about 3 minutes. In some embodiments, treating the target tissue comprises treatment for about 10 s to about 2 minutes. In some embodiments, treating the target tissue comprises treatment for about 15 s to about 1 minute. In some embodiments, treating the target tissue comprises treatment for about 20 s to about 45 s. In some embodiments, treating the target tissue comprises treatment for about 30 s.

In some embodiments, treating the target tissue comprises delivering between about 1 and about 100 watts to the tissue. In some embodiments, treating the target tissue comprises delivering between about 5 and about 75 watts to the tissue. In some embodiments, treating the target tissue comprises delivering between about 10 and about 50 watts to the tissue.

As shown in FIGS. 30B and 30D, a thermocouple 812 may be provided on the electrode (e.g., as described with reference to FIGS. 22G and 27). In some embodiments, more than one thermocouple may be provided. For example, in embodiments comprising more than one electrode or electrode pair, each electrode or electrode pair may comprise a thermocouple. The thermocouple 812 may monitor temperature of the electrode and provide feedback to a control unit (e.g., control system 42 described with respect to FIG. 3). The control unit may use the data from the thermocouple 812 to regulate temperature and auto-shutoff once treatment has been achieved or in the case of an overly high temperature.

After treating the tissue, the device 800 may be removed from the nostril. If a grounding pad is used, the grounding pad may be detached from the patient.

In some embodiments, differential cooling mechanisms may be used to treat the nasal valve using electrodes or other energy delivery elements while maintaining a reduced temperature at the skin and/or mucosa. For example, devices like those described with respect to FIG. 25A-27 or devices employing the differential cooling mechanisms described with respect to FIGS. 28A-28E may be used. The cooling system may be activated. The device may then be inserted into the nose and placed in contact with the nasal vale. The device may then be activated. Activation of the device may cause an increase in the cartilage temperature while minimizing the temperature increase in the skin and/or mucosa. The device may then be deactivated and removed from the nose.

In some embodiments, devices may be used in which insulating material is used to protect non-target tissue during energy delivery. In an embodiment, a device comprises an electrode needle preferentially insulated on a portion of the needle. The needle may be inserted into the cartilage so that the insulated portion is in contact with the mucosa and/or the skin and the non-insulated portion is in contact with the cartilage. The device may be activated, causing an increase in the cartilage temperature while minimizing temperature increase in the skin and/or mucosa. The device may be deactivated and removed from the nose.

Although this invention has been disclosed in the context of certain preferred embodiments and examples, it will be understood by those skilled in the art that the present invention extends beyond the specifically disclosed embodiments to other alternative embodiments and/or uses of the invention and obvious modifications and equivalents thereof. Thus, it is intended that the scope of the present invention herein disclosed should not be limited by the particular disclosed embodiments described above, but should be determined only by a fair reading of the claims that follow.

What is claimed is:

1. A method of modifying a property of nasal tissue of or near a nasal valve, without using a surgical incision or an implant, to decrease airflow resistance or perceived airflow resistance in a nasal airway, the method comprising:
   positioning a treatment surface within a nasal airway adjacent to a nasal tissue to be treated;
   applying the treatment surface to the nasal tissue with sufficient force to alter a shape of the nasal tissue; and
   applying energy to, or removing energy from, the nasal tissue with a non-penetrating treatment element disposed on the treatment surface, to change the property of the nasal tissue, wherein the nasal tissue at least partially maintains the changed property after the treatment element is removed and the nasal tissue heals, thereby decreasing airflow resistance or perceived airflow resistance in the nasal airway.

2. The method of claim 1, wherein applying energy comprises applying energy in a form selected from the group consisting of ultrasound, microwave, heat, radiofrequency, electrical, light and laser.

3. The method of claim 1, wherein removing energy comprises applying cryotherapy to the nasal tissue, and wherein the treatment element comprises a cryotherapy delivery member.

4. The method of claim 1, wherein applying energy comprises injuring the nasal tissue.

5. The method of claim 1, further comprising, before applying energy to, or removing energy from, the nasal tissue, injecting a polymerizing liquid into or below the nasal tissue.

6. The method of claim 1, comprising both applying energy to and removing energy from the nasal tissue with the treatment element.

7. The method of claim 6, wherein applying and removing the energy is performed in a cyclical fashion to repeatedly heat and cool the nasal tissue.

8. The method of claim 1, wherein the property is a mechanical property of the nasal tissue.

9. The method of claim 1, wherein the property is a property of extracellular matrix components of the nasal tissue and the method does not damage chondrocytes of the nasal tissue.

10. The method of claim 1, wherein the property of the tissue is the strength of the nasal tissue to resist a conformational change in response to negative pressure of inspiration.

11. The method of claim 1, further comprising cooling the nasal tissue or tissue near the nasal tissue to be treated before, during, or after applying energy.

12. The method of claim 1, wherein applying the treatment surface to the nasal tissue and applying the energy modifies a mechanical property of the nasal tissue in a manner that increases a volumetric airflow rate of air flowing from an exterior of the nasal airway into a nasopharynx without changing a shape of an internal nasal valve.

13. The method of claim 1, further comprising delivering a cauterizing agent to the nasal tissue.

14. A method of treating a patient's nasal airway by modifying a property of nasal tissue, the method comprising:

positioning a treatment element within a nasal airway adjacent to nasal tissue to be treated, wherein the treatment element comprises a convex treatment surface;

deforming the nasal tissue into a concave shape by pressing the convex treatment surface of the treatment element against the nasal tissue to be treated; and delivering energy to, or removing energy from, the nasal tissue to modify a property of the nasal tissue without ablating the tissue, wherein the nasal tissue at least partially maintains the modified property after the treatment element is removed and the nasal tissue heals.

15. The method of claim 14, wherein delivering energy to the nasal tissue comprises delivering energy to at least one of the nasal valve, tissue near the nasal valve, or upper lateral cartilage tissue.

16. The method of claim 14, further comprising cooling the nasal tissue to be treated or tissue near the nasal tissue to be treated before, during, or after delivering energy to the nasal tissue.

17. The method of claim 14, wherein delivering energy to, or removing energy from, the nasal tissue comprises:

measuring a temperature near the nasal tissue; and adjusting a level of the energy delivered to, or removed from, the tissue, based on the measured temperature.

18. The method of claim 14, further comprising, before positioning the treatment element, inserting a positioning element into the nasal airway to determine a position for positioning the treatment element.

19. The method of claim 14, wherein delivering energy to or removing energy from the nasal tissue comprises delivering or removing energy for about 15 seconds to about 1 minute.

20. The method of claim 14, wherein delivering energy to the nasal tissue comprises heating the tissue to a temperature of about 50° C. to about 70° C.

21. The method of claim 14, wherein deforming the nasal tissue and delivering or removing energy causes stress relaxation in the nasal tissue without weakening the tissue.

22. The method of claim 14, wherein delivering energy comprises delivering energy in a form selected from the group consisting of ultrasound, microwave, heat, radiofrequency, electrical, light and laser.

23. The method of claim 14, wherein removing energy comprises applying cryotherapy to the nasal tissue, and wherein the treatment element comprises a cryotherapy delivery member.

24. A method of modifying a property of nasal tissue of or near a nasal valve, without using a surgical incision or an implant, to decrease airflow resistance or perceived airflow resistance in a nasal airway, the method comprising:

positioning a treatment surface of an airway treatment device within a nasal airway adjacent to a nasal tissue to be treated;

injecting a polymerizing liquid into or below the nasal tissue, before or after positioning the treatment surface;

applying the treatment surface to the nasal tissue with sufficient force to alter a shape of the nasal tissue; and applying energy to, or removing energy from, the nasal tissue with the treatment element, to change the property of the nasal tissue.

* * * * *